United States Patent
Zha et al.

(10) Patent No.: US 10,106,598 B2
(45) Date of Patent: *Oct. 23, 2018

(54) SURFACE, ANCHORED FC-BAIT ANTIBODY DISPLAY SYSTEM

(71) Applicant: Merck Sharp & Dohme Corp., Rahway, NJ (US)

(72) Inventors: Dongxing Zha, Etna, NH (US); Hussam Hisham Shaheen, Lebanon, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/164,773

(22) Filed: May 25, 2016

(65) Prior Publication Data

US 2016/0355569 A1 Dec. 8, 2016
US 2018/0002402 A9 Jan. 4, 2018

Related U.S. Application Data

(62) Division of application No. 13/990,941, filed as application No. PCT/US2011/062286 on Nov. 29, 2011, now Pat. No. 9,365,846.

(Continued)

(51) Int. Cl.
*C40B 30/04* (2006.01)
*C07K 16/00* (2006.01)
(Continued)

(52) U.S. Cl.
CPC ............ *C07K 16/00* (2013.01); *C07K 16/005* (2013.01); *C07K 16/32* (2013.01); *C07K 16/40* (2013.01);
(Continued)

(58) Field of Classification Search
None
See application file for complete search history.

(56) References Cited

U.S. PATENT DOCUMENTS

2007/0105199 A1 5/2007 Yan et al.
2009/0163379 A1 6/2009 Wang et al.
(Continued)

FOREIGN PATENT DOCUMENTS

EP 1743938 7/2005
WO WO2008100816 8/2008
(Continued)

OTHER PUBLICATIONS

U.S. Appl. No. 13/990,941, filed Aug. 6, 2013.
(Continued)

*Primary Examiner* — Christian C Boesen
(74) *Attorney, Agent, or Firm* — John David Reilly; Laura M. Ginkel

(57) ABSTRACT

The present invention provides, in part, an antibody display system that simultaneously uses a secretion and a display mode. A bait complexed with a monovalent antibody fragment can be expressed on the surface of the host cell wherein the fragment may be assayed for antigen binding while full antibody is simultaneously secreted from the host cell. Methods of using the system for identifying antibodies that bind specifically to an antigen of interest are also provided. Polypeptides, polynucleotides and host cells useful for making the antibody display system are also provided along with methods of use thereof.

11 Claims, 13 Drawing Sheets

Specification includes a Sequence Listing.

Related U.S. Application Data

(60) Provisional application No. 61/458,771, filed on Dec. 1, 2010.

(51) Int. Cl.
  *C07K 16/40* (2006.01)
  *G01N 33/68* (2006.01)
  *C07K 16/32* (2006.01)

(52) U.S. Cl.
  CPC ..... *G01N 33/6845* (2013.01); *G01N 33/6854* (2013.01); *C07K 2317/14* (2013.01); *C07K 2317/52* (2013.01); *C07K 2319/00* (2013.01); *C40B 30/04* (2013.01); *G01N 2440/38* (2013.01)

(56) References Cited

U.S. PATENT DOCUMENTS

| | | |
|---|---|---|
| 2010/0009866 A1 | 1/2010 | Prinz et al. |
| 2010/0075326 A1 | 3/2010 | Jin |
| 2010/0331192 A1 | 12/2010 | Zha et al. |

FOREIGN PATENT DOCUMENTS

| | | |
|---|---|---|
| WO | WO2009111183 | 9/2009 |
| WO | WO2011100566 | 8/2011 |

OTHER PUBLICATIONS

Shaheen et al., A dual-mode surface display system for the maturation and production of monoclonal antibodies in glyco-engineered Pichia pastoris., Plos One, 2013, 1-10, 8-7, US.

BP550-Fc-Sed1p

Kappa ELISA

| | SID | µg/mL | 2 | 3 | 4 | 5 | 6 | 7 | 8 | 9 | 10 | 11 | 12 |
|---|---|---|---|---|---|---|---|---|---|---|---|---|---|
| AX189 Ctrl | | | | Presorted Library | | | | | Round 2 100nM (S2) Sorted Library | | | | |
| | A | 250 | 5.2 | 4.3 | 3.9 | 1.5 | 1.9 | 4.8 | 0.4 | 4.1 | 3.1 | 3.2 | 2.4 |
| | B | 83 | 4.0 | 2.1 | 5.9 | 4.5 | 4.7 | 6.8 | 2.3 | 2.5 | 3.6 | 3.8 | 3.8 |
| | C | 27.8 | 4.1 | 2.5 | 4.4 | 6.6 | 3.9 | 6.4 | 7.2 | 3.2 | 2.7 | 2.9 | 3.0 |
| | D | 9.3 | 3.5 | 6.1 | 3.9 | 1.6 | 0.5 | 4.0 | 3.4 | 3.2 | 4.3 | 1.0 | 2.2 |
| | E | 3.1 | 4.1 | 3.8 | 7.5 | 3.4 | 8.4 | 6.2 | 3.3 | 0.4 | 1.5 | 2.9 | 3.0 |
| | F | 1.0 | 3.5 | 5.3 | 6.8 | 1.8 | 4.0 | 4.1 | 3.1 | 2.7 | 3.7 | 4.3 | 0.4 |
| | G | 0.3 | 2.9 | 4.8 | 5.0 | 2.7 | 3.4 | 2.2 | 2.6 | 4.4 | 5.5 | 6.6 | 3.2 |
| | H | 0.1 | 2.2 | 2.6 | 2.5 | 1.5 | 4.4 | 3.8 | 2.1 | 1.9 | 4.1 | 2.3 | 2.4 |

PCSK9 ELISA

| SID | µg/mL | 2 | 3 | 4 | 5 | 6 | 7 | 8 | 9 | 10 | 11 | 12 |
|---|---|---|---|---|---|---|---|---|---|---|---|---|
| A | 100 | 59.8 | 0.4 | 0.3 | 0.1 | 0.0 | 0.8 | 1.7 | >Max | 267.9 | 243.5 | 34.0 |
| B | 33 | 147.8 | <Min | 0.3 | <Min | 0.4 | 0.3 | 86.4 | 67.7 | 217.6 | >Max | 49.6 |
| C | 11.1 | 111.1 | 0.0 | 1.0 | <Min | 0.1 | 2.8 | 309.4 | 74.3 | 252.8 | 797.7 | 32.8 |
| D | 3.7 | 120.8 | 0.0 | <Min | <Min | <Min | 0.5 | 22.9 | 120.1 | 80.3 | 7.2 | 45.8 |
| E | 1.2 | 128.3 | 0.1 | 0.2 | <Min | <Min | 0.2 | 53.6 | 0.9 | 26.7 | 181.8 | 231.0 |
| F | 0.4 | 1370.7 | 22.6 | <Min | <Min | 0.0 | <Min | 55.7 | 85.3 | 87.7 | 371.3 | 0.6 |
| G | 0.1 | 135.2 | <Min | <Min | <Min | <Min | 1.6 | 105.6 | 463.6 | 195.6 | 585.5 | 118.6 |
| H | 0.0 | 3353.4 | <Min | <Min | <Min | 0.6 | <Min | 53.6 | 204.8 | 590.3 | 111.7 | 58.1 |

FIG.7a

BP551-Fc-Sed1p

Kappa ELISA

| | SID | AX189 Ctrl µg/mL | Presorted Library | | | | | Round 2 100nM (S2) Sorted Library | | | | |
|---|---|---|---|---|---|---|---|---|---|---|---|---|
| | | | 2 | 3 | 4 | 5 | 6 | 7 | 8 | 9 | 10 | 11 | 12 |
| | A | 250 | 5.0 | 5.4 | 0.9 | 2.3 | 0.3 | 1.4 | 5.9 | 3.6 | 4.3 | 5.0 | 4.9 |
| | B | 83 | 5.1 | 2.4 | 0.1 | 2.9 | 2.0 | 4.5 | 3.2 | 2.9 | 7.9 | 5.9 | 2.8 |
| | C | 27.8 | 4.0 | 4.9 | 1.9 | 3.7 | 3.6 | 3.9 | 3.5 | 0.2 | 0.1 | 8.6 | 0.1 |
| | D | 9.3 | 3.7 | 5.5 | 3.3 | 1.9 | 3.7 | 0.1 | 7.2 | 7.4 | 0.1 | 5.4 | 0.1 |
| | E | 3.1 | 5.0 | 0.3 | 0.2 | 3.0 | 3.8 | 2.8 | 2.9 | 3.9 | 4.8 | 4.4 | 3.5 |
| | F | 10 | 2.7 | 0.1 | 3.2 | 3.8 | 3.5 | 3.9 | 6.4 | 2.8 | 4.7 | 6.3 | 4.3 |
| | G | 0.3 | 2.8 | 0.1 | 1.9 | 2.1 | 2.0 | 3.4 | 3.9 | 3.0 | 2.6 | 2.7 | 3.5 |
| | H | 0.1 | 2.2 | 1.9 | 0.3 | 1.4 | 1.5 | 1.5 | 2.4 | 1.7 | 4.5 | 3.9 | 3.9 |

PCSK9 ELISA

| | SID | µg/mL | 2 | 3 | 4 | 5 | 6 | 7 | 8 | 9 | 10 | 11 | 12 |
|---|---|---|---|---|---|---|---|---|---|---|---|---|---|
| | A | 100 | 73.3 | 15.4 | 0.5 | 0.0 | 0.2 | 0.3 | 281.9 | 170.6 | 58.2 | 49.9 | 55.3 |
| | B | 33 | 202.0 | 0.4 | 0.1 | 0.1 | 0.3 | 0.4 | 210.7 | 147.9 | 720.9 | 228.1 | 32.7 |
| | C | 11.1 | 102.6 | 0.5 | 1.3 | 8.1 | 0.0 | 1.6 | 42.9 | 167.5 | 83.7 | 855.9 | 138.5 |
| | D | 3.7 | 143.5 | 0.0 | <Min | 0.1 | 0.0 | 0.1 | 97.3 | >Max | 592.4 | 67.2 | 115.6 |
| | E | 1.2 | 207.1 | 0.1 | 0.2 | 0.0 | 0.6 | 0.2 | 14.1 | 249.2 | 252.6 | 190.0 | 270.1 |
| | F | 0.4 | 173.0 | 0.0 | <Min | <Min | 9.3 | 9.5 | 132.3 | 32.5 | 43.3 | 286.8 | 87.0 |
| | G | 0.1 | 93.3 | 0.2 | 0.1 | 0.1 | 0.2 | 0.9 | 296.2 | 108.8 | 33.6 | 48.6 | 181.1 |
| | H | 0.0 | 95.4 | <Min | <Min | <Min | 0.1 | <Min | 125.6 | 42.8 | 172.3 | 150.6 | 70.5 |

FIG. 7b

SEQUENCE LISTING

<160> NUMBER OF SEQ ID NOS: 6

<210> SEQ ID NO 1
<211> LENGTH: 226

```
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 2
<211> LENGTH: 322
<212> TYPE: PRT
<213> ORGANISM: Saccharomyces cerevisiae

<400> SEQUENCE: 2

Val Asp Gln Phe Ser Asn Ser Thr Ser Ala Ser Ser Thr Asp Val Thr
1               5                   10                  15

Ser Ser Ser Ser Ile Ser Thr Ser Ser Gly Ser Val Thr Ile Thr Ser
            20                  25                  30

Ser Glu Ala Pro Glu Ser Asp Asn Gly Thr Ser Thr Ala Ala Pro Thr
        35                  40                  45

Glu Thr Ser Thr Glu Ala Pro Thr Thr Ala Ile Pro Thr Asn Gly Thr
    50                  55                  60

Ser Thr Glu Ala Pro Thr Thr Ala Ile Pro Thr Asn Gly Thr Ser Thr
65                  70                  75                  80

Glu Ala Pro Thr Asp Thr Thr Thr Glu Ala Pro Thr Thr Ala Leu Pro
                85                  90                  95

Thr Asn Gly Thr Ser Thr Glu Ala Pro Thr Asp Thr Thr Thr Glu Ala
            100                 105                 110
```

-continued

Pro Thr Thr Gly Leu Pro Thr Asn Gly Thr Thr Ser Ala Phe Pro Pro
             115                 120                 125

Thr Thr Ser Leu Pro Pro Ser Asn Thr Thr Thr Pro Pro Tyr Asn
    130                 135                 140

Pro Ser Thr Asp Tyr Thr Thr Asp Tyr Thr Val Val Thr Glu Tyr Thr
145                 150                 155                 160

Thr Tyr Cys Pro Glu Pro Thr Thr Phe Thr Thr Asn Gly Lys Thr Tyr
                165                 170                 175

Thr Val Thr Glu Pro Thr Thr Leu Thr Ile Thr Asp Cys Pro Cys Thr
            180                 185                 190

Ile Glu Lys Pro Thr Thr Thr Ser Thr Thr Glu Tyr Thr Val Val Thr
        195                 200                 205

Glu Tyr Thr Thr Tyr Cys Pro Glu Pro Thr Thr Phe Thr Thr Asn Gly
    210                 215                 220

Lys Thr Tyr Thr Val Thr Glu Pro Thr Thr Leu Thr Ile Thr Asp Cys
225                 230                 235                 240

Pro Cys Thr Ile Glu Lys Ser Glu Ala Pro Glu Ser Ser Val Pro Val
                245                 250                 255

Thr Glu Ser Lys Gly Thr Thr Lys Glu Thr Gly Val Thr Thr Lys
            260                 265                 270

Gln Thr Thr Ala Asn Pro Ser Leu Thr Val Ser Thr Val Pro Val
        275                 280                 285

Ser Ser Ser Ala Ser Ser His Ser Val Val Ile Asn Ser Asn Gly Ala
    290                 295                 300

Asn Val Val Pro Gly Ala Leu Gly Leu Ala Gly Val Ala Met Leu
305                 310                 315                 320

Phe Leu

<210> SEQ ID NO 3
<211> LENGTH: 19
<212> TYPE: PRT
<213> ORGANISM: Homo sapiens

<400> SEQUENCE: 3

Met Arg Phe Pro Ser Ile Phe Thr Ala Val Leu Phe Ala Ala Ser Ser
1               5                   10                  15

Ala Leu Ala

<210> SEQ ID NO 4
<211> LENGTH: 570
<212> TYPE: PRT
<213> ORGANISM: Artificial Sequence
<220> FEATURE:
<223> OTHER INFORMATION: Homo sapiens and Saccharmomyces cerevisiae

<400> SEQUENCE: 4

Met Arg Phe Pro Ser Ile Phe Thr Ala Val Leu Phe Ala Ala Ser Ser
1               5                   10                  15

Ala Leu Ala Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

-continued

```
Val Glu Val His Asn Ala Lys Thr Lys Pro Arg Glu Glu Gln Tyr Asn
             85                  90                  95
Ser Thr Tyr Arg Val Val Ser Val Leu Thr Val Leu His Gln Asp Trp
            100                 105                 110
Leu Asn Gly Lys Glu Tyr Lys Cys Lys Val Ser Asn Lys Ala Leu Pro
        115                 120                 125
Ala Pro Ile Glu Lys Thr Ile Ser Lys Ala Lys Gly Gln Pro Arg Glu
    130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
        195                 200                 205
Leu Thr Val Asp Lys Ser Arg Trp Gln Gln Gly Asn Val Phe Ser Cys
    210                 215                 220
Ser Val Met His Glu Ala Leu His Asn His Tyr Thr Gln Lys Ser Leu
225                 230                 235                 240
Ser Leu Ser Pro Gly Gly Gly Val Asp Gln Phe Ser Asn Ser Thr
                245                 250                 255
Ser Ala Ser Ser Thr Asp Val Thr Ser Ser Ser Ile Ser Thr Ser
            260                 265                 270
Ser Gly Ser Val Thr Ile Thr Ser Ser Glu Ala Pro Glu Ser Asp Asn
        275                 280                 285
Gly Thr Ser Thr Ala Ala Pro Thr Glu Thr Ser Thr Glu Ala Pro Thr
    290                 295                 300
Thr Ala Ile Pro Thr Asn Gly Thr Ser Thr Glu Ala Pro Thr Thr Ala
305                 310                 315                 320
Ile Pro Thr Asn Gly Thr Ser Thr Glu Ala Pro Thr Asp Thr Thr Thr
                325                 330                 335
Glu Ala Pro Thr Thr Ala Leu Pro Thr Asn Gly Thr Ser Thr Glu Ala
            340                 345                 350
Pro Thr Asp Thr Thr Thr Glu Ala Pro Thr Gly Leu Pro Thr Asn
        355                 360                 365
Gly Thr Thr Ser Ala Phe Pro Pro Thr Thr Ser Leu Pro Pro Ser Asn
    370                 375                 380
Thr Thr Thr Thr Pro Pro Tyr Asn Pro Ser Thr Asp Tyr Thr Thr Asp
385                 390                 395                 400
Tyr Thr Val Val Thr Glu Tyr Thr Thr Tyr Cys Pro Glu Pro Thr Thr
                405                 410                 415
Phe Thr Thr Asn Gly Lys Thr Tyr Thr Val Thr Glu Pro Thr Thr Leu
            420                 425                 430
Thr Ile Thr Asp Cys Pro Cys Thr Ile Glu Lys Pro Thr Thr Thr Ser
        435                 440                 445
Thr Thr Glu Tyr Thr Val Val Thr Glu Tyr Thr Thr Tyr Cys Pro Glu
    450                 455                 460
Pro Thr Thr Phe Thr Thr Asn Gly Lys Thr Tyr Thr Val Thr Glu Pro
465                 470                 475                 480
Thr Thr Leu Thr Ile Thr Asp Cys Pro Cys Thr Ile Glu Lys Ser Glu
                485                 490                 495
Ala Pro Glu Ser Ser Val Pro Val Thr Glu Ser Lys Gly Thr Thr Thr
```

|     |     |     |     |     | 500 |     |     |     | 505 |     |     |     |     | 510 |
| --- | --- | --- | --- | --- | --- | --- | --- | --- | --- | --- | --- | --- | --- | --- |

Lys Glu Thr Gly Val Thr Thr Lys Gln Thr Thr Ala Asn Pro Ser Leu
           515                    520                  525

Thr Val Ser Thr Val Val Pro Val Ser Ser Ala Ser Ser His Ser
      530                  535                540

Val Val Ile Asn Ser Asn Gly Ala Asn Val Val Pro Gly Ala Leu
545                  550                  555                560

Gly Leu Ala Gly Val Ala Met Leu Phe Leu
          565                  570

<210> SEQ ID NO 5
<211> LENGTH: 8640
<212> TYPE: DNA
<213> ORGANISM: Artificial Sequence
<220> FEATURE:
<223> OTHER INFORMATION: Plasmid pGLY3033

<400> SEQUENCE: 5

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | gagatctaac | atccaaagac | 420 |
| gaaaggttga | atgaaacctt | tttgccatcc | gacatccaca | ggtccattct | cacacataag | 480 |
| tgccaaacgc | aacaggaggg | gatacactag | cagcagaccg | ttgcaaacgc | aggacctcca | 540 |
| ctcctcttct | cctcaacacc | cacttttgcc | atcgaaaaac | cagcccagtt | attgggcttg | 600 |
| attgagctc | gctcattcca | attccttcta | ttaggctact | aacaccatga | ctttattagc | 660 |
| ctgtctatcc | tggccccct | ggcgaggttc | atgtttgttt | atttccgaat | gcaacaagct | 720 |
| ccgcattaca | cccgaacatc | actccagatg | agggctttct | gagtgtgggg | tcaaatagtt | 780 |
| tcatgttccc | caaatggccc | aaaactgaca | gtttaaacgc | tgtcttggaa | cctaatatga | 840 |
| caaaagcgtg | atctcatcca | agatgaacta | agtttggttc | gttgaaatgc | taacggccag | 900 |
| ttggtcaaaa | agaaacttcc | aaaagtcggc | ataccgtttg | tcttgtttgg | tattgattga | 960 |
| cgaatgctca | aaaataatct | cattaatgct | tagcgcagtc | tctctatcgc | ttctgaaccc | 1020 |
| cggtgcacct | gtgccgaaac | gcaaatgggg | aaacaccccgc | ttttttggatg | attatgcatt | 1080 |
| gtctccacat | tgtatgcttc | caagattctg | gtgggaatac | tgctgatagc | ctaacgttca | 1140 |
| tgatcaaaat | ttaactgttc | taacccctac | ttgacagcaa | tatataaaca | gaaggaagct | 1200 |
| gccctgtctt | aaaccttttt | ttttatcatc | attattagct | tactttcata | attgcgactg | 1260 |
| gttccaattg | acaagctttt | gattttaacg | acttttaacg | acaacttgag | aagatcaaaa | 1320 |
| aacaactaat | tattcgaaac | ggaattcacg | atggtcgctt | ggtggtcttt | gtttctgtac | 1380 |
| ggtcttcagg | tcgctgcacc | tgctttggct | acttccagat | ggagggatt | gcaatccgaa | 1440 |
| aaccacagat | tgagaatgaa | gatcactgag | ttggacaagg | acttggagga | agttactatg | 1500 |
| cagttgcagg | atgttggtgg | ttgtgagcag | aagttgatct | ccgaagagga | tttggtcgac | 1560 |
| caattctcta | actctacttc | cgcttcctct | actgacgtta | cttcctcctc | ctctatttct | 1620 |
| acttcctccg | gttccgttac | tattacttcc | tctgaggctc | cagaatctga | caacggtact | 1680 |

```
tctactgctg ctccaactga aacttctact gaggctccta ctactgctat tccaactaac    1740
ggaacttcca cagaggctcc aacaacagct atccctacaa acggtacatc cactgaagct    1800
cctactgaca ctactacaga agctccaact actgctttgc ctactaatgg tacatcaaca    1860
gaggctccta cagatacaac aactgaagct ccaacaactg gattgccaac aaacggtact    1920
acttctgctt tcccaccaac tacttccttg ccaccatcca acactactac tactccacca    1980
tacaacccat ccactgacta cactactgac tacacagttg ttactgagta cactacttac    2040
tgtccagagc caactacttt cacaacaaac ggaaagactt acactgttac tgagcctact    2100
actttgacta tcactgactg tccatgtact atcgagaagc caactactac ttccactaca    2160
gagtatactg ttgttacaga atacacaaca tattgtcctg agccaacaac attcactact    2220
aatggaaaaa catacacagt tacagaacca actacattga caattacaga ttgtccttgt    2280
acaattgaga agtccgaggc tcctgaatct tctgttccag ttactgaatc caagggtact    2340
actactaaag aaactggtgt tactactaag cagactactg ctaacccatc cttgactgtt    2400
tccactgttg ttccagtttc ttcctctgct tcttcccact ccgttgttat caactccaac    2460
ggtgctaacg ttgttgttcc tggtgctttg ggattggctg tgttgctat gttgttcttg     2520 taatagggcc ggccatttaa atacaggccc cttttccttt gtcgatatca tgtaattagt    2580
tatgtcacgc ttacattcac gccctcctcc cacatccgct ctaaccgaaa aggaaggagt    2640
tagacaacct gaagtctagg tccctattta tttttttaa tagttatgtt agtattaaga     2700
acgttattta tatttcaaat ttttcttttt tttctgtaca aacgcgtgta cgcatgtaac    2760
attatactga aaaccttgct tgagaaggtt ttgggacgct cgaaggcttt aatttgcaag    2820
ctggatccgc ggccgcttac gcgccgttct tcgcttggtc ttgtatctcc ttacactgta    2880
tcttcccatt tgcgtttagg tggttatcaa aaactaaaag gaaaaatttc agatgtttat    2940
ctctaaggtt ttttcttttt acagtataac acgtgatgcg tcacgtggta ctagattacg    3000
taagttattt tggtccggtg ggtaagtggg taagaataga aagcatgaag gtttacaaaa    3060
acgcagtcac gaattattgc tacttcgagc ttggaaccac cccaaagatt atattgtact    3120
gatgcactac cttctcgatt tgctcctcc aagaacctac gaaaaacatt tcttgagcct     3180
tttcaaccta gactacacat caagttattt aaggtatgtt ccgttaacat gtaagaaaag    3240
gagaggatag atcgtttatg gggtacgtcg cctgattcaa gcgtgaccat tcgaagaata    3300
ggccttcgaa agctgaataa agcaaatgtc agttgcgatt ggtatgctga caaattagca    3360
taaaaagcaa tagactttct aaccacctgt ttttttcctt ttactttatt tatattttgc    3420
caccgtacta acaagttcag acaaattaat taacaccatg tcagaagatc aaaaaagtga    3480
aaattccgta ccttctaagg ttaatatggt gaatcgcacc gatatactga ctacgatcaa    3540
gtcattgtca tggcttgact tgatgttgcc atttactata attctctcca taatcattgc    3600
agtaataatt tctgtctatg tgccttcttc ccgtcacact tttgacgctg aaggtcatcc    3660
caatctaatg ggagtgtcca ttcctttgac tgttggtatg attgtaatga tgattccccc    3720
gatctgcaaa gtttcctggg agtctattca caagtacttc tacaggagct atataaggaa    3780
gcaactagcc ctctcgttat ttttgaattg ggtcatcggt cctttgttga tgacagcatt    3840
ggcgtggatg gcgctattcg attataagga ataccgtcaa ggcattatta tgatcggagt    3900
agctagatgc attgccatgg tgctaatttg gaatcagatt gctggaggag acaatgatct    3960
ctgcgtcgtg cttgttatta caaactcgct tttacagatg gtattatatg caccattgca    4020
```

```
gatattttac tgttatgtta tttctcatga ccacctgaat acttcaaata gggtattatt     4080
cgaagaggtt gcaaagtctg tcggagtttt tctcggcata ccactgggaa ttggcattat     4140
catacgtttg ggaagtctta ccatagctgg taaaagtaat tatgaaaaat acattttgag     4200
atttatttct ccatgggcaa tgatcggatt tcattacact ttatttgtta ttttattag     4260 tagaggttat caatttatcc acgaaattgg ttctgcaata ttgtgctttg tcccattggt     4320
gctttacttc tttattgcat ggttttgac cttcgcatta atgaggtact tatcaatatc     4380
taggagtgat acacaaagag aatgtagctg tgaccaagaa ctactttaa agagggtctg     4440 gggaagaaag tcttgtgaag ctagcttttc tattacgatg acgcaatgtt tcactatggc     4500
ttcaaataat tttgaactat ccctggcaat tgctatttcc ttatatggta acaatagcaa     4560
gcaagcaata gctgcaacat ttgggccgtt gctagaagtt ccaattttat tgattttggc     4620
aatagtcgcg agaatcctta aaccatatta tatatggaac aatagaaatt aattaacagg     4680
ccccttttcc tttgtcgata tcatgtaatt agttatgtca cgcttacatt cacgccctcc     4740
tcccacatcc gctctaaccg aaaaggaagg agttagacaa cctgaagtct aggtccctat     4800
ttattttttt taatagttat gttagtatta agaacgttat ttatatttca aattttttctt     4860 ttttttctgt acaaacgcgt gtacgcatgt aacattatac tgaaaaccct gcttgagaag     4920
gttttgggac gctcgaaggc tttaattttgc aagctgcggc ctaaggcgcg ccaggccata     4980
atggcccaaa tgcaagagga cattagaaat gtgtttggta agaacatgaa gccggaggca     5040
tacaaacgat tcacagattt gaaggaggaa acaaactgc atccaccgga agtgccagca     5100
gccgtgtatg ccaaccttgc tctcaaaggc attcctacgg atctgagtgg gaaatatctg     5160
agattcacag cccactatt ggaacagtac caaacctagt ttggccgatc catgattatg     5220
taatgcatat agttttgtc gatgctcacc cgtttcgagt ctgtctcgta tcgtcttacg     5280
tataagttca agcatgttta ccaggtctgt tagaaactcc tttgtgaggg caggacctat     5340
tcgtctcggt cccgttgttt ctaagagact gtacagccaa gcgcagaatg gtggcattaa     5400
ccataagagg attctgatcg gacttggtct attggctatt ggaaccaccc tttacgggac     5460
aaccaaccct accaagactc ctattgcatt tgtggaacca gccacggaaa gagcgtttaa     5520
ggacggagac gtctctgtga ttttgttct cggaggtcca ggagctggaa aaggtaccca     5580
atgtgccaaa ctagtgagta attacggatt tgttcacctg tcagctggag acttgttacg     5640
tgcagaacag aagagggagg ggtctaagta tggagagatg atttcccagt atatcagaga     5700
tggactgata gtacctcaag aggtcaccat tgcgctcttg gagcaggcca tgaaggaaaa     5760
cttcgagaaa gggaagacac ggttcttgat tgatggattc cctcgtaaga tggaccaggc     5820
caaaactttt gaggaaaaag tcgcaaagtc caaggtgaca cttttctttg attgtcccga     5880
atcagtgctc cttgagagat tacttaaaag aggacagaca agcggaagag aggatgataa     5940
tgcggagagt atcaaaaaaa gattcaaaac attcgtggaa acttcgatgc ctgtggtgga     6000
ctatttcggg aagcaaggac gcgttttgaa ggtatcttgt gaccaccctg tggatcaagt     6060
gtattcacag gttgtgtcgg tgctaaaaga gaagggatc tttgccgata acgagacgga     6120
gaataaataa acattgtaat aagatttaga ctgtgaatgt tctatgtaat atttttcgag     6180
atactgtatc tatctggtgt accgtatcac tctggacttg caaactcatt gattacttgt     6240
gcaatgggca agaaggatag ctctagaaag aagaagaaaa aggagccgcc tgaagagctg     6300
gatctttccg aggttgttcc aacttttggt tatgaggaat tcatgttga gcaagaggag     6360 aatccggtcg atcaagacga acttgacggc cataatggcc tagcttggcg taatcatggt     6420
```

-continued

```
catagctgtt tcctgtgtga aattgttatc cgctcacaat tccacacaac atacgagccg    6480
gaagcataaa gtgtaaagcc tggggtgcct aatgagtgag ctaactcaca ttaattgcgt    6540
tgcgctcact gcccgctttc cagtcgggaa acctgtcgtg ccagctgcat taatgaatcg    6600
gccaacgcgc ggggagaggc ggtttgcgta ttgggcgctc ttccgcttcc tcgctcactg    6660
actcgctgcg ctcggtcgtt cggctgcggc gagcggtatc agctcactca aaggcggtaa    6720
tacggttatc cacagaatca ggggataacg caggaaagaa catgtgagca aaaggccagc    6780
aaaaggccag gaaccgtaaa aaggccgcgt tgctggcgtt tttccatagg ctccgccccc    6840
ctgacgagca tcacaaaaat cgacgctcaa gtcagaggtg cgaaacccg acaggactat    6900 aaagatacca ggcgtttccc cctggaagct ccctcgtgcg ctctcctgtt ccgaccctgc    6960
cgcttaccgg atacctgtcc gcctttctcc cttcgggaag cgtggcgctt tctcatagct    7020
cacgctgtag gtatctcagt tcggtgtagg tcgttcgctc caagctgggc tgtgtgcacg    7080
aaccccccgt tcagcccgac cgctgcgcct tatccggtaa ctatcgtctt gagtccaacc    7140
cggtaagaca cgacttatcg ccactggcag cagccactgg taacaggatt agcagagcga    7200
ggtatgtagg cggtgctaca gagttcttga agtggtggcc taactacggc tacactagaa    7260
ggacagtatt tggtatctgc gctctgctga agccagttac cttcggaaaa agagttggta    7320
gctcttgatc cggcaaacaa accaccgctg gtagcggtgg tttttttgtt tgcaagcagc    7380
agattacgcg cagaaaaaaa ggatctcaag aagatccttt gatcttttct acggggtctg    7440
acgctcagtg gaacgaaaac tcacgttaag ggattttggt catgagatta tcaaaaagga    7500
tcttcaccta gatcctttta aattaaaaat gaagttttaa atcaatctaa agtatatatg    7560
agtaaacttg gtctgacagt taccaatgct taatcagtga ggcacctatc tcagcgatct    7620
gtctatttcg ttcatccata gttgcctgac tccccgtcgt gtagataact acgatacggg    7680
agggcttacc atctggcccc agtgctgcaa tgataccgcg agaccacgc tcaccggctc    7740 cagatttatc agcaataaac cagccagccg gaagggccga gcgcagaagt ggtcctgcaa    7800
ctttatccgc ctccatccag tctattaatt gttgccggga agctagagta agtagttcgc    7860
cagttaatag tttgcgcaac gttgttgcca ttgctacagg catcgtggtg tcacgctcgt    7920
cgtttggtat ggcttcattc agctccggtt cccaacgatc aaggcgagtt acatgatccc    7980
ccatgttgtg caaaaaagcg gttagctcct tcggtcctcc gatcgttgtc agaagtaagt    8040
tggccgcagt gttatcactc atggttatgg cagcactgca taattctctt actgtcatgc    8100
catccgtaag atgcttttct gtgactggtg agtactcaac caagtcattc tgagaatagt    8160
gtatgcggcg accgagttgc tcttgcccgg cgtcaatacg ggataatacc gcgccacata    8220
gcagaacttt aaaagtgctc atcattggaa aacgttcttc ggggcgaaaa ctctcaagga    8280
tcttaccgct gttgagatcc agttcgatgt aacccactcg tgcacccaac tgatcttcag    8340
catcttttac tttcaccagc gtttctgggt gagcaaaaac aggaaggcaa aatgccgcaa    8400
aaaagggaat aagggcgaca cggaaatgtt gaatactcat actcttcctt tttcaatatt    8460
attgaagcat ttatcagggt tattgtctca tgagcggata catatttgaa tgtatttaga    8520
aaaataaaca ataggggtt ccgcgcacat ttccccgaaa agtgccacct gacgtctaag    8580
aaaccattat tatcatgaca ttaacctata aaaataggcg tatcacgagg ccctttcgtc    8640
```

<210> SEQ ID NO 6
<211> LENGTH: 9180
<212> TYPE: PRT

<213> ORGANISM: Artificial Sequence
<220> FEATURE:
<223> OTHER INFORMATION: Plasmid pGLY9008

<400> SEQUENCE: 6

```
Thr Cys Gly Cys Gly Cys Gly Thr Thr Cys Gly Gly Thr Gly Ala
1               5                   10                  15

Thr Gly Ala Cys Gly Gly Thr Gly Ala Ala Ala Cys Cys Thr Cys
            20                  25                  30

Thr Gly Ala Cys Ala Cys Ala Thr Gly Cys Ala Gly Thr Cys Cys
            35                  40                  45

Cys Gly Gly Ala Gly Ala Cys Gly Gly Thr Cys Ala Cys Ala Gly Cys
50                      55                  60

Thr Thr Gly Thr Cys Thr Gly Thr Ala Ala Gly Cys Gly Gly Ala Thr
65                  70                  75                  80

Gly Cys Cys Gly Gly Gly Ala Gly Cys Ala Gly Ala Cys Ala Ala Gly
                85                  90                  95

Cys Cys Cys Gly Thr Cys Ala Gly Gly Cys Gly Cys Gly Thr Cys
                100                 105                 110

Ala Gly Cys Gly Gly Gly Thr Gly Thr Thr Gly Gly Cys Gly Gly Gly
115                     120                 125

Thr Gly Thr Cys Gly Gly Gly Gly Cys Thr Gly Gly Cys Thr Thr Ala
            130                 135                 140

Ala Cys Thr Ala Thr Gly Cys Gly Gly Cys Ala Thr Cys Ala Gly Ala
145                 150                 155                 160

Gly Cys Ala Gly Ala Thr Thr Gly Thr Ala Cys Thr Gly Ala Gly Ala
                165                 170                 175

Gly Thr Gly Cys Ala Cys Cys Ala Thr Ala Thr Gly Cys Gly Gly Thr
                180                 185                 190

Gly Thr Gly Ala Ala Ala Thr Ala Cys Cys Gly Cys Ala Cys Ala Gly
            195                 200                 205

Ala Thr Gly Cys Gly Thr Ala Ala Gly Gly Ala Gly Ala Ala Ala Ala
210                 215                 220

Thr Ala Cys Cys Gly Cys Ala Thr Cys Ala Gly Gly Cys Gly Cys Cys
225                 230                 235                 240

Ala Thr Thr Cys Gly Cys Cys Ala Thr Thr Cys Ala Gly Gly Cys Thr
                245                 250                 255

Gly Cys Gly Cys Ala Ala Cys Thr Gly Thr Thr Gly Gly Gly Ala Ala
            260                 265                 270

Gly Gly Gly Cys Gly Ala Thr Cys Gly Gly Thr Gly Cys Gly Gly Gly
            275                 280                 285

Cys Cys Thr Cys Thr Thr Cys Gly Cys Thr Ala Thr Thr Ala Cys Gly
290                 295                 300

Cys Cys Ala Gly Cys Thr Gly Gly Cys Gly Ala Ala Ala Gly Gly Gly
305                 310                 315                 320

Gly Gly Ala Thr Gly Thr Gly Cys Thr Gly Cys Ala Ala Gly Gly Cys
            325                 330                 335

Gly Ala Thr Thr Ala Ala Gly Thr Thr Gly Gly Gly Thr Ala Ala Cys
            340                 345                 350

Gly Cys Cys Ala Gly Gly Gly Thr Thr Thr Thr Cys Cys Cys Ala Gly
                355                 360                 365

Thr Cys Ala Cys Gly Ala Cys Gly Thr Thr Gly Thr Ala Ala Ala Ala
                370                 375                 380

Cys Gly Ala Cys Gly Gly Cys Cys Ala Gly Thr Gly Ala Ala Thr Thr
```

```
            385                 390                 395                 400
Gly Ala Gly Ala Thr Cys Thr Ala Ala Cys Ala Thr Cys Cys Ala Ala
                    405                 410                 415
Ala Gly Ala Cys Gly Ala Ala Ala Gly Gly Thr Thr Gly Ala Ala Thr
                    420                 425                 430
Gly Ala Ala Cys Cys Thr Thr Thr Thr Gly Cys Cys Ala Thr
                    435                 440                 445
Cys Cys Gly Ala Cys Ala Thr Cys Cys Ala Cys Ala Gly Gly Thr Cys
        450                 455                 460
Cys Ala Thr Thr Cys Thr Cys Ala Cys Ala Cys Ala Thr Ala Ala Gly
465                 470                 475                 480
Thr Gly Cys Cys Ala Ala Ala Cys Gly Cys Ala Ala Cys Ala Gly Gly
                    485                 490                 495
Ala Gly Gly Gly Gly Ala Thr Ala Cys Ala Cys Thr Ala Gly Cys Ala
                    500                 505                 510
Gly Cys Ala Gly Ala Cys Cys Gly Thr Thr Gly Cys Ala Ala Ala Cys
                    515                 520                 525
Gly Cys Ala Gly Gly Ala Cys Cys Thr Cys Cys Ala Cys Thr Cys Cys
            530                 535                 540
Thr Cys Thr Thr Cys Thr Cys Cys Thr Cys Ala Cys Ala Cys Cys
545                 550                 555                 560
Cys Ala Cys Thr Thr Thr Thr Gly Cys Cys Ala Thr Cys Gly Ala Ala
                    565                 570                 575
Ala Ala Ala Cys Cys Ala Gly Cys Cys Cys Ala Gly Thr Thr Ala Thr
                    580                 585                 590
Thr Gly Gly Gly Cys Thr Thr Gly Ala Thr Thr Gly Gly Ala Gly Cys
                    595                 600                 605
Thr Cys Gly Cys Thr Cys Ala Thr Thr Cys Cys Ala Ala Thr Thr Cys
        610                 615                 620
Cys Thr Thr Cys Thr Ala Thr Thr Ala Gly Gly Cys Thr Ala Cys Thr
625                 630                 635                 640
Ala Ala Cys Ala Cys Cys Ala Thr Gly Ala Cys Thr Thr Thr Ala Thr
                    645                 650                 655
Thr Ala Gly Cys Cys Thr Gly Thr Cys Thr Ala Thr Cys Cys Thr Gly
                    660                 665                 670
Gly Cys Cys Cys Cys Cys Thr Gly Gly Cys Gly Ala Gly Gly Thr
            675                 680                 685
Thr Cys Ala Thr Gly Thr Thr Thr Gly Thr Thr Ala Thr Thr Thr
        690                 695                 700
Cys Cys Gly Ala Ala Thr Gly Cys Ala Ala Cys Ala Ala Gly Cys Thr
705                 710                 715                 720
Cys Cys Gly Cys Ala Thr Thr Ala Cys Ala Cys Cys Cys Gly Ala Ala
                    725                 730                 735
Cys Ala Thr Cys Ala Cys Thr Cys Cys Ala Gly Ala Thr Gly Ala Gly
                    740                 745                 750
Gly Gly Cys Thr Thr Thr Cys Thr Gly Ala Gly Thr Gly Thr Gly Gly
            755                 760                 765
Gly Gly Thr Cys Ala Ala Ala Thr Ala Gly Thr Thr Cys Ala Thr
                    770                 775                 780
Gly Thr Thr Cys Cys Cys Ala Ala Ala Thr Gly Gly Cys Cys Cys
                    785                 790                 795                 800
Ala Ala Ala Ala Cys Thr Gly Ala Cys Ala Gly Thr Thr Thr Ala Ala
                    805                 810                 815
```

```
Ala Cys Gly Cys Thr Gly Thr Cys Thr Thr Gly Gly Ala Ala Cys Cys
            820                 825                 830
Thr Ala Ala Thr Ala Thr Gly Ala Cys Ala Ala Ala Ala Gly Cys Gly
            835                 840                 845
Thr Gly Ala Thr Cys Thr Cys Ala Thr Cys Ala Ala Gly Ala Thr
            850                 855                 860
Gly Ala Ala Cys Thr Ala Ala Gly Thr Thr Gly Gly Thr Thr Cys
865                 870                 875                 880
Gly Thr Thr Gly Ala Ala Ala Thr Gly Cys Thr Ala Ala Cys Gly Gly
                885                 890                 895
Cys Cys Ala Gly Thr Thr Gly Gly Thr Cys Ala Ala Ala Ala Ala Gly
            900                 905                 910
Ala Ala Ala Cys Thr Thr Cys Cys Ala Ala Ala Gly Thr Cys Gly
            915                 920                 925
Gly Cys Ala Thr Ala Cys Cys Gly Thr Thr Gly Thr Cys Thr Thr
            930                 935                 940
Gly Thr Thr Thr Gly Gly Thr Ala Thr Thr Gly Ala Thr Thr Gly Ala
945                 950                 955                 960
Cys Gly Ala Ala Thr Gly Cys Thr Cys Ala Ala Ala Ala Ala Thr Ala
                965                 970                 975
Ala Thr Cys Thr Cys Ala Thr Thr Ala Ala Thr Gly Cys Thr Thr Ala
            980                 985                 990
Gly Cys Gly Cys Ala Gly Thr Cys  Thr Cys Thr Cys Thr  Ala Thr Cys
            995                 1000                1005
Gly Cys  Thr Thr Cys Thr Gly Ala Ala Cys Cys Cys  Cys Gly Gly
            1010                1015                1020
Thr Gly  Cys Ala Cys Cys Thr  Gly Thr Gly Cys Cys  Gly Ala Ala
            1025                1030                1035
Ala Cys  Gly Cys Ala Ala Ala  Thr Gly Gly Gly  Ala Ala Ala
            1040                1045                1050
Cys Ala  Cys Cys Cys Gly Cys  Thr Thr Thr Thr  Gly Gly Ala
            1055                1060                1065
Thr Gly  Ala Thr Thr Ala Thr  Gly Cys Ala Thr Thr  Gly Thr Cys
            1070                1075                1080
Thr Cys  Cys Ala Cys Ala Thr  Gly Thr Ala Thr  Gly Cys Thr
            1085                1090                1095
Thr Cys  Cys Ala Ala Gly Ala  Thr Thr Cys Thr Gly  Gly Thr Gly
            1100                1105                1110
Gly Gly  Ala Ala Thr Ala Cys  Thr Gly Cys Thr Gly  Ala Thr Ala
            1115                1120                1125
Gly Cys  Cys Thr Ala Ala Cys  Gly Thr Thr Cys Ala  Thr Gly Ala
            1130                1135                1140
Thr Cys  Ala Ala Ala Ala Thr  Thr Thr Ala Ala Cys  Thr Gly Thr
            1145                1150                1155
Thr Cys  Thr Ala Ala Cys Cys  Cys Cys Thr Ala Cys  Thr Thr Gly
            1160                1165                1170
Ala Cys  Ala Gly Cys Ala Ala  Thr Ala Thr Ala Thr  Ala Ala Ala
            1175                1180                1185
Cys Ala  Gly Ala Ala Gly Gly  Ala Ala Gly Cys Thr  Gly Cys Cys
            1190                1195                1200
Cys Thr  Gly Thr Cys Thr Thr  Ala Ala Ala Cys Cys  Thr Thr Thr
            1205                1210                1215
```

Thr Thr Thr Thr Thr Thr Ala Thr Cys Ala Thr Cys Ala Thr Thr
        1220                1225                1230

Ala Thr Thr Ala Gly Cys Thr Thr Ala Cys Thr Thr Thr Cys Ala
        1235                1240                1245

Thr Ala Ala Thr Thr Gly Cys Gly Ala Cys Thr Gly Gly Thr Thr
        1250                1255                1260

Cys Cys Ala Ala Thr Thr Gly Ala Cys Ala Ala Gly Cys Thr Thr
        1265                1270                1275

Thr Thr Gly Ala Thr Thr Thr Thr Ala Ala Cys Gly Ala Cys Thr
        1280                1285                1290

Thr Thr Thr Ala Ala Cys Gly Ala Cys Ala Ala Cys Thr Thr Gly
        1295                1300                1305

Ala Gly Ala Ala Gly Ala Thr Cys Ala Ala Ala Ala Ala Ala Cys
        1310                1315                1320

Ala Ala Cys Thr Ala Ala Thr Thr Ala Thr Thr Cys Gly Ala Ala
        1325                1330                1335

Ala Cys Gly Gly Ala Ala Thr Thr Cys Ala Cys Gly Ala Thr Gly
        1340                1345                1350

Ala Gly Ala Thr Thr Thr Cys Cys Thr Thr Cys Ala Ala Thr Thr
        1355                1360                1365

Thr Thr Thr Ala Cys Thr Gly Cys Thr Gly Thr Thr Thr Thr Ala
        1370                1375                1380

Thr Thr Cys Gly Cys Ala Gly Cys Ala Thr Cys Cys Thr Cys Cys
        1385                1390                1395

Gly Cys Ala Thr Thr Ala Gly Cys Thr Gly Ala Cys Ala Ala Gly
        1400                1405                1410

Ala Cys Ala Cys Ala Thr Cys Thr Thr Gly Thr Cys Cys Cys Ala
        1415                1420                1425

Cys Cys Ala Thr Gly Thr Cys Cys Ala Gly Cys Thr Cys Cys Ala
        1430                1435                1440

Gly Ala Ala Thr Thr Gly Thr Thr Gly Gly Gly Thr Gly Gly Thr
        1445                1450                1455

Cys Cys Ala Thr Cys Cys Gly Thr Thr Thr Thr Cys Thr Thr Gly
        1460                1465                1470

Thr Thr Cys Cys Cys Ala Cys Ala Ala Ala Gly Cys Cys Ala
        1475                1480                1485

Ala Ala Gly Gly Ala Cys Ala Cys Thr Thr Gly Ala Thr Gly
        1490                1495                1500

Ala Thr Cys Thr Cys Cys Ala Gly Ala Ala Cys Thr Cys Cys Ala
        1505                1510                1515

Gly Ala Gly Gly Thr Thr Ala Cys Ala Thr Gly Thr Gly Thr Thr
        1520                1525                1530

Gly Thr Thr Gly Thr Thr Gly Ala Cys Gly Thr Thr Thr Cys Thr
        1535                1540                1545

Cys Ala Cys Gly Ala Gly Gly Ala Cys Cys Cys Ala Gly Ala Gly
        1550                1555                1560

Gly Thr Thr Ala Ala Gly Thr Thr Cys Ala Ala Cys Thr Gly Gly
        1565                1570                1575

Thr Ala Cys Gly Thr Thr Gly Ala Cys Gly Gly Thr Gly Thr Thr
        1580                1585                1590

Gly Ala Ala Gly Thr Thr Cys Ala Cys Ala Ala Cys Gly Cys Thr
        1595                1600                1605

Ala Ala Gly Ala Cys Thr Ala Ala Gly Cys Cys Ala Ala Gly Ala

-continued

```
            1610                1615                1620

Gly Ala  Ala Gly Ala Gly Cys  Ala Gly Thr Ala Cys  Ala Ala Cys
    1625                1630                1635

Thr Cys  Cys Ala Cys Thr Thr  Ala Cys Ala Gly Ala  Gly Thr Thr
    1640                1645                1650

Gly Thr  Thr Thr Cys Cys Gly  Thr Thr Thr Thr Gly  Ala Cys Thr
    1655                1660                1665

Gly Thr  Thr Thr Thr Gly Cys  Ala Cys Cys Ala Gly  Gly Ala Cys
    1670                1675                1680

Thr Gly  Gly Thr Thr Gly Ala  Ala Cys Gly Gly Thr  Ala Ala Ala
    1685                1690                1695

Gly Ala  Ala Thr Ala Cys Ala  Ala Gly Thr Gly Thr  Ala Ala Gly
    1700                1705                1710

Gly Thr  Thr Thr Cys Cys Ala  Ala Cys Ala Ala Gly  Gly Cys Thr
    1715                1720                1725

Thr Thr  Gly Cys Cys Ala Gly  Cys Thr Cys Cys Ala  Ala Thr Cys
    1730                1735                1740

Gly Ala  Ala Ala Ala Gly Ala  Cys Thr Ala Thr Cys  Thr Cys Cys
    1745                1750                1755

Ala Ala  Gly Gly Cys Thr Ala  Ala Gly Gly Gly Thr  Cys Ala Ala
    1760                1765                1770

Cys Cys  Ala Ala Gly Ala Gly  Ala Gly Cys Cys Ala  Cys Ala Gly
    1775                1780                1785

Gly Thr  Thr Thr Ala Cys Ala  Cys Thr Thr Thr Gly  Cys Cys Ala
    1790                1795                1800

Cys Cys  Ala Thr Cys Cys Ala  Gly Ala Gly Ala Ala  Gly Ala Gly
    1805                1810                1815

Ala Thr  Gly Ala Cys Thr Ala  Ala Gly Ala Ala Cys  Cys Ala Gly
    1820                1825                1830

Gly Thr  Thr Thr Cys Cys Thr  Thr Gly Ala Cys Thr  Thr Gly Thr
    1835                1840                1845

Thr Thr  Gly Gly Thr Thr Ala  Ala Ala Gly Gly Ala  Thr Thr Cys
    1850                1855                1860

Thr Ala  Cys Cys Cys Ala Thr  Cys Cys Gly Ala Cys  Ala Thr Thr
    1865                1870                1875

Gly Cys  Thr Gly Thr Thr Gly  Ala Gly Thr Gly Gly  Gly Ala Ala
    1880                1885                1890

Thr Cys  Thr Ala Ala Cys Gly  Gly Thr Cys Ala Ala  Cys Cys Ala
    1895                1900                1905

Gly Ala  Gly Ala Ala Cys Ala  Ala Cys Thr Ala Cys  Ala Ala Gly
    1910                1915                1920

Ala Cys  Thr Ala Cys Thr Cys  Cys Ala Cys Cys Ala  Gly Thr Thr
    1925                1930                1935

Thr Thr  Gly Gly Ala Thr Thr  Cys Thr Gly Ala Thr  Gly Gly Thr
    1940                1945                1950

Thr Cys  Cys Thr Thr Cys Thr  Thr Cys Thr Thr Gly  Thr Ala Cys
    1955                1960                1965

Thr Cys  Cys Ala Ala Gly Thr  Thr Gly Ala Cys Thr  Gly Thr Thr
    1970                1975                1980

Gly Ala  Cys Ala Ala Gly Thr  Cys Cys Ala Gly Ala  Thr Gly Gly
    1985                1990                1995

Cys Ala  Ala Cys Ala Gly Gly  Gly Thr Ala Ala Cys  Gly Thr Thr
    2000                2005                2010
```

```
Thr Thr Cys Thr Cys Cys Thr Gly Thr Thr Cys Cys Gly Thr Thr
    2015                2020                2025

Ala Thr Gly Cys Ala Thr Gly Ala Gly Gly Cys Thr Thr Thr Gly
    2030                2035                2040

Cys Ala Cys Ala Ala Cys Cys Ala Cys Thr Ala Cys Ala Cys Thr
    2045                2050                2055

Cys Ala Ala Ala Ala Gly Thr Cys Cys Thr Thr Gly Thr Cys Thr
    2060                2065                2070

Thr Thr Gly Thr Cys Cys Cys Cys Thr Gly Gly Thr Gly Gly Thr
    2075                2080                2085

Gly Gly Thr Gly Gly Thr Gly Thr Cys Gly Ala Cys Cys Ala Ala
    2090                2095                2100

Thr Thr Cys Thr Cys Thr Ala Ala Cys Thr Cys Thr Ala Cys Thr
    2105                2110                2115

Thr Cys Cys Gly Cys Thr Thr Cys Cys Thr Cys Thr Ala Cys Thr
    2120                2125                2130

Gly Ala Cys Gly Thr Thr Ala Cys Thr Thr Cys Cys Thr Cys Cys
    2135                2140                2145

Thr Cys Cys Thr Cys Thr Ala Thr Thr Thr Cys Thr Ala Cys Thr
    2150                2155                2160

Thr Cys Cys Thr Cys Cys Gly Gly Thr Thr Cys Cys Gly Thr Thr
    2165                2170                2175

Ala Cys Thr Ala Thr Thr Ala Cys Thr Thr Cys Cys Thr Cys Thr
    2180                2185                2190

Gly Ala Gly Gly Cys Thr Cys Cys Ala Gly Ala Ala Thr Cys Thr
    2195                2200                2205

Gly Ala Cys Ala Ala Cys Gly Gly Thr Ala Cys Thr Thr Cys Thr
    2210                2215                2220

Ala Cys Thr Gly Cys Thr Gly Cys Thr Cys Cys Ala Ala Cys Thr
    2225                2230                2235

Gly Ala Ala Ala Cys Thr Thr Cys Thr Ala Cys Thr Gly Ala Gly
    2240                2245                2250

Gly Cys Thr Cys Cys Thr Ala Cys Thr Ala Cys Thr Gly Cys Thr
    2255                2260                2265

Ala Thr Thr Cys Cys Ala Ala Cys Thr Ala Ala Cys Gly Gly Ala
    2270                2275                2280

Ala Cys Thr Thr Cys Cys Ala Cys Ala Gly Ala Gly Gly Cys Thr
    2285                2290                2295

Cys Cys Ala Ala Cys Ala Ala Cys Ala Gly Cys Thr Ala Thr Cys
    2300                2305                2310

Cys Cys Thr Ala Cys Ala Ala Ala Cys Gly Gly Thr Ala Cys Ala
    2315                2320                2325

Thr Cys Cys Ala Cys Thr Gly Ala Ala Gly Cys Thr Cys Cys Thr
    2330                2335                2340

Ala Cys Thr Gly Ala Cys Ala Cys Thr Ala Cys Thr Ala Cys Ala
    2345                2350                2355

Gly Ala Ala Gly Cys Thr Cys Cys Ala Ala Cys Thr Ala Cys Thr
    2360                2365                2370

Gly Cys Thr Thr Thr Gly Cys Cys Thr Ala Cys Thr Ala Ala Thr
    2375                2380                2385

Gly Gly Thr Ala Cys Ala Thr Cys Ala Ala Cys Ala Gly Ala Gly
    2390                2395                2400
```

-continued

```
Gly Cys  Thr Cys Cys Thr Ala  Cys Ala Gly Ala Thr  Ala Cys Ala
    2405                 2410                 2415

Ala Cys  Ala Ala Cys Thr Gly  Ala Ala Gly Cys Thr  Cys Cys Ala
    2420                 2425                 2430

Ala Cys  Ala Ala Cys Thr Gly  Gly Ala Thr Thr Gly  Cys Cys Ala
    2435                 2440                 2445

Ala Cys  Ala Ala Ala Cys Gly  Gly Thr Ala Cys Thr  Ala Cys Thr
    2450                 2455                 2460

Thr Cys  Thr Gly Cys Thr Thr  Thr Cys Cys Cys Ala  Cys Cys Ala
    2465                 2470                 2475

Ala Cys  Thr Ala Cys Thr Thr  Cys Cys Thr Thr Gly  Cys Cys Ala
    2480                 2485                 2490

Cys Cys  Ala Thr Cys Cys Ala  Ala Cys Ala Cys Thr  Ala Cys Thr
    2495                 2500                 2505

Ala Cys  Thr Ala Cys Thr Cys  Cys Ala Cys Cys Ala  Thr Ala Cys
    2510                 2515                 2520

Ala Ala  Cys Cys Cys Ala Thr  Cys Cys Ala Cys Thr  Gly Ala Cys
    2525                 2530                 2535

Thr Ala  Cys Ala Cys Thr Ala  Cys Thr Gly Ala Cys  Thr Ala Cys
    2540                 2545                 2550

Ala Cys  Ala Gly Thr Thr Gly  Thr Thr Ala Cys Thr  Gly Ala Gly
    2555                 2560                 2565

Thr Ala  Cys Ala Cys Thr Ala  Cys Thr Thr Ala Cys  Thr Gly Thr
    2570                 2575                 2580

Cys Cys  Ala Gly Ala Gly Cys  Cys Ala Ala Cys Thr  Ala Cys Thr
    2585                 2590                 2595

Thr Thr  Cys Ala Cys Ala Ala  Cys Ala Ala Ala Cys  Gly Gly Ala
    2600                 2605                 2610

Ala Ala  Gly Ala Cys Thr Thr  Ala Cys Ala Cys Thr  Gly Thr Thr
    2615                 2620                 2625

Ala Cys  Thr Gly Ala Gly Cys  Cys Thr Ala Cys Thr  Ala Cys Thr
    2630                 2635                 2640

Thr Thr  Gly Ala Cys Thr Ala  Thr Cys Ala Cys Thr  Gly Ala Cys
    2645                 2650                 2655

Thr Gly  Thr Cys Cys Ala Thr  Gly Thr Ala Cys Thr  Ala Thr Cys
    2660                 2665                 2670

Gly Ala  Gly Ala Ala Gly Cys  Cys Ala Ala Cys Thr  Ala Cys Thr
    2675                 2680                 2685

Ala Cys  Thr Thr Cys Cys Ala  Cys Thr Ala Cys Ala  Gly Ala Gly
    2690                 2695                 2700

Thr Ala  Thr Ala Cys Thr Gly  Thr Thr Gly Thr Thr  Ala Cys Ala
    2705                 2710                 2715

Gly Ala  Ala Thr Ala Cys Ala  Cys Ala Ala Cys Ala  Thr Ala Thr
    2720                 2725                 2730

Thr Gly  Thr Cys Cys Thr Gly  Ala Gly Cys Cys Ala  Ala Cys Ala
    2735                 2740                 2745

Ala Cys  Ala Thr Thr Cys Ala  Cys Thr Ala Cys Thr  Ala Ala Thr
    2750                 2755                 2760

Gly Gly  Ala Ala Ala Ala Ala  Cys Ala Thr Ala Cys  Ala Cys Ala
    2765                 2770                 2775

Gly Thr  Thr Ala Cys Ala Gly  Ala Ala Cys Cys Ala  Ala Cys Thr
    2780                 2785                 2790

Ala Cys  Ala Thr Thr Gly Ala  Cys Ala Ala Thr Thr  Ala Cys Ala
```

-continued

```
              2795                2800                2805

Gly Ala Thr Thr Gly Thr Cys Cys Thr Gly Thr Ala Cys Ala
         2810                2815                2820

Ala Thr Thr Gly Ala Gly Ala Ala Gly Thr Cys Cys Gly Ala Gly
         2825                2830                2835

Gly Cys Thr Cys Cys Thr Gly Ala Ala Thr Cys Thr Thr Cys Thr
         2840                2845                2850

Gly Thr Thr Cys Cys Ala Gly Thr Thr Ala Cys Thr Gly Ala Ala
         2855                2860                2865

Thr Cys Cys Ala Ala Gly Gly Thr Ala Cys Thr Ala Cys Thr
         2870                2875                2880

Ala Cys Thr Ala Ala Ala Gly Ala Ala Cys Thr Gly Gly Thr
         2885                2890                2895

Gly Thr Thr Ala Cys Thr Ala Cys Thr Ala Ala Gly Cys Ala Gly
         2900                2905                2910

Ala Cys Thr Ala Cys Thr Gly Cys Thr Ala Ala Cys Cys Cys Ala
         2915                2920                2925

Thr Cys Cys Thr Thr Gly Ala Cys Thr Gly Thr Thr Cys Cys
         2930                2935                2940

Ala Cys Thr Gly Thr Thr Gly Thr Thr Cys Cys Ala Gly Thr Thr
         2945                2950                2955

Thr Cys Thr Thr Cys Cys Thr Cys Thr Gly Cys Thr Thr Cys Thr
         2960                2965                2970

Thr Cys Cys Cys Ala Cys Thr Cys Cys Gly Thr Thr Gly Thr Thr
         2975                2980                2985

Ala Thr Cys Ala Ala Cys Thr Cys Cys Ala Ala Cys Gly Gly Thr
         2990                2995                3000

Gly Cys Thr Ala Ala Cys Gly Thr Thr Gly Thr Thr Gly Thr Thr
         3005                3010                3015

Cys Cys Thr Gly Gly Thr Gly Cys Thr Thr Thr Gly Gly Gly Ala
         3020                3025                3030

Thr Thr Gly Gly Cys Thr Gly Thr Gly Thr Thr Gly Cys Thr
         3035                3040                3045

Ala Thr Gly Thr Thr Gly Thr Thr Cys Thr Thr Gly Thr Ala Ala
         3050                3055                3060

Thr Ala Gly Gly Gly Cys Cys Gly Gly Cys Cys Ala Thr Thr Thr
         3065                3070                3075

Ala Ala Ala Thr Ala Cys Ala Gly Gly Cys Cys Cys Thr Thr
         3080                3085                3090

Thr Thr Cys Cys Thr Thr Thr Gly Thr Cys Gly Ala Thr Ala Thr
         3095                3100                3105

Cys Ala Thr Gly Thr Ala Ala Thr Thr Ala Gly Thr Thr Ala Thr
         3110                3115                3120

Gly Thr Cys Ala Cys Gly Cys Thr Thr Ala Cys Ala Thr Thr Cys
         3125                3130                3135

Ala Cys Gly Cys Cys Cys Thr Cys Cys Cys Cys Cys Ala Cys
         3140                3145                3150

Ala Thr Cys Cys Gly Cys Thr Cys Thr Ala Ala Cys Cys Gly Ala
         3155                3160                3165

Ala Ala Ala Gly Gly Ala Ala Gly Gly Ala Gly Thr Thr Ala Gly
         3170                3175                3180

Ala Cys Ala Ala Cys Cys Thr Gly Ala Ala Gly Thr Cys Thr Ala
         3185                3190                3195
```

```
Gly Gly Thr Cys Cys Cys Thr Ala Thr Thr Ala Thr Thr Thr
        3200                3205                3210

Thr Thr Thr Thr Thr Ala Ala Thr Ala Gly Thr Thr Ala Thr Gly
        3215                3220                3225

Thr Thr Ala Gly Thr Ala Thr Thr Ala Ala Gly Ala Ala Cys Gly
        3230                3235                3240

Thr Thr Ala Thr Thr Thr Ala Thr Ala Thr Thr Thr Cys Ala Ala
        3245                3250                3255

Ala Thr Thr Thr Thr Thr Cys Thr Thr Thr Thr Thr Thr Thr Thr
        3260                3265                3270

Cys Thr Gly Thr Ala Cys Ala Ala Ala Cys Gly Cys Gly Thr Gly
        3275                3280                3285

Thr Ala Cys Gly Cys Ala Thr Gly Thr Ala Ala Cys Ala Thr Thr
        3290                3295                3300

Ala Thr Ala Cys Thr Gly Ala Ala Ala Ala Cys Cys Thr Thr Gly
        3305                3310                3315

Cys Thr Thr Gly Ala Gly Ala Ala Gly Gly Thr Thr Thr Thr Gly
        3320                3325                3330

Gly Gly Ala Cys Gly Cys Thr Cys Gly Ala Ala Gly Gly Cys Thr
        3335                3340                3345

Thr Thr Ala Ala Thr Thr Thr Gly Cys Ala Ala Gly Cys Thr Gly
        3350                3355                3360

Gly Ala Thr Cys Cys Gly Cys Gly Gly Cys Cys Gly Cys Thr Thr
        3365                3370                3375

Ala Cys Gly Cys Gly Cys Cys Gly Thr Thr Cys Thr Thr Cys Gly
        3380                3385                3390

Cys Thr Thr Gly Gly Thr Cys Thr Thr Gly Thr Ala Thr Cys Thr
        3395                3400                3405

Cys Cys Thr Thr Ala Cys Ala Cys Thr Gly Thr Ala Thr Cys Thr
        3410                3415                3420

Thr Cys Cys Cys Ala Thr Thr Thr Gly Cys Gly Thr Thr Thr Ala
        3425                3430                3435

Gly Gly Thr Gly Gly Thr Thr Ala Thr Cys Ala Ala Ala Ala Ala
        3440                3445                3450

Cys Thr Ala Ala Ala Ala Gly Gly Ala Ala Ala Ala Thr Thr
        3455                3460                3465

Thr Cys Ala Gly Ala Thr Gly Thr Thr Thr Ala Thr Cys Thr Cys
        3470                3475                3480

Thr Ala Ala Gly Gly Thr Thr Thr Thr Thr Thr Cys Thr Thr Thr
        3485                3490                3495

Thr Thr Ala Cys Ala Gly Thr Ala Thr Ala Cys Ala Cys Gly
        3500                3505                3510

Thr Gly Ala Thr Gly Cys Gly Thr Cys Ala Cys Gly Thr Gly Gly
        3515                3520                3525

Thr Ala Cys Thr Ala Gly Ala Thr Thr Ala Cys Gly Thr Ala Ala
        3530                3535                3540

Gly Thr Thr Ala Thr Thr Thr Gly Gly Thr Cys Cys Gly Gly
        3545                3550                3555

Thr Gly Gly Gly Thr Ala Ala Gly Thr Gly Gly Gly Thr Ala Ala
        3560                3565                3570

Gly Ala Ala Thr Ala Gly Ala Ala Ala Gly Cys Ala Thr Gly Ala
        3575                3580                3585
```

-continued

Ala Gly Gly Thr Thr Thr Ala Cys Ala Ala Ala Ala Ala Cys Gly
3590 3595 3600

Cys Ala Gly Thr Cys Ala Cys Gly Ala Ala Thr Thr Ala Thr Thr
3605 3610 3615

Gly Cys Thr Ala Cys Thr Thr Cys Gly Ala Gly Cys Thr Thr Gly
3620 3625 3630

Gly Ala Ala Cys Cys Ala Cys Cys Cys Cys Ala Ala Ala Gly Ala
3635 3640 3645

Thr Thr Ala Thr Ala Thr Thr Gly Thr Ala Cys Thr Gly Ala Thr
3650 3655 3660

Gly Cys Ala Cys Thr Ala Cys Cys Thr Thr Cys Thr Cys Gly Ala
3665 3670 3675

Thr Thr Thr Thr Gly Cys Thr Cys Cys Thr Cys Cys Ala Ala Gly
3680 3685 3690

Ala Ala Cys Cys Thr Ala Cys Gly Ala Ala Ala Ala Ala Cys Ala
3695 3700 3705

Thr Thr Thr Cys Thr Thr Gly Ala Gly Cys Cys Thr Thr Thr Thr
3710 3715 3720

Cys Ala Ala Cys Cys Thr Ala Gly Ala Cys Thr Ala Cys Ala Cys
3725 3730 3735

Ala Thr Cys Ala Ala Gly Thr Thr Ala Thr Thr Thr Ala Ala Gly
3740 3745 3750

Gly Thr Ala Thr Gly Thr Thr Cys Cys Gly Thr Thr Ala Ala Cys
3755 3760 3765

Ala Thr Gly Thr Ala Ala Gly Ala Ala Ala Ala Gly Gly Ala Gly
3770 3775 3780

Ala Gly Gly Ala Thr Ala Gly Ala Thr Cys Gly Thr Thr Thr Ala
3785 3790 3795

Thr Gly Gly Gly Gly Thr Ala Cys Gly Thr Cys Gly Cys Cys Thr
3800 3805 3810

Gly Ala Thr Thr Cys Ala Ala Gly Cys Gly Thr Gly Ala Cys Cys
3815 3820 3825

Ala Thr Thr Cys Gly Ala Ala Gly Ala Ala Thr Ala Gly Gly Cys
3830 3835 3840

Cys Thr Thr Cys Gly Ala Ala Ala Gly Cys Thr Gly Ala Ala Thr
3845 3850 3855

Ala Ala Ala Gly Cys Ala Ala Ala Thr Gly Thr Cys Ala Gly Thr
3860 3865 3870

Thr Gly Cys Gly Ala Thr Thr Gly Gly Thr Ala Thr Gly Cys Thr
3875 3880 3885

Gly Ala Cys Ala Ala Ala Thr Thr Ala Gly Cys Ala Thr Ala Ala
3890 3895 3900

Ala Ala Ala Gly Cys Ala Ala Thr Ala Gly Ala Cys Thr Thr Thr
3905 3910 3915

Cys Thr Ala Ala Cys Cys Ala Cys Cys Thr Gly Thr Thr Thr Thr
3920 3925 3930

Thr Thr Thr Cys Cys Thr Thr Thr Thr Ala Cys Thr Thr Thr Ala
3935 3940 3945

Thr Thr Thr Ala Thr Ala Thr Thr Thr Thr Gly Cys Cys Ala Cys
3950 3955 3960

Cys Gly Thr Ala Cys Thr Ala Ala Cys Ala Ala Gly Thr Thr Cys
3965 3970 3975

Ala Gly Ala Cys Ala Ala Ala Thr Thr Ala Ala Thr Thr Ala Ala

-continued

```
            3980              3985              3990

Cys Ala Cys Cys Ala Thr Gly Thr Cys Ala Gly Ala  Ala Gly Ala
        3995              4000              4005

Thr Cys Ala Ala Ala Ala Ala Gly Thr Gly Ala  Ala Ala Ala
        4010              4015              4020

Thr Thr Cys Cys Gly Thr Ala Cys Cys Thr Thr Cys  Thr Ala Ala
        4025              4030              4035

Gly Gly Thr Thr Ala Ala Thr Ala Thr Gly Gly Thr  Gly Ala Ala
        4040              4045              4050

Thr Cys Gly Cys Ala Cys Cys Gly Ala Thr Ala Thr  Ala Cys Thr
        4055              4060              4065

Gly Ala Cys Thr Ala Cys Gly Ala Thr Cys Ala Ala  Gly Thr Cys
        4070              4075              4080

Ala Thr Thr Gly Thr Cys Ala Thr Gly Gly Cys Thr  Thr Gly Ala
        4085              4090              4095

Cys Thr Thr Gly Ala Thr Gly Thr Thr Gly Cys Cys  Ala Thr Thr
        4100              4105              4110

Thr Ala Cys Thr Ala Thr Ala Ala Thr Thr Cys Thr  Cys Thr Cys
        4115              4120              4125

Cys Ala Thr Ala Ala Thr Cys Ala Thr Thr Gly Cys  Ala Gly Thr
        4130              4135              4140

Ala Ala Thr Ala Ala Thr Thr Thr Cys Thr Gly Thr  Cys Thr Ala
        4145              4150              4155

Thr Gly Thr Gly Cys Cys Thr Cys Thr Thr Cys  Cys Cys Gly
        4160              4165              4170

Thr Cys Ala Cys Ala Cys Thr Thr Thr Gly Ala Cys  Gly Cys
        4175              4180              4185

Thr Gly Ala Ala Gly Gly Thr Cys Ala Thr Cys Cys  Cys Ala Ala
        4190              4195              4200

Thr Cys Thr Ala Ala Thr Gly Gly Gly Ala Gly Thr  Gly Thr Cys
        4205              4210              4215

Cys Ala Thr Thr Cys Cys Thr Thr Thr Gly Ala Cys  Thr Gly Thr
        4220              4225              4230

Thr Gly Gly Thr Ala Thr Gly Ala Thr Thr Gly Thr  Ala Ala Thr
        4235              4240              4245

Gly Ala Thr Gly Ala Thr Thr Cys Cys Cys Cys Cys  Gly Ala Thr
        4250              4255              4260

Cys Thr Gly Cys Ala Ala Ala Gly Thr Thr Thr Cys  Cys Thr Gly
        4265              4270              4275

Gly Gly Ala Gly Thr Cys Thr Ala Thr Thr Cys Ala  Cys Ala Ala
        4280              4285              4290

Gly Thr Ala Cys Thr Thr Cys Thr Ala Cys Ala  Gly Gly Ala Gly
        4295              4300              4305

Cys Thr Ala Thr Ala Thr Ala Ala Gly Gly Ala Ala  Gly Cys Ala
        4310              4315              4320

Ala

Gly Thr Gly Gly Ala Thr Gly Cys Gly Cys Thr Ala Thr Thr
4385            4390            4395

Cys Gly Ala Thr Thr Ala Thr Ala Ala Gly Gly Ala Ala Thr Ala
4400            4405            4410

Cys Cys Gly Thr Cys Ala Ala Gly Gly Cys Ala Thr Thr Ala Thr
4415            4420            4425

Thr Ala Thr Gly Ala Thr Cys Gly Gly Ala Gly Thr Ala Gly Cys
4430            4435            4440

Thr Ala Gly Ala Thr Gly Cys Ala Thr Thr Gly Cys Cys Ala Thr
4445            4450            4455

Gly Gly Thr Gly Cys Thr Ala Ala Thr Thr Thr Gly Gly Ala Ala
4460            4465            4470

Thr Cys Ala Gly Ala Thr Thr Gly Cys Thr Gly Gly Ala Gly Gly
4475            4480            4485

Ala Gly Ala Cys Ala Ala Thr Gly Ala Thr Cys Thr Cys Thr Gly
4490            4495            4500

Cys Gly Thr Cys Gly Thr Gly Cys Thr Thr Gly Thr Thr Ala Thr
4505            4510            4515

Thr Ala Cys Ala Ala Ala Cys Thr Cys Gly Cys Thr Thr Thr Thr
4520 4525 4530

Ala Cys Ala Gly Ala Thr Gly Gly Thr Ala Thr Thr Ala Thr Ala
4535 4540 4545

Thr Gly Cys Ala Cys Cys Ala Thr Thr Gly Cys Ala Gly Ala Thr
4550 4555 4560

Ala Thr Thr Thr Thr Ala Cys Thr Gly Thr Thr Ala Thr Gly Thr
4565 4570 4575

Thr Ala Thr Thr Thr Cys Thr Cys Ala Thr Gly Ala Cys Cys Ala
4580 4585 4590

Cys Cys Thr Gly Ala Ala Thr Ala Cys Thr Thr Cys Ala Ala Ala
4595 4600 4605

Thr Ala Gly Gly Gly Thr Ala Thr Thr Ala Thr Thr Cys Gly Ala
4610 4615 4620

Ala Gly Ala Gly Gly Thr Thr Gly Cys Ala Ala Ala Gly Thr Cys
4625 4630 4635

Thr Gly Thr Cys Gly Gly Ala Gly Thr Thr Thr Thr Thr Cys Thr
4640 4645 4650

Cys Gly Gly Cys Ala Thr Ala Cys Cys Ala Cys Thr Gly Gly Gly
4655 4660 4665

Ala Ala Thr Thr Gly Gly Cys Ala Thr Thr Ala Thr Cys Ala Thr
4670 4675 4680

Ala Cys Gly Thr Thr Thr Gly Gly Gly Ala Ala Gly Thr Cys Thr
4685 4690 4695

Thr Ala Cys Cys Ala Thr Ala Gly Cys Thr Gly Gly Thr Ala Ala
4700 4705 4710

Ala Ala Gly Thr Ala Ala Thr Thr Ala Thr Gly Ala Ala Ala Ala
4715 4720 4725

Ala Thr Ala Cys Ala Thr Thr Thr Thr Gly Ala Gly Ala Thr Thr
4730 4735 4740

Thr Ala Thr Thr Thr Cys Thr Cys Cys Ala Thr Gly Gly Gly Cys
4745 4750 4755

Ala Ala Thr Gly Ala Thr Cys Gly Gly Ala Thr Thr Thr Cys Ala
4760 4765 4770

```
Thr Thr Ala Cys Ala Cys Thr Thr Ala Thr Thr Thr Gly Thr
4775             4780                4785

Thr Ala Thr Thr Thr Thr Thr Ala Thr Ala Gly Thr Ala Gly
4790             4795                4800

Ala Gly Gly Thr Thr Ala Thr Cys Ala Ala Thr Thr Ala Thr
4805             4810                4815

Cys Cys Ala Cys Gly Ala Ala Ala Thr Gly Gly Thr Thr Cys
4820             4825                4830

Thr Gly Cys Ala Ala Thr Ala Thr Thr Gly Thr Gly Cys Thr Thr
4835             4840                4845

Thr Gly Thr Cys Cys Cys Ala Thr Thr Gly Gly Thr Gly Cys Thr
4850             4855                4860

Thr Thr Ala Cys Thr Thr Cys Thr Thr Thr Ala Thr Thr Gly Cys
4865             4870                4875

Ala Thr Gly Gly Thr Thr Thr Thr Thr Gly Ala Cys Cys Thr Thr
4880             4885                4890

Cys Gly Cys Ala Thr Thr Ala Ala Thr Gly Ala Gly Gly Thr Ala
4895             4900                4905

Cys Thr Thr Ala Thr Cys Ala Ala Thr Ala Thr Cys Thr Ala Gly
4910             4915                4920

Gly Ala Gly Thr Gly Ala Thr Ala Cys Ala Cys Ala Ala Ala Gly
4925             4930                4935

Ala Gly Ala Ala Thr Gly Thr Ala Gly Cys Thr Gly Thr Gly Ala
4940             4945                4950

Cys Cys Ala Ala Gly Ala Ala Cys Thr Ala Cys Thr Thr Thr Thr
4955             4960                4965

Ala Ala Ala Gly Ala Gly Gly Gly Thr Cys Thr Gly Gly Gly Gly
4970             4975                4980

Ala Ala Gly Ala Ala Ala Gly Thr Cys Thr Thr Gly Thr Gly Ala
4985             4990                4995

Ala Gly Cys Thr Ala Gly Cys Thr Thr Thr Thr Cys Thr Ala Thr
5000             5005                5010

Thr Ala Cys Gly Ala Thr Gly Ala Cys Gly Cys Ala Ala Thr Gly
5015             5020                5025

Thr Thr Thr Cys Ala Cys Thr Ala Thr Gly Gly Cys Thr Thr Cys
5030             5035                5040

Ala Ala Ala Thr Ala Ala Thr Thr Thr Thr Gly Ala Ala Cys Thr
5045             5050                5055

Ala Thr Cys Cys Cys Thr Gly Gly Cys Ala Ala Thr Thr Gly Cys
5060             5065                5070

Thr Ala Thr Thr Thr Cys Cys Thr Thr Ala Thr Ala Thr Gly Gly
5075             5080                5085

Thr Ala Ala Cys Ala Ala Thr Ala Gly Cys Ala Ala Gly Cys Ala
5090             5095                5100

Ala Gly Cys Ala Ala Thr Ala Gly Cys Thr Gly Cys Ala Ala Cys
5105             5110                5115

Ala Thr Thr Thr Gly Gly Gly Cys Cys Gly Thr Thr Gly Cys Thr
5120             5125                5130

Ala Gly Ala Ala Gly Thr Thr Cys Cys Ala Ala Thr Thr Thr Thr
5135             5140                5145

Ala Thr Thr Gly Ala Thr Thr Thr Thr Gly Gly Cys Ala Ala Thr
5150             5155                5160

Ala Gly Thr Cys Gly Cys Gly Ala Gly Ala Ala Thr Cys Cys Thr
```

```
                  5165                5170                5175

Thr Ala Ala Ala Cys Cys Ala Thr Ala Thr Ala  Thr Ala Thr
    5180                5185                5190

Ala Thr Gly Gly Ala Ala Cys Ala Ala Thr Ala Gly  Ala Ala Ala
    5195                5200                5205

Thr Thr Ala Ala Thr Thr Ala Ala Cys Ala Gly Gly  Cys Cys Cys
    5210                5215                5220

Cys Thr Thr Thr Thr Cys Cys Thr Thr Thr Gly Thr  Cys Gly Ala
    5225                5230                5235

Thr Ala Thr Cys Ala Thr Gly Thr Ala Ala Thr Thr  Ala Gly Thr
    5240                5245                5250

Thr Ala Thr Gly Thr Cys Ala Cys Gly Cys Thr Thr  Ala Cys Ala
    5255                5260                5265

Thr Thr Cys Ala Cys Gly Cys Cys Cys Thr Cys Cys  Thr Cys Cys
    5270                5275                5280

Cys Ala Cys Ala Thr Cys Cys Gly Cys Thr Cys Thr  Ala Ala Cys
    5285                5290                5295

Cys Gly Ala Ala Ala Ala Gly Gly Ala Ala Gly Gly  Ala Gly Thr
    5300                5305                5310

Thr Ala Gly Ala Cys Ala Ala Cys Cys Thr Gly Ala  Ala Gly Thr
    5315                5320                5325

Cys Thr Ala Gly Gly Thr Cys Cys Cys Thr Ala Thr  Thr Thr Ala
    5330                5335                5340

Thr Thr Thr Thr Thr Thr Thr Ala Ala Thr Ala  Gly Thr Thr
    5345                5350                5355

Ala Thr Gly Thr Thr Ala Gly Thr Ala Thr Thr Ala  Ala Gly Ala
    5360                5365                5370

Ala Cys Gly Thr Thr Ala Thr Thr Thr Ala Thr Ala  Thr Thr Thr
    5375                5380                5385

Cys Ala Ala Ala Thr Thr Thr Thr Cys Thr Thr Thr  Thr Thr Thr
    5390                5395                5400

Thr Thr Thr Cys Thr Gly Thr Ala Cys Ala Ala Ala  Cys Gly Cys
    5405                5410                5415

Gly Thr Gly Thr Ala Cys Gly Cys Ala Thr Gly Thr  Ala Ala Cys
    5420                5425                5430

Ala Thr Thr Ala Thr Ala Cys Thr Gly Ala Ala Ala  Ala Cys Cys
    5435                5440                5445

Thr Thr Gly Cys Thr Thr Gly Ala Gly Ala Ala Gly  Gly Thr Thr
    5450                5455                5460

Thr Thr Gly Gly Gly Ala Cys Gly Cys Thr Cys Gly  Ala Ala Gly
    5465                5470                5475

Gly Cys Thr Thr Thr Ala Ala Thr Thr Thr Gly Cys  Ala Ala Gly
    5480                5485                5490

Cys Thr Gly Cys Gly Gly Cys Thr Ala Ala Gly  Gly Cys Gly
    5495                5500                5505

Cys Gly Cys Cys Ala Gly Gly Cys Cys Ala Thr Ala  Ala Thr Gly
    5510                5515                5520

Gly Cys Cys Cys Ala Ala Ala Thr Gly Cys Ala Ala  Gly Ala Gly
    5525                5530                5535

Gly Ala Cys Ala Thr Thr Ala Gly Ala Ala Ala Thr  Gly Thr Gly
    5540                5545                5550

Thr Thr Thr Gly Gly Thr Ala Ala Gly Ala Ala Cys  Ala Thr Gly
    5555                5560                5565
```

```
Ala Ala Gly Cys Cys Gly Gly Ala Gly Cys Ala Thr Ala Cys
5570            5575            5580

Ala Ala Ala Cys Gly Ala Thr Thr Cys Ala Cys Ala Gly Ala Thr
5585            5590            5595

Thr Thr Gly Ala Ala Gly Gly Ala Gly Gly Ala Ala Ala Ala Cys
5600            5605            5610

Ala Ala Ala Cys Thr Gly Cys Ala Thr Cys Cys Ala Cys Cys Gly
5615            5620            5625

Gly Ala Ala Gly Thr Gly Cys Cys Ala Gly Cys Ala Gly Cys Cys
5630            5635            5640

Gly Thr Gly Thr Ala Thr Gly Cys Cys Ala Ala Cys Cys Thr Thr
5645            5650            5655

Gly Cys Thr Cys Thr Cys Ala Ala Ala Gly Gly Cys Ala Thr Thr
5660            5665            5670

Cys Cys Thr Ala Cys Gly Gly Ala Thr Cys Thr Gly Ala Gly Thr
5675            5680            5685

Gly Gly Gly Ala Ala Ala Thr Ala Thr Cys Thr Gly Ala Gly Ala
5690            5695            5700

Thr Thr Cys Ala Cys Ala Gly Ala Cys Cys Cys Ala Cys Thr Ala
5705            5710            5715

Thr Thr Gly Gly Ala Ala Cys Ala Gly Thr Ala Cys Cys Ala Ala
5720            5725            5730

Ala Cys Cys Thr Ala Gly Thr Thr Thr Gly Gly Cys Cys Gly Ala
5735            5740            5745

Thr Cys Cys Ala Thr Gly Ala Thr Thr Ala Thr Gly Thr Ala Ala
5750            5755            5760

Thr Gly Cys Ala Thr Ala Thr Ala Gly Thr Thr Thr Thr Thr Gly
5765            5770            5775

Thr Cys Gly Ala Thr Gly Cys Thr Cys Ala Cys Cys Cys Gly Thr
5780            5785            5790

Thr Thr Cys Gly Ala Gly Thr Cys Thr Gly Thr Cys Thr Cys Gly
5795            5800            5805

Thr Ala Thr Cys Gly Thr Cys Thr Thr Ala Cys Gly Thr Ala Thr
5810            5815            5820

Ala Ala Gly Thr Thr Cys Ala Ala Gly Cys Ala Thr Gly Thr Thr
5825            5830            5835

Thr Ala Cys Cys Ala Gly Gly Thr Cys Thr Gly Thr Thr Ala Gly
5840            5845            5850

Ala Ala Ala Cys Thr Cys Cys Thr Thr Thr Gly Thr Gly Ala Gly
5855            5860            5865

Gly Gly Cys Ala Gly Gly Ala Cys Cys Thr Ala Thr Thr Cys Gly
5870            5875            5880

Thr Cys Thr Cys Gly Gly Thr Cys Cys Cys Gly Thr Thr Gly Thr
5885            5890            5895

Thr Thr Cys Thr Ala Ala Gly Ala Gly Ala Cys Thr Gly Thr Ala
5900            5905            5910

Cys Ala Gly Cys Cys Ala Ala Gly Cys Gly Cys Ala Gly Ala Ala
5915            5920            5925

Thr Gly Gly Thr Gly Gly Cys Ala Thr Ala Ala Cys Cys Ala
5930            5935            5940

Thr Ala Ala Gly Ala Gly Gly Ala Thr Thr Cys Thr Gly Ala Thr
5945            5950            5955
```

Cys Gly Gly Ala Cys Thr Thr Gly Gly Thr Cys Thr Ala Thr Thr
5960            5965                 5970

Gly Gly Cys Thr Ala Thr Thr Gly Gly Ala Ala Cys Cys Ala Cys
5975            5980                 5985

Cys Cys Thr Thr Thr Ala Cys Gly Gly Gly Ala Cys Ala Ala Cys
5990            5995                 6000

Cys Ala Ala Cys Cys Cys Thr Ala Cys Cys Ala Ala Gly Ala Cys
6005            6010                 6015

Thr Cys Cys Thr Ala Thr Thr Gly Cys Ala Thr Thr Thr Gly Thr
6020            6025                 6030

Gly Gly Ala Ala Cys Cys Ala Gly Cys Cys Ala Cys Gly Gly Ala
6035            6040                 6045

Ala Ala Gly Ala Gly Cys Gly Thr Thr Thr Ala Ala Gly Gly Ala
6050            6055                 6060

Cys Gly Gly Ala Gly Ala Cys Gly Thr Cys Thr Cys Thr Gly Thr
6065            6070                 6075

Gly Ala Thr Thr Thr Thr Thr Gly Thr Thr Cys Thr Cys Gly Gly
6080            6085                 6090

Ala Gly Gly Thr Cys Cys Ala Gly Gly Ala Gly Cys Thr Gly Gly
6095            6100                 6105

Ala Ala Ala Ala Gly Gly Thr Ala Cys Cys Ala Ala Thr Gly
6110            6115                 6120

Thr Gly Cys Cys Ala Ala Ala Cys Thr Ala Gly Thr Gly Ala Gly
6125            6130                 6135

Thr Ala Ala Thr Thr Ala Cys Gly Gly Ala Thr Thr Gly Thr
6140            6145                 6150

Thr Cys Ala Cys Cys Thr Gly Thr Cys Ala Gly Cys Thr Gly Gly
6155            6160                 6165

Ala Gly Ala Cys Thr Thr Gly Thr Thr Ala Cys Gly Thr Gly Cys
6170            6175                 6180

Ala Gly Ala Ala Cys Ala Gly Ala Ala Gly Ala Gly Gly Gly Ala
6185            6190                 6195

Gly Gly Gly Gly Thr Cys Thr Ala Ala Gly Thr Ala Thr Gly Gly
6200            6205                 6210

Ala Gly Ala Gly Ala Thr Gly Ala Thr Thr Thr Cys Cys Cys Ala
6215            6220                 6225

Gly Thr Ala Thr Ala Thr Cys Ala Gly Ala Gly Ala Thr Gly Gly
6230            6235                 6240

Ala Cys Thr Gly Ala Thr Ala Gly Thr Ala Cys Cys Thr Cys Ala
6245            6250                 6255

Ala Gly Ala Gly Gly Thr Cys Ala Cys Cys Ala Thr Thr Gly Cys
6260            6265                 6270

Gly Cys Thr Cys Thr Thr Gly Gly Ala Gly Cys Ala Gly Gly Cys
6275            6280                 6285

Cys Ala Thr Gly Ala Ala Gly Gly Ala Ala Ala Ala Cys Thr Thr
6290            6295                 6300

Cys Gly Ala Gly Ala Ala Ala Gly Gly Gly Ala Ala Gly Ala Cys
6305            6310                 6315

Ala Cys Gly Gly Thr Thr Cys Thr Thr Gly Ala Thr Thr Gly Ala
6320            6325                 6330

Thr Gly Gly Ala Thr Thr Cys Cys Cys Thr Cys Gly Thr Ala Ala
6335            6340                 6345

Gly Ala Thr Gly Gly Ala Cys Cys Ala Gly Gly Cys Cys Ala Ala 6350 6355 6360

Ala Ala Cys Thr Thr Thr Thr Gly Ala Gly Gly Ala Ala Ala Ala
6365 6370 6375

Ala Gly Thr Cys Gly Cys Ala Ala Ala Gly Thr Cys Cys Ala Ala
6380 6385 6390

Gly Gly Thr Gly Ala Cys Ala Cys Thr Thr Thr Thr Cys Thr Thr
6395 6400 6405

Thr Gly Ala Thr Thr Gly Thr Cys Cys Cys Gly Ala Ala Thr Cys
6410 6415 6420

Ala Gly Thr Gly Cys Thr Cys Cys Thr Thr Gly Ala Gly Ala Gly
6425 6430 6435

Ala Thr Thr Ala Cys Thr Thr Ala Ala Ala Ala Gly Ala Gly Gly
6440 6445 6450

Ala Cys Ala Gly Ala Cys Ala Ala Gly Cys Gly Gly Ala Ala Gly
6455 6460 6465

Ala Gly Ala Gly Gly Ala Thr Gly Ala Thr Ala Ala Thr Gly Cys
6470 6475 6480

Gly Gly Ala Gly Ala Gly Thr Ala Thr Cys Ala Ala Ala Ala Ala
6485 6490 6495

Ala Ala Gly Ala Thr Thr Cys Ala Ala Ala Ala Cys Ala Thr Thr
6500 6505 6510

Cys Gly Thr Gly Gly Ala Ala Ala Cys Thr Thr Cys Gly Ala Thr
6515 6520 6525

Gly Cys Cys Thr Gly Thr Gly Gly Thr Gly Gly Ala Cys Thr Ala
6530 6535 6540

Thr Thr Thr Cys Gly Gly Gly Ala Ala Gly Cys Ala Ala Gly Gly
6545 6550 6555

Ala Cys Gly Cys Gly Thr Thr Thr Thr Gly Ala Ala Gly Gly Thr
6560 6565 6570

Ala Thr Cys Thr Thr Gly Thr Gly Ala Cys Cys Ala Cys Cys Cys
6575 6580 6585

Thr Gly Thr Gly Gly Ala Thr Cys Ala Ala Gly Thr Gly Thr Ala
6590 6595 6600

Thr Thr Cys Ala Cys Ala Gly Gly Thr Thr Gly Thr Gly Thr Cys
6605 6610 6615

Gly Gly Thr Gly Cys Thr Ala Ala Ala Ala Gly Ala Gly Ala Ala
6620 6625 6630

Gly Gly Gly Gly Ala Thr Cys Thr Thr Thr Gly Cys Cys Gly Ala
6635 6640 6645

Thr Ala Ala Cys Gly Ala Gly Ala Cys Gly Gly Ala Gly Ala Ala
6650 6655 6660

Thr Ala Ala Ala Thr Ala Ala Ala Cys Ala Thr Thr Gly Thr Ala
6665 6670 6675

Ala Thr Ala Ala Gly Ala Thr Thr Thr Ala Gly Ala Cys Thr Gly
6680 6685 6690

Thr Gly Ala Ala Thr Gly Thr Thr Cys Thr Ala Thr Gly Thr Ala
6695 6700 6705

Ala Thr Ala Thr Thr Thr Thr Thr Cys Gly Ala Gly Ala Thr Ala
6710 6715 6720

Cys Thr Gly Thr Ala Thr Cys Thr Ala Thr Cys Thr Gly Gly Thr
6725 6730 6735

Gly Thr Ala Cys Cys Gly Thr Ala Thr Cys Ala Cys Thr Cys Thr
6740 6745 6750

-continued

| | | | | | | | | | | | |
|---|---|---|---|---|---|---|---|---|---|---|---|
| Gly | Gly | Ala | Cys | Thr | Thr | Gly | Cys | Ala | Ala | Cys | Thr Cys Ala |
| | 6755 | | | | 6760 | | | | 6765 | | |
| Thr | Thr | Gly | Ala | Thr | Thr | Ala | Cys | Thr | Thr | Gly | Thr Gly Cys Ala |
| | 6770 | | | | 6775 | | | | 6780 | | |
| Ala | Thr | Gly | Gly | Gly | Cys | Ala | Ala | Gly | Ala | Ala | Gly Gly Ala Thr |
| | 6785 | | | | 6790 | | | | 6795 | | |
| Ala | Gly | Cys | Thr | Cys | Thr | Ala | Gly | Ala | Ala | Gly | Ala Ala Gly |
| | 6800 | | | | 6805 | | | | 6810 | | |
| Ala | Ala | Gly | Ala | Ala | Ala | Ala | Gly | Gly | Ala | Gly | Cys Cys Gly |
| | 6815 | | | | 6820 | | | | 6825 | | |
| Cys | Cys | Thr | Gly | Ala | Ala | Gly | Ala | Gly | Cys | Thr | Gly Gly Ala Thr |
| | 6830 | | | | 6835 | | | | 6840 | | |
| Cys | Thr | Thr | Thr | Cys | Cys | Gly | Ala | Gly | Gly | Thr | Thr Gly Thr Thr |
| | 6845 | | | | 6850 | | | | 6855 | | |
| Cys | Cys | Ala | Ala | Cys | Thr | Thr | Thr | Gly | Gly | Thr | Thr Ala Thr |
| | 6860 | | | | 6865 | | | | 6870 | | |
| Gly | Ala | Gly | Gly | Ala | Ala | Thr | Thr | Thr | Cys | Ala | Thr Gly Thr Thr |
| | 6875 | | | | 6880 | | | | 6885 | | |
| Gly | Ala | Gly | Cys | Ala | Ala | Gly | Ala | Gly | Gly | Ala | Gly Ala Ala Thr |
| | 6890 | | | | 6895 | | | | 6900 | | |
| Cys | Cys | Gly | Gly | Thr | Cys | Gly | Ala | Thr | Cys | Ala | Ala Gly Ala Cys |
| | 6905 | | | | 6910 | | | | 6915 | | |
| Gly | Ala | Ala | Cys | Thr | Thr | Gly | Ala | Cys | Gly | Gly | Cys Cys Ala Thr |
| | 6920 | | | | 6925 | | | | 6930 | | |
| Ala | Ala | Thr | Gly | Gly | Cys | Cys | Thr | Ala | Gly | Cys | Thr Thr Gly Gly |
| | 6935 | | | | 6940 | | | | 6945 | | |
| Cys | Gly | Thr | Ala | Ala | Thr | Cys | Ala | Thr | Gly | Thr | Cys Ala Thr |
| | 6950 | | | | 6955 | | | | 6960 | | |
| Ala | Gly | Cys | Thr | Gly | Thr | Thr | Thr | Cys | Cys | Thr | Gly Thr Gly Thr |
| | 6965 | | | | 6970 | | | | 6975 | | |
| Gly | Ala | Ala | Ala | Thr | Thr | Gly | Thr | Thr | Ala | Thr | Cys Cys Gly Cys |
| | 6980 | | | | 6985 | | | | 6990 | | |
| Thr | Cys | Ala | Cys | Ala | Ala | Thr | Thr | Cys | Cys | Ala | Cys Ala Cys Ala |
| | 6995 | | | | 7000 | | | | 7005 | | |
| Ala | Cys | Ala | Thr | Ala | Cys | Gly | Ala | Gly | Cys | Cys | Gly Gly Ala Ala |
| | 7010 | | | | 7015 | | | | 7020 | | |
| Gly | Cys | Ala | Thr | Ala | Ala | Ala | Gly | Thr | Gly | Thr | Ala Ala Ala Gly |
| | 7025 | | | | 7030 | | | | 7035 | | |
| Cys | Cys | Thr | Gly | Gly | Gly | Gly | Thr | Gly | Cys | Cys | Thr Ala Ala Thr |
| | 7040 | | | | 7045 | | | | 7050 | | |
| Gly | Ala | Gly | Thr | Gly | Ala | Gly | Cys | Thr | Ala | Ala | Cys Thr Cys Ala |
| | 7055 | | | | 7060 | | | | 7065 | | |
| Cys | Ala | Thr | Thr | Ala | Ala | Thr | Thr | Gly | Cys | Gly | Thr Thr Gly Cys |
| | 7070 | | | | 7075 | | | | 7080 | | |
| Gly | Cys | Thr | Cys | Ala | Cys | Thr | Gly | Cys | Cys | Cys | Gly Cys Thr Thr |
| | 7085 | | | | 7090 | | | | 7095 | | |
| Thr | Cys | Cys | Ala | Gly | Thr | Cys | Gly | Gly | Gly | Ala | Ala Ala Cys Cys |
| | 7100 | | | | 7105 | | | | 7110 | | |
| Thr | Gly | Thr | Cys | Gly | Thr | Gly | Cys | Cys | Ala | Gly | Cys Thr Gly Cys |
| | 7115 | | | | 7120 | | | | 7125 | | |
| Ala | Thr | Thr | Ala | Ala | Thr | Gly | Ala | Ala | Thr | Cys | Gly Gly Cys Cys |
| | 7130 | | | | 7135 | | | | 7140 | | |

-continued

Ala Ala Cys Gly Cys Gly Cys Gly Gly Gly Ala Gly Ala Gly
        7145                7150                7155

Gly Cys Gly Gly Thr Thr Thr Gly Cys Gly Thr Ala Thr Thr Gly
    7160                7165                7170

Gly Gly Cys Gly Cys Thr Cys Thr Thr Cys Cys Gly Cys Thr Thr
    7175                7180                7185

Cys Cys Thr Cys Gly Cys Thr Cys Ala Cys Thr Gly Ala Cys Thr
    7190                7195                7200

Cys Gly Cys Thr Gly Cys Gly Cys Thr Cys Gly Gly Thr Cys Gly
    7205                7210                7215

Thr Thr Cys Gly Gly Cys Thr Gly Cys Gly Gly Cys Gly Ala Gly
    7220                7225                7230

Cys Gly Gly Thr Ala Thr Cys Ala Gly Cys Thr Cys Ala Cys Thr
    7235                7240                7245

Cys Ala Ala Ala Gly Gly Cys Gly Gly Thr Ala Ala Thr Ala Cys
    7250                7255                7260

Gly Gly Thr Thr Ala Thr Cys Cys Ala Cys Ala Gly Ala Ala Thr
    7265                7270                7275

Cys Ala Gly Gly Gly Gly Ala Thr Ala Ala Cys Gly Cys Ala Gly
    7280                7285                7290

Gly Ala Ala Ala Gly Ala Ala Cys Ala Thr Gly Thr Gly Ala Gly
    7295                7300                7305

Cys Ala Ala Ala Ala Gly Gly Cys Cys Ala Gly Cys Ala Ala Ala
    7310                7315                7320

Ala Gly Gly Cys Cys Ala Gly Gly Ala Ala Cys Cys Gly Thr Ala
    7325                7330                7335

Ala Ala Ala Ala Gly Gly Cys Cys Gly Cys Gly Thr Thr Gly Cys
    7340                7345                7350

Thr Gly Gly Cys Gly Thr Thr Thr Thr Thr Cys Cys Ala Thr Ala
    7355                7360                7365

Gly Gly Cys Thr Cys Cys Gly Cys Cys Cys Cys Cys Cys Thr Gly
    7370                7375                7380

Ala Cys Gly Ala Gly Cys Ala Thr Cys Ala Cys Ala Ala Ala Ala
    7385                7390                7395

Ala Thr Cys Gly Ala Cys Gly Cys Thr Cys Ala Ala Gly Thr Cys
    7400                7405                7410

Ala Gly Ala Gly Gly Thr Gly Gly Cys Gly Ala Ala Ala Cys Cys
    7415                7420                7425

Cys Gly Ala Cys Ala Gly Gly Ala Cys Thr Ala Thr Ala Ala Ala
    7430                7435                7440

Gly Ala Thr Ala Cys Cys Ala Gly Gly Cys Gly Thr Thr Thr Cys
    7445                7450                7455

Cys Cys Cys Cys Thr Gly Gly Ala Ala Gly Cys Thr Cys Cys Cys
    7460                7465                7470

Thr Cys Gly Thr Gly Cys Gly Cys Thr Cys Thr Cys Cys Thr Gly
    7475                7480                7485

Thr Thr Cys Cys Gly Ala Cys Cys Cys Thr Gly Cys Cys Gly Cys
    7490                7495                7500

Thr Thr Ala Cys Cys Gly Gly Ala Thr Ala Cys Cys Thr Gly Thr
    7505                7510                7515

Cys Cys Gly Cys Cys Thr Thr Thr Cys Thr Cys Cys Cys Thr Thr
    7520                7525                7530

Cys Gly Gly Gly Ala Ala Gly Cys Gly Thr Gly Gly Cys Gly Cys

-continued

```
                7535                7540                7545
Thr Thr Thr Cys Thr Cys Ala Thr Ala Gly Cys Thr Cys Ala Cys
        7550                7555                7560
Gly Cys Thr Gly Thr Ala Gly Gly Thr Ala Thr Cys Thr Cys Ala
        7565                7570                7575
Gly Thr Thr Cys Gly Gly Thr Gly Thr Ala Gly Thr Cys Gly
        7580                7585                7590
Thr Thr Cys Gly Cys Thr Cys Cys Ala Gly Cys Thr Gly Gly
        7595                7600                7605
Gly Cys Thr Gly Thr Gly Thr Gly Cys Ala Cys Gly Ala Ala Cys
        7610                7615                7620
Cys Cys Cys Cys Cys Gly Thr Thr Cys Ala Gly Cys Cys Cys Gly
        7625                7630                7635
Ala Cys Cys Gly Cys Thr Gly Cys Gly Cys Cys Thr Thr Ala Thr
        7640                7645                7650
Cys Cys Gly Gly Thr Ala Ala Cys Thr Ala Thr Cys Gly Thr Cys
        7655                7660                7665
Thr Thr Gly Ala Gly Thr Cys Cys Ala Ala Cys Cys Cys Gly Gly
        7670                7675                7680
Thr Ala Ala Gly Ala Cys Ala Cys Gly Ala Cys Thr Thr Ala Thr
        7685                7690                7695
Cys Gly Cys Cys Ala Cys Thr Gly Gly Cys Ala Gly Cys Ala Gly
        7700                7705                7710
Cys Cys Ala Cys Thr Gly Gly Thr Ala Ala Cys Ala Gly Gly Ala
        7715                7720                7725
Thr Thr Ala Gly Cys Ala Gly Ala Gly Cys Gly Ala Gly Gly Thr
        7730                7735                7740
Ala Thr Gly Thr Ala Gly Gly Cys Gly Gly Thr Gly Cys Thr Ala
        7745                7750                7755
Cys Ala Gly Ala Gly Thr Thr Cys Thr Thr Gly Ala Ala Gly Thr
        7760                7765                7770
Gly Gly Thr Gly Gly Cys Cys Thr Ala Ala Cys Thr Ala Cys Gly
        7775                7780                7785
Gly Cys Thr Ala Cys Ala Cys Thr Ala Gly Ala Ala Gly Gly Ala
        7790                7795                7800
Cys Ala Gly Thr Ala Thr Thr Thr Gly Gly Thr Ala Thr Cys Thr
        7805                7810                7815
Gly Cys Gly Cys Thr Cys Thr Gly Cys Thr Gly Ala Ala Gly Cys
        7820                7825                7830
Cys Ala Gly Thr Thr Ala Cys Cys Thr Thr Cys Gly Gly Ala Ala
        7835                7840                7845
Ala Ala Ala Gly Ala Gly Thr Thr Gly Gly Thr Ala Gly Cys Thr
        7850                7855                7860
Cys Thr Thr Gly Ala Thr Cys Cys Gly Gly Cys Ala Ala Ala Cys
        7865                7870                7875
Ala Ala Ala Cys Cys Ala Cys Cys Gly Cys Thr Gly Gly Thr Ala
        7880                7885                7890
Gly Cys Gly Gly Thr Gly Gly Thr Thr Thr Thr Thr Thr Thr Gly
        7895                7900                7905
Thr Thr Thr Gly Cys Ala Ala Gly Cys Ala Gly Cys Ala Gly Ala
        7910                7915                7920
Thr Thr Ala Cys Gly Cys Gly Cys Ala Gly Ala Ala Ala Ala Ala
        7925                7930                7935
```

-continued

```
Ala Ala Gly Gly Ala Thr Cys Thr Cys Ala Ala Gly Ala Ala Gly
        7940                7945                7950

Ala Thr Cys Cys Thr Thr Thr Gly Ala Thr Cys Thr Thr Thr Thr
        7955                7960                7965

Cys Thr Ala Cys Gly Gly Gly Gly Thr Cys Thr Gly Ala Cys Gly
        7970                7975                7980

Cys Thr Cys Ala Gly Thr Gly Gly Ala Ala Cys Gly Ala Ala Ala
        7985                7990                7995

Ala Cys Thr Cys Ala Cys Gly Thr Thr Ala Ala Gly Gly Gly Ala
        8000                8005                8010

Thr Thr Thr Thr Gly Gly Thr Cys Ala Thr Gly Ala Gly Ala Thr
        8015                8020                8025

Thr Ala Thr Cys Ala Ala Ala Ala Ala Gly Gly Ala Thr Cys Thr
        8030                8035                8040

Thr Cys Ala Cys Cys Thr Ala Gly Ala Thr Cys Cys Thr Thr Thr
        8045                8050                8055

Thr Ala Ala Ala Thr Thr Ala Ala Ala Ala Ala Thr Gly Ala Ala
        8060                8065                8070

Gly Thr Thr Thr Thr Ala Ala Ala Thr Cys Ala Ala Thr Cys Thr
        8075                8080                8085

Ala Ala Ala Gly Thr Ala Thr Ala Thr Ala Thr Gly Ala Gly Thr
        8090                8095                8100

Ala Ala Ala Cys Thr Thr Gly Gly Thr Cys Thr Gly Ala Cys Ala
        8105                8110                8115

Gly Thr Thr Ala Cys Cys Ala Ala Thr Gly Cys Thr Thr Ala Ala
        8120                8125                8130

Thr Cys Ala Gly Thr Gly Ala Gly Gly Cys Ala Cys Cys Thr Ala
        8135                8140                8145

Thr Cys Thr Cys Ala Gly Cys Gly Ala Thr Cys Thr Gly Thr Cys
        8150                8155                8160

Thr Ala Thr Thr Thr Cys Gly Thr Thr Cys Ala Thr Cys Cys Ala
        8165                8170                8175

Thr Ala Gly Thr Thr Gly Cys Cys Thr Gly Ala Cys Thr Cys Cys
        8180                8185                8190

Cys Cys Gly Thr Cys Gly Thr Gly Thr Ala Gly Ala Thr Ala Ala
        8195                8200                8205

Cys Thr Ala Cys Gly Ala Thr Ala Cys Gly Gly Gly Ala Gly Gly
        8210                8215                8220

Gly Cys Thr Thr Ala Cys Cys Ala Thr Cys Thr Gly Gly Cys Cys
        8225                8230                8235

Cys Cys Ala Gly Thr Gly Cys Thr Gly Cys Ala Ala Thr Gly Ala
        8240                8245                8250

Thr Ala Cys Cys Gly Cys Gly Ala Gly Ala Cys Cys Cys Ala Cys
        8255                8260                8265

Gly Cys Thr Cys Ala Cys Cys Gly Gly Cys Thr Cys Cys Ala Gly
        8270                8275                8280

Ala Thr Thr Thr Ala Thr Cys Ala Gly Cys Ala Ala Thr Ala Ala
        8285                8290                8295

Ala Cys Cys Ala Gly Cys Cys Ala Gly Cys Cys Gly Gly Ala Ala
        8300                8305                8310

Gly Gly Gly Cys Cys Gly Ala Gly Cys Gly Cys Ala Gly Ala Ala
        8315                8320                8325
```

-continued

Gly Thr Gly Gly Thr Cys Cys Thr Gly Cys Ala Ala Cys Thr Thr
8330                    8335              8340

Thr Ala Thr Cys Cys Gly Cys Cys Thr Cys Cys Ala Thr Cys Cys
8345                    8350              8355

Ala Gly Thr Cys Thr Ala Thr Thr Ala Ala Thr Thr Gly Thr Thr
8360                    8365              8370

Gly Cys Cys Gly Gly Gly Ala Ala Gly Cys Thr Ala Gly Ala Gly
8375                    8380              8385

Thr Ala Ala Gly Thr Ala Gly Thr Thr Cys Gly Cys Cys Ala Gly
8390                    8395              8400

Thr Thr Ala Ala Thr Ala Gly Thr Thr Thr Gly Cys Gly Cys Ala
8405                    8410              8415

Ala Cys Gly Thr Thr Gly Thr Thr Gly Cys Cys Ala Thr Thr Gly
8420                    8425              8430

Cys Thr Ala Cys Ala Gly Gly Cys Ala Thr Cys Gly Thr Gly Gly
8435                    8440              8445

Thr Gly Thr Cys Ala Cys Gly Cys Thr Cys Gly Thr Cys Gly Thr
8450                    8455              8460

Thr Thr Gly Gly Thr Ala Thr Gly Gly Cys Thr Thr Cys Ala Thr
8465                    8470              8475

Thr Cys Ala Gly Cys Thr Cys Cys Gly Gly Thr Thr Cys Cys Cys
8480                    8485              8490

Ala Ala Cys Gly Ala Thr Cys Ala Ala Gly Gly Cys Gly Ala Gly
8495                    8500              8505

Thr Thr Ala Cys Ala Thr Gly Ala Thr Cys Cys Cys Cys Cys Ala
8510                    8515              8520

Thr Gly Thr Thr Gly Thr Gly Cys Ala Ala Ala Ala Ala Ala Gly
8525                    8530              8535

Cys Gly Gly Thr Thr Ala Gly Cys Thr Cys Cys Thr Thr Cys Gly
8540                    8545              8550

Gly Thr Cys Cys Thr Cys Cys Gly Ala Thr Cys Gly Thr Thr Gly
8555                    8560              8565

Thr Cys Ala Gly Ala Ala Gly Thr Ala Ala Gly Thr Thr Gly Gly
8570                    8575              8580

Cys Cys Gly Cys Ala Gly Thr Gly Thr Thr Ala Thr Cys Ala Cys
8585                    8590              8595

Thr Cys Ala Thr Gly Gly Thr Thr Ala Thr Gly Gly Cys Ala Gly
8600                    8605              8610

Cys Ala Cys Thr Gly Cys Ala Thr Ala Ala Thr Thr Cys Thr Cys
8615                    8620              8625

Thr Thr Ala Cys Thr Gly Thr Cys Ala Thr Gly Cys Cys Ala Thr
8630                    8635              8640

Cys Cys Gly Thr Ala Ala Gly Ala Thr Gly Cys Thr Thr Thr Thr
8645                    8650              8655

Cys Thr Gly Thr Gly Ala Cys Thr Gly Gly Thr Gly Ala Gly Thr
8660                    8665              8670

Ala Cys Thr Cys Ala Ala Cys Ala Ala Gly Thr Cys Ala Thr Thr
8675                    8680              8685

Thr Cys Thr Gly Ala Gly Ala Ala Thr Ala Gly Thr Gly Thr Ala
8690                    8695              8700

Thr Gly Cys Gly Gly Cys Gly Ala Cys Cys Gly Ala Gly Thr Thr
8705                    8710              8715

Gly Cys Thr Cys Thr Thr Gly Cys Cys Cys Gly Gly Cys Gly Thr

-continued

```
    8720                8725                8730

Cys Ala  Ala Thr Ala Cys Gly  Gly Gly Ala Thr Ala  Ala Thr Ala
    8735                8740                8745

Cys Cys  Gly Cys Gly Cys Cys  Ala Cys Ala Thr Ala  Gly Cys Ala
    8750                8755                8760

Gly Ala  Ala Cys Thr Thr Thr  Ala Ala Ala Ala Gly  Thr Gly Cys
    8765                8770                8775

Thr Cys  Ala Thr Cys Ala Thr  Thr Gly Gly Ala Ala  Ala Ala Cys
    8780                8785                8790

Gly Thr  Thr Cys Thr Thr Cys  Gly Gly Gly Gly Cys  Gly Ala Ala
    8795                8800                8805

Ala Ala  Cys Thr Cys Thr Cys  Ala Ala Gly Gly Ala  Thr Cys Thr
    8810                8815                8820

Thr Ala  Cys Cys Gly Cys Thr  Gly Thr Thr Gly Ala  Gly Ala Thr
    8825                8830                8835

Cys Cys  Ala Gly Thr Thr Cys  Gly Ala Thr Gly Thr  Ala Ala Cys
    8840                8845                8850

Cys Cys  Ala Cys Thr Cys Gly  Thr Gly Cys Ala Cys  Cys Cys Ala
    8855                8860                8865

Ala Cys  Thr Gly Ala Thr Cys  Thr Thr Cys Ala Gly  Cys Ala Thr
    8870                8875                8880

Cys Thr  Thr Thr Thr Ala Cys  Thr Thr Thr Cys Ala  Cys Cys Ala
    8885                8890                8895

Gly Cys  Gly Thr Thr Thr Cys  Thr Gly Gly Gly Thr  Gly Ala Gly
    8900                8905                8910

Cys Ala  Ala Ala Ala Ala Cys  Ala Gly Gly Ala Ala  Gly Gly Cys
    8915                8920                8925

Ala Ala  Ala Ala Thr Gly Cys  Cys Gly Cys Ala Ala  Ala Ala Ala
    8930                8935                8940

Ala Gly  Gly Gly Ala Ala Thr  Ala Ala Gly Gly Gly  Cys Gly Ala
    8945                8950                8955

Cys Ala  Cys Gly Gly Ala Ala  Ala Thr Gly Thr Thr  Gly Ala Ala
    8960                8965                8970

Thr Ala  Cys Thr Cys Ala Thr  Ala Cys Thr Cys Thr  Thr Cys Cys
    8975                8980                8985

Thr Thr  Thr Thr Thr Cys Ala  Ala Thr Ala Thr Thr  Ala Thr Thr
    8990                8995                9000

Gly Ala  Ala Gly Cys Ala Thr  Thr Thr Ala Thr Cys  Ala Gly Gly
    9005                9010                9015

Gly Thr  Thr Ala Thr Thr Gly  Thr Cys Thr Cys Ala  Thr Gly Ala
    9020                9025                9030

Gly Cys  Gly Gly Ala Thr Ala  Cys Ala Thr Ala Thr  Thr Thr Gly
    9035                9040                9045

Ala Ala  Thr Gly Thr Ala Thr  Thr Thr Ala Gly Ala  Ala Ala Ala
    9050                9055                9060

Ala Thr  Ala Ala Ala Cys Ala  Ala Ala Thr Ala Gly  Gly Gly Gly
    9065                9070                9075

Thr Thr  Cys Cys Gly Cys Gly  Cys Ala Cys Ala Thr  Thr Thr Cys
    9080                9085                9090

Cys Cys  Cys Gly Ala Ala Ala  Ala Gly Thr Gly Cys  Cys Ala Cys
    9095                9100                9105

Cys Thr  Gly Ala Cys Gly Thr  Cys Thr Ala Ala Gly  Ala Ala Ala
    9110                9115                9120

-continued

```
Cys Cys Ala Thr Thr Ala Thr  Thr Ala Thr Cys Ala  Thr Gly Ala
    9125                9130              9135

Cys Ala Thr Thr Ala Ala Cys  Cys Thr Ala Thr Ala  Ala Ala Ala
    9140                9145              9150

Ala Thr Ala Gly Gly Cys Gly  Thr Ala Thr Cys Ala  Cys Gly Ala
    9155                9160              9165

Gly Gly Cys Cys Cys Thr Thr  Thr Cys Gly Thr Cys
    9170                9175              9180
```

SURFACE, ANCHORED FC-BAIT ANTIBODY DISPLAY SYSTEM

This application is a divisional of U.S. patent application Ser. No. 13/990,941, filed Aug. 6, 2013; which is the national phase of international patent application no. PCT/US2011/062286 filed Nov. 29, 2011 which claims the benefit of U.S. provisional patent application No. 61/458,771, filed Dec. 1, 2010; each of which is herein incorporated by reference in its entirety.

FIELD OF THE INVENTION

The field of the invention relates to antibody display systems and methods of use for identifying antibodies that bind specifically to an antigen.

BACKGROUND OF THE INVENTION

A technique for constructing and screening antibody libraries is phage display, whereby the protein of interest is expressed as a polypeptide fusion to a bacteriophage coat protein and subsequently screened by binding to immobilized or soluble biotinylated ligand.

Phage display, however, has several shortcomings. For example, some eukaryotic secreted proteins and cell surface proteins require post-translational modifications such as glycosylation or extensive disulfide isomerization, which are unavailable in bacterial cells.

Current yeast surface antibody display systems, such as cold capture, also suffer from various drawbacks. In the cold capture antibody display system, at low temperatures, the process of antibody release from host cell transport vesicles is delayed, so that the secreted antibody can be assayed on the cell surface for antigen binding. The cold capture method suffers from a low signal-to-noise ratio and identification of an antibody with specificity for the target antigen depends heavily on cellular expression levels of the antibody.

The affinity matrix system couples antibodies to the host cell surface, e.g., by biotin, where they can be assayed for antigen binding. The affinity matrix system exhibits a high incidence of cross-contamination between antibody clones. Antibodies may become decoupled from the host cell and, thus lose their link to the polynucleotides encoding their immunoglobulin chains.

Full length antibody display systems tether the full length antibody on the host cell surface by binding an immunoglobulin binding protein, such as protein A, that is fused to a cell surface anchor protein. The host cell contains polynucleotides encoding the antibody immunoglobulin chains. Typically, binding of the antibody occurs after the immunoglobulin binding protein is expressed on the cell surface. This system, thus, leads to some erroneous binding of the antibody to host cells that do not express the antibody.

SUMMARY OF THE INVENTION

The present invention provides, in part, an antibody display system that does not suffer from shortcomings of currently available systems. The present invention also allows coupling of antibody display to production strain selection. The strain discovered by surface display screening can be turned into the production strain while preserving the antibody sequence and integrity. This method enables screening for parameters such as antibody folding and expression.

The present invention provides an antibody display system comprising: (a) an isolated eukaryotic host cell (e.g., a *Pichia* cell such as *Pichia pastoris*); (b) a bait comprising a Fc immunoglobulin domain or functional fragment thereof (e.g., comprising a CH3, CH2-CH3 or VH-CH1 polypeptide) (e.g., human) fused to a surface anchor polypeptide or functional fragment thereof (e.g., wherein the cell comprises a polynucleotide encoding the bait); (c) one or more polynucleotides encoding an immunoglobulin light chain variable region; and (d) one or more polynucleotides encoding an immunoglobulin heavy chain variable region. Optionally, the antibody display system further comprises a non-tethered full antibody comprising said immunoglobulin light and heavy chains; and/or monovalent antibody fragment which is complexed with the Fc moiety of the bait. In an embodiment of the invention, said one or more polynucleotides encoding an immunoglobulin light chain variable region is from a genetically diverse population of immunoglobulin light chain variable regions (e.g., an immunoglobulin library); and/or, wherein said one or more polynucleotides encoding an immunoglobulin heavy chain variable region is from a genetically diverse population of immunoglobulin heavy chain variable regions (e.g., an immunoglobulin library). In an embodiment of the invention, the host cell comprises a polynucleotide encoding the bait which is operably associated with a regulatable promoter (e.g., a GUT1 promoter, a GADPH promoter or a PCK1 promoter).

The present invention also provides an isolated bait polypeptide, e.g., comprising an Fc immunoglobulin domain or functional fragment thereof (e.g., wherein the Fc is derived from an IgG1, IgG2, IgG3 or IgG4 immunoglobulin; e.g., human, e.g., comprising a VH-CH1, a CH2-CH3 or a CH3 polypeptide) fused to a surface anchor polypeptide (e.g., SED1) or functional fragment thereof. Any isolated polynucleotide encoding such a polypeptide; vectors including the polynucleotides and isolated host cells comprising the polynucleotides and vectors form part of the present invention. The scope of the present invention includes an isolated host cell (e.g., a eukaryotic host cell such as *Pichia*, e.g., *Pichia pastoris*) further comprising one or more polynucleotides encoding an immunoglobulin light chain variable region (e.g., from a library); and/or one or more polynucleotides encoding an immunoglobulin heavy chain variable region (e.g., from a library). In an embodiment of the invention, a host cell of the present invention includes the polypeptide located on the surface of the cell, e.g., on the cell membrane.

The present invention comprises an isolated host cell (e.g., *Pichia* such as *Pichia pastoris*) comprising a bait polypeptide complexed with an Fc/antigen-binding fragment, e.g., located at the host cell surface by a cell surface anchor (such as SED1) that is part of the bait; optionally wherein the Fc/antigen-binding fragment is bound to an antigen; optionally comprising an antibody or antigen-binding fragment thereof that comprises the light and heavy chain immunoglobulins of the Fc/antigen-binding fragment; for example, wherein the host cell comprises one or more polynucleotides encoding e.g., the bait, the light chain immunoglobulin and/or the heavy chain immunoglobulin.

The present invention also provides a composition comprising the host cell of the present invention (see e.g., above), further comprising a non-tethered full antibody comprising said immunoglobulin light and heavy chains; and/or an Fc/antigen-binding fragment of an antibody (e.g., a monovalent antibody fragment) which is complexed with the Fc moiety of the bait. In an embodiment of the invention, said full antibody or Fc/antigen-binding fragment is complexed with an antigen.

The present invention provides a method for determining if an antibody or antigen-binding fragment thereof specifically binds to an antigen comprising contacting an antibody display system with said antigen; wherein the antibody display system comprises: (a) an isolated eukaryotic host cell (e.g., *Pichia* such as *Pichia pastoris*) comprising a polynucleotide encoding an immunoglobulin light chain (e.g., from a library); and a polynucleotide encoding an immunoglobulin heavy chain (e.g., from a library); and (b) a bait comprising an Fc immunoglobulin domain or functional fragment thereof (e.g., human, e.g., comprising a VH-CH1, CH2-CH3 or CH3 polypeptide) fused to a surface anchor polypeptide or functional fragment thereof (e.g., SED1) on the surface of said eukaryotic host cell; wherein the Fc of said bait complexes with an Fc/antigen-binding fragment (e.g., a monovalent antibody fragment) comprising said immunoglobulin heavy and immunoglobulin light chains on the surface of the host cell; and determining if said Fc/antigen-binding fragment (e.g., monovalent antibody fragment) specifically binds to said antigen; wherein the antibody is determined to specifically bind said antigen if the monovalent antibody fragment specifically binds to said antigen. In an embodiment of the invention, the method further comprises isolating the polynucleotide(s) and, optionally, determining the nucleotide sequence. In an embodiment of the invention, the method further comprises inhibiting expression of said bait, then determining the affinity of said identified antibody or antigen-binding fragment thereof for said antigen. In an embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for identifying:
(i) an antibody or antigen-binding fragment thereof that binds specifically to an antigen; or (ii) a polynucleotide encoding an immunoglobulin heavy chain of said antibody or fragment (e.g., from a library) and/or a polynucleotide encoding an immunoglobulin light chain of said antibody or fragment (e.g., from a library); comprising contacting an antibody display system with said antigen wherein the antibody display system comprises: (a) an isolated eukaryotic host cell (e.g., *Pichia* such as *Pichia pastoris*) comprising a polynucleotide encoding an immunoglobulin light chain; and a polynucleotide encoding an immunoglobulin heavy chain; and
(b) a bait comprising an Fc immunoglobulin domain or functional fragment thereof (e.g., human; e.g., comprising a VH-CH1, CH2-CH3 or CH3 polypeptide) fused to a surface anchor polypeptide or functional fragment thereof (e.g., SED1) on the surface of said eukaryotic host cell; wherein the Fc of said bait complexes with an Fc/antigen-binding fragment (e.g., a monovalent antibody fragment) comprising said immunoglobulin heavy and immunoglobulin light chains on the surface of the host cell; and determining if said Fc/antigen-binding fragment (e.g., monovalent antibody fragment) specifically binds to said antigen; wherein the antibody or fragment or polynucleotide is identified if said specific binding to said antigen is observed. In an embodiment of the invention, the method further comprises isolating the polynucleotide(s) and, optionally, determining the nucleotide sequence. In an embodiment of the invention, the method further comprises inhibiting expression of said bait, then determining the affinity of said identified antibody or antigen-binding fragment thereof for said antigen. In an embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for making an antibody display system comprising: (a) an isolated eukaryotic host cell (e.g., *Pichia* such as *Pichia pastoris*); (b) a bait comprising a human Fc immunoglobulin domain or functional fragment thereof (e.g., human; e.g., comprising a VH-CH1, CH2-CH3 or CH3 polypeptide) fused to a surface anchor polypeptide or functional fragment thereof (e.g., SED1); (c) one or more polynucleotides encoding an immunoglobulin light chain variable region (e.g., from a library); (d) one or more polynucleotides encoding an immunoglobulin heavy chain variable region (e.g., from a library); comprising introducing, into said eukaryotic host cell, a polynucleotide encoding said bait, said one or more polynucleotides encoding an immunoglobulin light chain variable region; and said one or more polynucleotides encoding an immunoglobulin heavy chain variable region.

The present invention also provides a method for making an antibody or antigen-binding fragment thereof comprising introducing, into an isolated eukaryotic host cell (e.g., *Pichia* such as *Pichia pastoris*) comprising a bait that includes a human Fc immunoglobulin domain or functional fragment thereof (e.g., human; e.g., comprising a VH-CH1, CH2-CH3 or CH3 polypeptide) fused to a surface anchor polypeptide or functional fragment thereof (e.g., SED1), one or more polynucleotides encoding an immunoglobulin light chain variable region; and/or one or more polynucleotides encoding an immunoglobulin heavy chain variable region; and culturing the host cell under condition whereby the polynucleotides encoding the immunoglobulin chains are expressed and an antibody or antigen-binding fragment thereof is formed from said chains; wherein said bait is operably associated with a regulatable promoter (e.g., a GUT1 promoter, a GADPH promoter or a PCK1 promoter) and bait expression is inhibited when said immunoglobulin chains are expressed.

The present invention further comprises a method for making an antibody or antigen binding fragment thereof comprising culturing an isolated eukaryotic host cell (e.g., *Pichia pastoris*) in a growth medium under conditions allowing expression of an immunoglobulin light chain and an immunoglobulin heavy chain of said antibody or fragment; wherein the eukaryotic host cell comprises: (i) a polynucleotide encoding said immunoglobulin light chain; and a polynucleotide encoding said immunoglobulin heavy chain of said antibody or fragment (e.g., wherein said chains are encoded by one common polynucleotide or two separate polynucleotides; and/or, wherein said one or both of said polynucleotides were obtained from a library or from a single clonal source); and (ii) a bait comprising an Fc immunoglobulin domain or functional fragment thereof (e.g., human; e.g., comprising a VH-CH1, CH2-CH3 or CH3 polypeptide) fused to a surface anchor polypeptide or functional fragment thereof on the surface of said eukaryotic host cell; wherein the Fc of said bait complexes with an Fc/antigen-binding fragment (e.g., an monovalent antibody fragment) comprising said immunoglobulin heavy and immunoglobulin light chains on the surface of the host cell; and wherein the expression of the bait is optionally inhibited; wherein said antibody or fragment is optionally secreted from said eukaryotic host cell; optionally comprising isolating said antibody or fragment from said eukaryotic host cell and medium.

The present invention further provides a method for determining the effect of a sugar (e.g., an O-glycan and/or an N-glycan, e.g., any of those discussed herein) on an antibody or antigen-binding fragment thereof which specifically binds to an antigen comprising contacting an antibody display system with said antigen; wherein the antibody display system comprises:

(a) an isolated eukaryotic controlled glycosylation host cell (e.g., *Pichia pastoris*) comprising a polynucleotide encoding an immunoglobulin light chain; and a polynucleotide encoding an immunoglobulin heavy chain; and (b) a bait comprising an Fc immunoglobulin domain or functional fragment thereof (e.g., human; e.g., comprising a VH-CH1, CH2-CH3 or CH3 polypeptide) comprising said sugar fused to a surface anchor polypeptide or functional fragment thereof on the surface of said host cell;

wherein the Fc of said bait complexes with the Fc/antigen-binding fragment comprising said immunoglobulin heavy and immunoglobulin light chains on the surface of the host cell; wherein said heavy and/or light chain comprises said sugar;

determining if said Fc/antigen-binding fragment specifically binds to said antigen; determining the binding affinity of the antibody or antigen-binding fragment thereof comprising said sugar for the antigen; and comparing the affinity of the antibody or antigen-binding fragment thereof for the antigen with affinity for the antigen of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar.

BRIEF DESCRIPTION OF THE FIGURES

FIGS. 7a-7b. PCSK9 and Kappa ELISA analysis of presorted (a) BP550 and (b) BP551 library and round 2 sorted pools thereof.

DETAILED DESCRIPTION OF THE INVENTION

Figure 1:
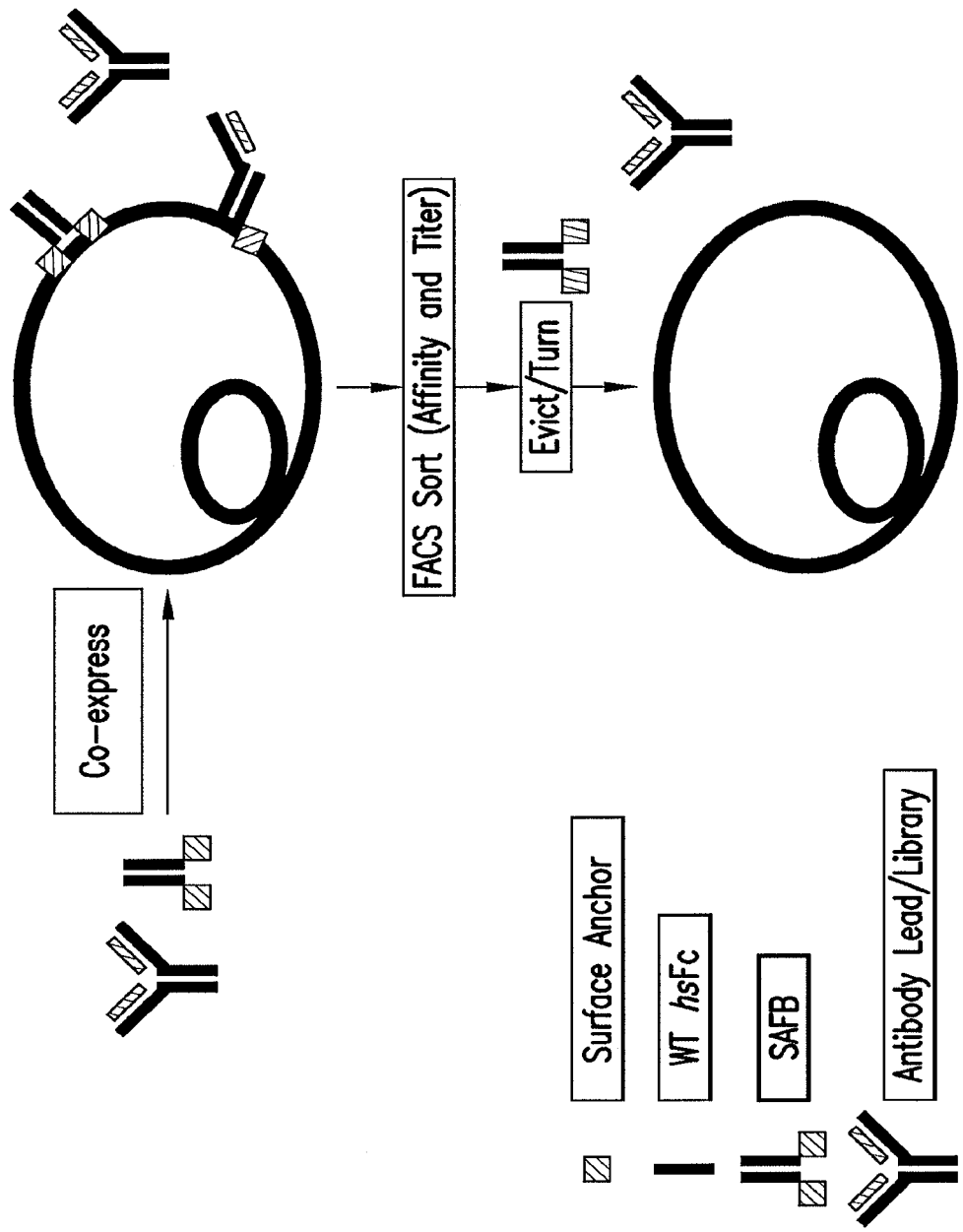
FIG. 1. Antibody display system of the present invention and a method of use thereof. Polynucleotide encoding an antibody and bait are co-expressed in *Pichia pastoris*. The polynucleotide encoding one or both of the antibody immunoglobulin chains can be from a library or can be from a single clonal source. The *Pichia* cell expresses the bait on the cell surface, some of such baits are bound by a monovalent antibody fragment (comprising one heavy and one light chain) of the antibody that is also expressed. Some expressed antibody escapes bait binding and is, thus, soluble. Expression of the antibody on the cell can be confirmed by FACS analysis and a titer of the cellular antibody expression level can also be determined. The bait expression is turned off or the polynucleotide encoding the bait is evicted (or knocked-out) from the cell. The resulting cell expresses only the polynucleotide encoding the antibody heavy and light chains and produces only full soluble antibody. Cellular expression levels of the antibody can then be confirmed and a determination of the antibody affinity can also be performed.

The present invention provides a method and system for antibody surface display that simultaneously features a display mode and full antibody secretion mode. Host cells secrete full antibody and display Fc/antigen-binding fragments on the cell surface. This method utilizes an Fc fusion (e.g., fused at the N- or C-terminus) with a cell surface protein as "bait" that is covalently coupled to the cell surface (e.g., the cell wall) or embedded (partially or fully) in the cell membrane (e.g., as a transmembrane protein) and that is co-expressed with an antibody (e.g., a single specific antibody from a clonal source or an antibody from a library). In the endoplasmic reticulum, where antibody molecules normally dimerize to form the full antibody molecule, a surface anchored Fc fusion "bait" heterodimerizes with a monovalent antibody fragment creating a complex that is displayed on the cell surface. Monovalent antibody fragments on the cell surface can bind antigen.

The antibody system of the present invention can be employed in any host cell (e.g., yeast, mammalian cells, bacteria) wherein a bait can be expressed on the host cell surface and an Fc/antigen-binding fragment can bind to the bait.

Homodimerization of full antibody still occurs allowing secretion of full antibody molecules into the culture supernatant. The secreted full antibody can be used, e.g., for preclinical studies, e.g., after isolation.

If desired, bait can be knocked-out or mutated or its expression can be turned off to create a strain producing only the full antibody.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A library is, typically, a collection of related but diverse polynucleotides that are, in general, in a common vector backbone. For example, a light chain or heavy chain immunoglobulin library may contain polynucleotides, in a common vector backbone, that encode light and/or heavy chain immunoglobulins which are diverse but related in their nucleotide sequence; for example, which immunoglobulins are functionally diverse in their abilities to form complexes with other immunoglobulins, e.g., in an antibody display system of the present invention, and bind a particular antigen.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be spliced (if it contains introns) and translated into a protein encoded by the coding sequence. Thus, a bait gene can be operably associated with a promoter, such as a regulatable promoter or a constitutive promoter.

Polynucleotides discussed herein form part of the present invention. A "polynucleotide", "nucleic acid" or "nucleic acid molecule" include DNA and RNA, single or double stranded.

Polynucleotides e.g., encoding an immunoglobulin chain or component of the antibody display system of the present invention (e.g., a bait), may, in an embodiment of the invention, be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

Polynucleotides e.g., encoding an immunoglobulin chain or component of the antibody display system of the present invention, may be operably associated with a promoter. A "promoter" or "promoter sequence" is, in an embodiment of the invention, a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

The terms "vector", "cloning vector" and "expression vector" include a vehicle (e.g., a plasmid) by which a DNA or RNA sequence can be introduced into a host cell, so as to transform the host and, optionally, promote expression and/or replication of the introduced sequence. Polynucleotides encoding an immunoglobulin chain or component of the antibody display system of the present invention (e.g., a bait) may, in an embodiment of the invention, be in a vector.

A host cell that may be used in a composition or method of the present invention, as is discussed herein, includes eukaryotes such a lower and higher eukaryotic cells as well as prokaryotics. Higher eukaryote cells include mammalian, insect (e.g., *Spodoptera frugiperda* cells), and plant cells (e.g., Protalix cells). In an embodiment of the invention, the host cell is a lower eukaryote such as a yeast or filamentous fungi cell, which, for example, is selected from the group consisting of any *Pichia* cell, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia, Saccharomyces cerevisiae, Saccharomyces, Hansβnula polymorpha, Kluyveromyces, Kluyveromyces lactis, Candida albicans, Aspergillus nidulans, Aspergillus niger, Aspergillus oryzae, Trichoderma reesei, Chrysosporium lucknowense, Fusarium, Fusarium gramineum, Fusarium venenatum* and *Neuraspora crassa*. A higher eukaryotic host cell includes a mammalian host cell for example a Chinese hamster ovary (CHO) cell, a BHK cell, or an NSO cell. A prokaryotic host cell can be, for example, a bacterial cell such as *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus*. *E. coli* host cells include DHB4, BL21 (which are deficient in both Lon (Phillips et al. (1984) J. Bacteriol. 159: 283) and OmpT proteases), HB101, BL21 DE3, *E. coli* AD494, *E. coli* W3110 (ATCC 27,325), *E. coli* 294 (ATCC 31,446), *E. coli* B, and *E. coli* X1776 (ATCC 31,537). Other strains include *E. coli* B834 which are methionine deficient (Leahy et al. (1992) Science 258, 987); other strains include the BLR strain, and the K-12 strains HMS174 and NovaBlue, which are recA-derivative that improve plasmid monomer yields and may help stabilize target plasmids containing repetitive sequences (these strains can be obtained from Novagen). See also U.S. Pat. Nos. 4,952,496, 5,693,489 and 5,869,320 and in Davanloo, P., et al., (1984) Proc. Natl. Acad. Sci. USA 81, 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259. Prokaryotic cells can also be cultured, for example, in a medium under conditions allowing for recombinant expression of a polypeptide, such as an immunoglobulin polypeptide and/or a bait. Such methods and host cells comprising such genes and proteins are part of the present invention. A prokaryotic host cell can also be used as a host cell in the antibody display system of the present invention, as discussed herein.

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. Predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)).

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms." "PNGase", or "glycanase" or "glucosidase" refer to peptide N-glycosidase F (EC 3.2.2.18).

In an embodiment of the invention, O-glycosylation of glycoproteins in a "eukaryotic host cell" is controlled. The scope of the present invention includes isolated eukaryotic host cells (e.g., *Pichia pastoris*) wherein O-glycosylation is controlled (as discussed herein) as well as antibody display systems comprising such eukaryotic host cells and methods of use thereof (as discussed herein). For example, wherein O-glycan occupancy and mannose chain length are reduced. In lower eukaryote host cells such as yeast, O-glycosylation can be controlled by deleting the genes encoding one or more protein O-mannosyltransferases (Dol-PMan: Protein (Ser/Thr) Mannosyl Transferase genes) (PMTs) or by growing the host in a medium containing one or more Pmtp inhibitors. Thus, the present invention includes isolated eukaryotic host cells, antibody display systems and methods of use thereof (as is discussed herein), e.g., comprising a deletion of one or more of the genes encoding PMTs, and/or, e.g., wherein the host cell can be cultivated in a medium that includes one or more Pmtp inhibitors. Pmtp inhibitors include but are not limited to a benzylidene thiazolidinedione. Examples of benzylidene thiazolidinediones are 5-[[3,4bis(phenylmethoxy) phenyl]methylene]-4-oxo-2-thioxo-3-thiazolidineacetic Acid; 5-[[3-(1-25 Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo3-thiazolidineacetic acid.

In an embodiment of the invention, a "eukaryotic host cell" includes a nucleic acid that encodes an alpha-1,2-mannosidase that has a signal peptide that directs it for secretion. For example, in an embodiment of the invention, the host cell is engineered to express an exogenous alpha-1,2-mannosidase enzyme having an optimal pH between 5.1 and 8.0, preferably between 5.9 and 7.5. In an embodiment of the invention, the exogenous enzyme is targeted to the endoplasmic reticulum or Golgi apparatus of the host cell, where it trims N-glycans such as $Man_8GlcNAc_2$ to yield $Man_5GlcNAc_2$. See U.S. Pat. No. 7,029,872.

The scope of the present invention includes such an isolated eukaryotic host cell (e.g., *Pichia pastoris*) as well as antibody display systems comprising such eukaryotic host cells and methods of use thereof (as discussed herein).

"Eukaryotic host cells" are, in an embodiment of the invention, lower eukaryote cells (e.g., yeast such as *Pichia pastoris*) that are genetically engineered to eliminate glycoproteins having alpha-mannosidase-resistant N-glycans by deleting or disrupting one or more of the beta-mannosyltransferasegenes (e.g., BMT1, BMT2, BMT3, and BMT4) (See, U.S. Published Patent Application No. 2006/0211085) or abrogating translation of RNAs encoding one or more of the beta-mannosyltransferases using interfering RNA, antisense RNA, or the like. The scope of the present invention includes such an isolated eukaryotic host cell (e.g., *Pichia pastoris*) as well as antibody display systems comprising such eukaryotic host cells and methods of use thereof (as discussed herein).

"Eukaryotic host cells" also include lower eukaryote cells (e.g., yeast and filamentous fungi such as *Pichia pastoris*) that are genetically engineered to eliminate glycoproteins having phosphomannose residues, e.g., by deleting or disrupting one or both of the phosphomannosyl transferase genes PNO1 and MNN4B (See for example, U.S. Pat. Nos. 7,198,921 and 7,259,007), which can include deleting or disrupting the MNN4A gene or abrogating translation of RNAs encoding one or more of the phosphomannosyltransferases using interfering RNA, antisense RNA, or the like. In an embodiment of the invention, a "eukaryotic host cell" has been genetically modified to produce glycoproteins that have predominantly an N-glycan selected from the group consisting of complex N-glycans, hybrid N-glycans, and high mannose N-glycans wherein complex N-glycans are, in an embodiment of the invention, selected from the group consisting of $Man_3GlcNAc_2$, $GlcNAC_{(1-4)}Man_3GlcNAc_2$, $NANA_{(1-4)}GlcNAc_{(1-4)}Man_3GlcNAc_2$, and $NANA_{(1-4)}Gal_{(1-4)}Man_3GlcNAc_2$; hybrid N-glycans are, in an embodiment of the invention, selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high mannose N-glycans are, in an embodiment of the invention, selected from the group consisting of $Man_6GlcNAc_2$, $Man_7GlcNAc_2$, $Man_81cNAc_2$, and $Man_9GlcNAc_2$. The scope of the present invention includes such an isolated eukaryotic host cell (e.g., *Pichia pastoris*) as well as antibody display systems comprising such eukaryotic host cells and methods of use thereof (as discussed herein).

As used herein, the term "essentially free of" as it relates to lack of a particular sugar residue, such as fucose, or galactose or the like, on a glycoprotein, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent.

As used herein, a glycoprotein composition "lacks" or "is lacking" a particular sugar residue, such as fucose or galactose, when no detectable amount of such sugar residue is present on the N-glycan structures. For example, in preferred embodiments of the present invention, the glycoprotein compositions are produced by lower eukaryotic organisms, as discussed herein, and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

For example, a host cell which introduces, eliminates or modifies sugar residues on an immunoglobulin expressed in the host cell, e.g., as is discussed herein, may, in certain instances, be referred to herein as a "controlled glycosylation host cell."

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. During the cell sorting process, the cell suspension is entrained in the center of a narrow, rapidly flowing stream of liquid. The flow is arranged so that there is a separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately-prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off. The present invention encompasses methods of using the antibody display system of the present invention, e.g., as discussed herein, wherein the eukaryotic host cells that are bound to an antigen of interest (by the Fc/antigen-binding fragment) are sorted from unbound cells or cells without sufficient levels of binding, by FACS sorting, based on whether the cells are labeled with a detectable fluorescent label (e.g., wherein the antigen itself or a secondary antibody is labeled). Such sorted labeled host cells and compositions comprising such sorted labeled host cells are also part of the present invention.

A regulatable promoter is a promoter whose expression can be induced or inhibited. Embodiments of the invention include the antibody display system wherein expression of the bait is controlled by a regulatable promoter as well as methods of use thereof as discussed herein. Polynucleotides encoding the bait, operably associated with a regulatable promoter also form part of the present invention along with isolated eukaryotic host cells including the polynucleotides. Examples of regulatable promoters that occur in yeast include the GUT1 promoter, GADPH promoter and the PCK1 promoter.

In an embodiment of the invention, expression of a polynucleotide (e.g., the bait) in a eukaryotic host cell (e.g., a bait) is inhibited by exposing the cells to anti-sense RNA or by RNA interference (e.g., microRNA (miRNA) or small interfering RNA (miRNA)). Embodiments of the invention include methods of using antibody display system (e.g., as discussed herein) wherein expression of the bait is inhibited by RNA interference or anti-sense RNA. Isolated eukaryotic host cells of the present invention (e.g., as discussed herein) comprising bait and further comprising an anti-sense or RNA interference molecule that inhibits bait expression are part of the present invention.

Antibodies

Antibodies or antigen-binding fragments thereof identified in connection with use of the present invention (e.g., use of the antibody display system of the present invention) may be reformatted into any suitable form. For example, CDRs from a full antibody isolated using the antibody display system can be incorporated into a different framework (e.g., a human framework) to generate a distinct antibody or antigen-binding fragment comprising the CDRs isolated from the antibody display system of the present invention. Methods for producing chimeric, humanized and human antibodies are well known in the art. See, e.g., U.S. Pat. No. 5,530,101, issued to Queen et al., U.S. Pat. No. 5,225,539, issued to Winter et al., U.S. Pat. No. 4,816,397 issued to Boss et al. Such methods for reformatting an antibody or antigen-binding fragment or for relocating CDRs from one framework to another are conventional and well known in the art. For example, the CDRs of an antibody or antigen-binding fragment can be used to generate monoclonal antibodies, polyclonal antibodies, bispecific antibodies, chimeric antibodies, recombinant antibodies, anti-idiotypic antibodies, humanized antibodies and bispecific antibodies; or antigen-binding fragments thereof such as nanobodies, Fab, Fab', F(ab')$_2$, Fv fragments; dsFv; (dsFv)$_2$, ds diabodies; dsFv-dsFv'; single-chain antibody molecules, e.g., sc-Fv, sc-Fv dimers (bivalent diabodies); and bispecific diabodies.

A full antibody comprises a tetramer of subunits. Each tetramer has two identical pairs of polypeptide chains, each pair having one "light" chain (LC) (about 25 kDa) and one "heavy" chain (HC) (about 50-70 kDa). The amino-terminal portion of each chain includes a variable region of about 100 to 110 or more amino acids primarily responsible for antigen recognition. The carboxy-terminal portion of each chain defines a constant domain, in part, responsible for effector function. Light chains (LCs) are classified as either kappa or lambda based on the type of constant domain in the light chain. Heavy chains (HCs) are classified as gamma, mu, alpha, delta, or epsilon, based on the type of constant domain in the heavy chain, and define the antibody's isotype as IgG (e.g., IgG1, IgG2, IgG2a, IgG2b, IgG3 or IgG4), IgM, IgA (e.g., IgA1 or IgA2), IgD or IgE, respectively.

The present invention encompasses methods for making an antibody or antigen-binding fragment thereof comprising introducing, into an isolated host cell (e.g., a eukaryotic host cell such as *Pichia*, e.g., *Pichia pastoris*) comprising a bait that includes a human Fc immunoglobulin domain or functional fragment thereof (e.g., human; e.g., comprising a VH-CH1, CH2-CH3 or CH3 polypeptide) fused to a surface anchor polypeptide or functional fragment thereof, one or more polynucleotides encoding an immunoglobulin light chain variable region; and/or one or more polynucleotides encoding an immunoglobulin heavy chain variable region and culturing the host cell under condition whereby the polynucleotides encoding the immunoglobulin chains are expressed and an antibody or antigen-binding fragment thereof is formed from said chains.

In an embodiment of the invention, said bait is operably associated with a regulatable promoter and the bait expression is inhibited when said immunoglobulin chains are expressed. In an embodiment of the invention, bait expression is inhibited with anti-sense RNA or by RNA interference.

The present invention also provides a method for determining the quantity of an antibody or antigen-binding fragment thereof, e.g., by enzyme linked immunosorbent assay (ELISA). For example, in an embodiment of the invention, the method comprises culturing a eukaryotic host cell comprising an isolated polypeptide comprising a bait polypeptide (Fc immunoglobulin domain or functional fragment thereof (e.g., human; e.g., comprising a VH-CH1, CH2-CH3 or CH3 polypeptide) fused to a surface anchor polypeptide or functional fragment thereof); wherein the host cell secretes full antibody or antigen-binding fragment thereof (optionally, the antibody or fragment is isolated from the host cell and/or culture medium); and determining the quantity of the antibody or antigen-binding fragment thereof by ELISA. In an embodiment of the invention, expression of the bait is inhibited before quantitation such that the host cell expresses and secretes only full antibody. Bait polynucleotide can be operably associated with a regulatable promoter which is inhibited so as to inhibit bait expression. For example, in an embodiment of the invention, ELISA comprises coating the antigen on a solid substrate; binding the antibody or antigen-binding fragment thereof to the antigen; binding a detectably labeled secondary antibody to the antibody or fragment; and detecting the secondary antibody. In an embodiment of the invention, the secondary antibody is labeled with alkaline phosphatase or horse radish peroxidase. In an embodiment of the invention, the label is detected by binding the alkaline phosphatase (AP) or horse radish peroxidase (HRP) with substrate and measuring absorbance of the plate (e.g., HRP substrate 3,3',5,5'-tetramethylbenzidine (TMB); HRP substrate 3,3'-diaminobenzidine (DAB); or HRP substrate 2,2'-azino-bis(3-ethylbenzthiazoline-6-sulphonic acid) (ABTS); or AP substrate para-nitrophenylphosphate).

The present invention also provides a method for determining the affinity of an antibody or antigen-binding fragment thereof, that is secreted from a eukaryotic host cell in the antibody display system of the present invention, for an antigen. For example, the affinity can be determined by standard affinity ELISA, Biacore analysis or competition assays.

Antibody Display System

The present invention provides an antibody display system, composition or kit comprising (1) a eukaryotic host cell and (2) a bait comprising an Fc (e.g., a human Fc, e.g., comprising a VH-CH1, a CH3, or a CH2-CH3 polypeptide) fused, at the N- or C-terminus, (optionally, by a peptide linker such as GGG) to a surface anchor which bait is optionally linked to a signal sequence (e.g., an alpha mating factor signal sequence, e.g., from *Saccharomyces cerevisiae*); which system may be used, for example, in the identification of antibodies. Thus, in an embodiment of the invention, the host cell in the system expresses one or more immunoglobulin chains (e.g., light and heavy chains, e.g., wherein one or more of the chains are from a library source) of an antibody and/or of an Fc/antigen-binding fragment thereof. In an embodiment of the invention, the immunoglobulin chains of an antibody and/or of an Fc/antigen-binding fragment thereof comprises an identical or different CH2-CH3 polypeptide from that of the bait.

An Fc/antigen-binding fragment of an antibody (1) complexes with the Fc moiety of the bait (e.g., a human Fc, e.g., comprising a VH-CH1, CH3 or CH2-CH3 polypeptide) and (2) binds to an antigen when complexed with the bait on the surface of the host cell. An example of an Fc/antigen-binding fragment is a monovalent fragment of a full antibody (i.e., a monovalent antibody fragment). In an embodiment of the invention, the bait comprises a CH2-CH3 polypeptide or functional fragment thereof that differs at one or more residues from the CH2-CH3 of the Fc/antigen-binding fragment of an antibody. In such an embodiment of the invention, when the bait and the Fc/antigen-binding fragment of an antibody bind, a heterodimeric Fc domain is formed.

A "monovalent antibody fragment" comprises one half of an antibody, i.e., the antibody heavy chain (VH-CH1-CH2-CH3) bound to the antibody light chain (VL-CL) comprising three paired CDRs, e.g., wherein CH1 and CL are bound by a disulfide bridge, which monovalent antibody fragment is capable of detectably binding an antigen.

The "bait" comprises an Fc domain (e.g., human, rat, rabbit, goat or mouse Fc, e.g., any part of the heavy chain (e.g., human, rat, rabbit, goat or mouse) such as, for example, a CH3 polypeptide, a VH-CH1 polypeptide or a CH2-CH3 polypeptide) fused, e.g., at the amino-terminus or carboxy-terminus, to a surface anchor, which bait possesses functional properties described herein (e.g., as set forth below) that enable the bait to function in the antibody display system of the present invention. The Fc domain can, in an embodiment of the invention, be mutated so as to improve its ability to function in the antibody display system of the present invention, for example, cysteines or other residues may be added or moved to allow for more extensive disulfide bridges to form when complexed with a human IgG Fc or Fc/antigen-binding fragment. An Fc suitable for use in the bait comprises an Fc (i.e., comprising the CH1 and/or CH2 and/or CH3 domains) or functional fragment thereof (e.g., from an IgG1, IgG2, IgG3 or IgG4 or a mutant thereof) that is capable of dimerizing, when fused to a surface anchor protein, with, for example, a human IgG Fc or with the Fc/antigen-binding fragment on the surface of a eukaryotic host cell. In an embodiment of the invention, the term "Fc" refers to the "fragment crystallized" C-terminal region of an antibody containing the CH2 and CH3 domains. In an embodiment of the invention, dimerization between the bait Fc and the Fc/antigen-binding fragment occurs intracellularly, prior to routing to the cell surface, wherein the Fc and an Fc/antigen-binding fragment remain associated once at the cell surface. In general, in the absence of the Fc/antigen-binding fragment, the bait homodimerizes; thus comprising two surface anchors and two Fc domains. In an embodiment of the invention, a full antibody that is co-expressed with the bait comprises light and heavy chains capable of dimerizing with each other to form a monovalent antibody fragment, which monovalent antibody fragment dimerizes with the Fc of the bait.

An antigen can be any immunogenic molecule or substance, for example, a polypeptide (e.g., an oligopeptide), a cell membrane, cell extract or a whole cell. Polypeptide antigens include, for example, the following polypeptides: chemokines, cytokines (e.g., inflammatory cytokines or chemokines), receptors, PCSK9, granulocyte-CSF; coagulation factors such as factor VIII, factor IX, and human protein C; soluble IgE receptor alpha-chain; urokinase; chymase and urea trypsin inhibitor; IGF-binding protein; insulin-like growth factor-1 receptor, vascular epidermal growth factor, epidermal growth factor; growth hormone-releasing factor; GITR (glucocorticoid-induced TNFR-related protein), annexin V fusion protein; IL-23p19, IL-23p40, IL-23R, IL12R-beta 1, TNF alpha (tumor necrosis factor alpha), TGF beta (transforming growth factor beta), IL-10, IL-17, TSLP (Thymic stromal lymphopoietin), angiostatin; vascular endothelial growth factor-2; myeloid progenitor inhibitory factor-1; osteoprotegerin (OPG), RANK (receptor activator for nuclear factor kappa B) or RANKL (receptor activator for nuclear factor kappa B ligand); any of which can be, in an embodiment of the invention, human.

A "surface anchor" is any polypeptide that, when fused with an Fc or functional fragment thereof, is expressed and located to the cell surface where an Fc/antigen-binding fragment can complex with the Fc or functional fragment thereof. An example of a cell surface anchor is a protein such as, but not limited to, SED-1, α-agglutinin, Cwp1, Cwp2, GasI, Yap3, FloIp1 Crh2, Pirl, Pir4, Tipl, Wpi, Hpwpl, Als3, and Rbt5; for example, *Saccharomyces cerevisiae* CWP1, CWP2, SED1, or GAS1; *Pichia pastoris* SP1 or GAS1; or *H. polymorpha* TIP1. In an embodiment of the invention, the surface anchor is any glycosylphosphatidylinositol-anchored (GPI) protein. A functional fragment of a surface anchor comprises a fragment of a full surface anchor polypeptide that is capable of forming a functional bait when fused to an Fc or functional fragment thereof; e.g., wherein the fragment, when expressed in a eukaryotic host cell as a Fc fusion, is located on the cell surface wherein the Fc is capable of forming a complex with an Fc/antigen-binding fragment (e.g., a monovalent antibody fragment).

As discussed herein, a suitable eukaryotic host cell for use in the antibody display system of the present invention is a *Pichia* cell such as *Pichia pastoris*.

The scope of the present invention encompasses an isolated eukaryotic host cell (e.g., *Pichia pastoris*) comprising a bait (i.e., comprising the human Fc domain or functional fragment thereof fused, e.g., at the amino-terminus or carboxy-terminus, to the surface anchor or functional fragment thereof) on the cell surface wherein the bait is dimerized with an Fc/antigen-binding fragment, e.g., by binding between the bait Fc and the heavy chain of a monovalent antibody fragment (e.g., between the CH2-CH3 polypeptides in the bait and the Fc/antigen-binding fragment). The present invention also includes a composition comprising a eukaryotic host cell comprising a bait and secreted antibody or antigen-binding fragment thereof and/or Fc/antigen-binding fragment thereof, e.g., in a liquid culture medium.

The present invention provides, for example, a method for identifying (i) an antibody or Fc/antigen-binding fragment thereof that binds specifically to an antigen of interest and/or (ii) a polynucleotide encoding an immunoglobulin heavy chain of said antibody or fragment and/or a polynucleotide encoding an immunoglobulin light chain of said antibody or fragment. The method comprises, in an embodiment of the invention:

(a) co-expressing a bait (e.g., comprising a polypeptide comprising a CH3, VH-CH1 or CH2-CH3 polypeptide that is linked to a cell surface anchor, such as SED1) and one or more heavy and light immunoglobulin chains (e.g., wherein one or more of such chains are encoded by a polynucleotide from a library source) in an isolated eukaryotic host cell (e.g., *Pichia pastoris*) such that a complex between the Fc moiety of the bait (e.g., comprising a VH-CH1, CH3 or CH2-CH3 polypeptide) and an Fc/antigen-binding fragment (e.g., a monovalent antibody fragment) comprising the immunoglobulin chains forms, and is located at the cell surface; for example, wherein the host cell is transformed with one or more polynucleotides encoding the bait and the immunoglobulin chains;

(b) identifying a eukaryotic host cell expressing the bait, dimerized with the Fc/antigen-binding fragment of the antibody (e.g., a monovalent antibody fragment), which has detectable affinity (e.g., acceptable affinity) for the antigen (e.g., which detectably binds to the antigen); for example, wherein the bait, and light and heavy chain immunoglobulins are encoded by the polynucleotides in the eukaryotic host cell;

In an embodiment of the invention, non-tethered, secreted full antibodies comprising light and heavy chain immunoglobulin variable domains identical to those complexed with the bait (e.g., immunoglobulins that are expressed from the host cell) are analyzed to determine if they possess detectable affinity.

In an embodiment of the invention, the full antibodies are secreted from the host cell into the medium. In an embodiment of the invention, the full antibodies are isolated from the host cell.

In an embodiment of the invention, after step (b), expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity); and, (c) identifying said antibodies or antigen-binding fragments or polynucleotides if detectable binding of the Fc/antigen-binding fragment is observed, e.g., wherein one or more of the polynucleotides encoding the light and/or heavy chain immunoglobulin are optionally isolated from the host cell. In an embodiment of the invention, the nucleotide sequence of the polynucleotide is determined.

In an embodiment of the invention, a population of host cells express a common bait and a common immunoglobulin heavy chain as well a variety of different light chain immunoglobulins, e.g., from a library source, wherein individual light chain immunoglobulins that form Fc/antigen-binding fragments and full antibodies that are tethered to the bait and which exhibit antigen binding can be identified. Similarly, in an embodiment of the invention, a population of host cells express a common bait and a common immunoglobulin light chain as well a variety of different heavy chain immunoglobulins, e.g., from a library source, wherein individual heavy chain immunoglobulins that form Fc/antigen-binding fragments and full antibodies that are tethered to the bait and which exhibit antigen binding can be identified.

In an embodiment of the invention, the host cell possessing polynucleotides encoding the heavy and light chain immunoglobulins can be further used to express the secreted non-tethered antibody (e.g., full antibody) or an antigen-binding fragment thereof in culture. For example, in this embodiment of the invention, expression of the bait is optionally inhibited so that bait expression at significant quantities does not occur. The host cell is then cultured in a culture medium under conditions whereby secreted, non-tethered antibody (e.g., full antibody) or antigen-binding fragment thereof is expressed and secreted from the host cell. The non-tethered antibody or antigen-binding fragment thereof can optionally be isolated from the host cell and culture medium. In an embodiment of the invention, the immunoglobulin chains are transferred to a separate host cell (e.g., lacking the antibody display system components) for recombinant expression.

The present invention provides, for example, a method for identifying (i) an antibody or Fc/antigen-binding fragment thereof that binds specifically to an antigen of interest which comprises a second CH2-CH3 that differs from a first CH2-CH3 of a bait at one or more residues or (ii) a polynucleotide encoding an immunoglobulin heavy chain of said antibody or fragment and/or a polynucleotide encoding an immunoglobulin light chain of said antibody or fragment. The method comprises, in an embodiment of the invention:

(a) co-expressing a bait comprising a first CH2-CH3 polypeptide; along with a heavy immunoglobulin chain comprising said second CH2-CH3 polypeptide (e.g., wherein said heavy immunoglobulin chain is from a library source) and a light immunoglobulin chain (e.g., VL-CL), in an isolated eukaryotic host cell (e.g., *Pichia pastoris*) such that a complex between the first CH2-CH3 polypeptide of the bait and the second CH2-CH3 polypeptide of a Fc/antigen-binding fragment binds and is located at the cell surface; for example, wherein the host cell is transformed with one or more polynucleotides encoding the bait and the immunoglobulin chains;

(b) identifying a eukaryotic host cell expressing the bait, dimerized with the Fc/antigen-binding fragment which has detectable affinity (e.g., acceptable affinity) for the antigen; for example, wherein the bait, and light and heavy chain immunoglobulins are encoded by the polynucleotides in the eukaryotic host cell; and, optionally, (c) identifying said antibodies or antigen-binding fragments or polynucleotides if detectable binding of the Fc/antigen-binding fragment is observed, e.g., wherein one or more of the polynucleotides encoding the light and/or heavy chain immunoglobulin are optionally isolated from the host cell. In an embodiment of the invention, the nucleotide sequence of the polynucleotide is determined.

The antibody display system of the present invention may be use to evaluate the effects of a given glycosylation pattern on the affinity of an antibody or antigen-binding fragment thereof for an antigen. In general, the ability of the Fc/antigen-binding fragment comprising an altered glyosylation pattern may be evaluated for binding to the antigen, after which affinity of the full antibody or antigen-binding fragment thereof can be evaluated. Glycosylation patterns can be modified on the immunoglobulin chains expressed in the antibody display system, for example, by using a host cell, e.g., as is discussed herein, that modifies the glycosylation patterns when the chains are expressed and/or by culturing a host under conditions whereby the glycosylation pattern is modified, e.g., as discussed herein. For example, in an embodiment of the invention, the method comprise contacting an antibody display system with said antigen; wherein the antibody display system comprises: (a) an isolated eukaryotic controlled glycosylation host cell comprising a polynucleotide encoding an immunoglobulin light chain; and a polynucleotide encoding an immunoglobulin heavy chain; and (b) a bait comprising an Fc immunoglobulin domain or functional fragment thereof fused to a surface anchor polypeptide or functional fragment thereof on the surface of said eukaryotic host cell; wherein the Fc of said bait complexes with an Fc/antigen-binding fragment comprising said immunoglobulin heavy and immunoglobulin light chains on the surface of the host cell; wherein said heavy or light chain comprises said sugar; determining if said Fc/antigen-binding fragment specifically binds to said antigen; determining the binding affinity of the antibody or antigen-binding fragment thereof comprising said sugar for the antigen; and comparing the affinity of the antibody or antigen-binding fragment thereof with affinity of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar. For example, the affinity of the antibody or antigen-binding fragment thereof lacking the sugar can be determined in a similar manner in the antibody display system of the present invention or the affinity or it can be determined directly by measuring affinity by a known method such as ELISA, biacore assay or a competition assay.

Bait expression can be inhibited by any of several acceptable means. For example, the polynucleotides encoding the bait (e.g., the surface anchor and/or Fc) can be expressed by a regulatable promoter whose expression can be inhibited in the host cell. In an embodiment of the invention, bait expression is inhibited by RNA interference, anti-sense RNA, mutation or removal of the polynucleotide encoding the bait (e.g., surface anchor and/or Fc) from the host cell or genetic mutation of the polynucleotide so that the host cell does not express a functional bait.

"Acceptable affinity" refers to antibody or antigen-binding fragment affinity for the antigen which is at least $10^{-3}$ M or a greater affinity (lower number), e.g., $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M or $10^{-12}$ M.

In an embodiment of the present invention, polynucleotides encoding the antibody or Fc/antigen-binding fragment (e.g., monovalent antibody fragment) heavy and light chain are in one or more libraries of polynucleotides that encode light and/or heavy chain immunoglobulins (e.g., one library encoding light chains and one library encoding heavy chains). The particular immunoglobulin chains of interest are, in this embodiment, distinguished from the other chains in the library when the surface-anchored Fc/antigen-binding fragment on the host cell surface is observed to bind to an antigen of interest.

In an embodiment of the invention, the heavy or light chain immunoglobulin expressed in the antibody display system is from a library source and the other immunoglobulin chain is known (i.e., a single chain from a clonal source). In this embodiment of the invention, the antibody display system can be used, as discussed herein, to identify a new library chain that forms desirable antibodies or antigen-binding fragments thereof when coupled with the known chain. Alternatively, the antibody display system can be used to analyze expression and binding characteristics of an antibody or antigen-binding fragment thereof comprising two known immunoglobulin chains.

In an embodiment of the invention, cells expressing Fc/antigen-binding fragments tethered to the cell by an anchor such as SED1 that bind to an antigen can be detected by incubating the cells with fluorescently labeled antigen (e.g., biotin label) and sorting/selecting cells that specifically bind the antigen by fluorescence-activated cell sorting (FACS).

In an embodiment of the invention, the eukaryotic host cells expressing the bait dimerized with the Fc/antigen-binding fragment are identified and sorted using fluorescence-activated cell sorting (FACS). For example, in an embodiment of the invention, cells expressing the bait dimerized with the Fc/antigen-binding fragment on the cell surface are labeled with a fluorescent antigen or fluorescent secondary antibody that also binds to the antigen. The fluorescent label is detected during the FACS sorting and used as the signal for sorting. Labeled cells indicate the presence of a cell surface expressed bait/Fc/antigen-binding fragment/antigen complex and are collected in one vessel whereas cells not expressing signal are collected in a separate vessel. The present invention, accordingly, includes the a method comprising the following steps for determining if an antibody or antigen-binding fragment thereof from a library specifically binds to an antigen:

(1) Transform:
   (i) one or more immunoglobulin libraries, containing polynucleotides encoding light and heavy chain immunoglobulins;
   (ii) one or more immunoglobulin libraries, containing polynucleotides encoding light chain immunoglobulins and a single clonal heavy chain immunoglobulin; or
   (iii) one or more immunoglobulin libraries, containing polynucleotides encoding heavy chain immunoglobulins and a single clonal light chain immunoglobulin;
   wherein, said chains are capable of forming an antibody or antigen-binding fragment thereof, into a eukaryotic host cell comprising polynucleotides encoding the bait (e.g., *Pichia pastoris*);
(2) Grow transformed cells in a liquid culture medium;
(3) Allow expression of the bait on the surface of the cells;
(4) Label the cells with fluorescently labeled antigen or antigen bound to a fluorescently labeled secondary antibody;
(5) Sort and isolate fluorescently labeled cells using FACS for one round;
(6) Regrow the labeled, sorted cells;
(7) Allow expression of the bait in the cells;
(8) Label the cells with fluorescently labeled antigen or antigen bound to a fluorescently labeled secondary antibody;
(9) Sort and isolate fluorescently labeled cells using FACS for a second round;
(10) Regrow the labeled, sorted cells on solid culture medium so that individual cellular clones grow into discrete cellular colonies;
(11) Identify colonies with affinity for the antigen;
(12) Grow cells from identified colonies in a liquid culture medium and isolate supernatant containing full, non-tethered antibody or antigen-binding fragment thereof comprising the immunoglobulin light and heavy chains; wherein, expression of the bait is optionally inhibited;
(13) Determine affinity of non-tethered antibodies or antigen-binding fragments thereof, from the supernatant, for the antigen and identify clones with acceptable affinity (e.g., by Biacore analysis);
(14) Determine the nucleotide sequence of polynucleotides in the identified clones encoding the heavy and light chain immunoglobulins.

The scope of the present invention also includes a method for identifying polynucleotides encoding a heavy chain and light chain immunoglobulin of an antibody or for identifying an antibody which exhibits high stability. Such a method comprises the following steps:

(a) co-expressing the bait and the polynucleotides encoding the heavy and light chains in a eukaryotic host cell (e.g., *Pichia pastoris*) while subjecting antibodies comprising said chains to a denaturant;

In an embodiment of the invention, a denaturant is present in a concentration or amount or magnitude (e.g., at a sufficiently high temperature) that a practitioner of ordinary skill in the art would expect to, at least partially, denature an antibody and, thus, inhibit its ability to bind to an antigen. For example, possible denaturants include urea (e.g., 2, 3, 4, 5 or 6 M or more), detergent such as triton X-100 (e.g., 1% or more), dithiothreitol (DTT) (e.g., 250 mM or 500 mM or more), guanidine hydrochloride, light (e.g., ultraviolet or visible), extreme pH (e.g., 1, 2, 3, 14, 13 or 12) or a temperature above about 4° C., such as 37° C. (e.g., 42° C., 48° C. or 50° C.) or any combination thereof (e.g., 500 mM DTT/6 M urea).

(b) identifying a eukaryotic host cell expressing the bait, dimerized with the Fc/antigen-binding fragment (e.g., a monovalent antibody fragment), which fragment has detectable affinity (e.g., acceptable affinity) for the antigen; In an embodiment of the invention, full antibodies comprising light and heavy chain variable regions identical to those complexed with the bait are also analyzed to determine if they possess detectable affinity.

In an embodiment of the invention, the full antibodies are secreted from the host cell. In an embodiment of the invention, the full antibodies are isolated from the host cell.

In an embodiment of the invention, expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity).

; and, (c) identifying said antibodies or polynucleotides encoding the heavy and light chains from the cell wherein one or more of the polynucleotides are optionally isolated from the host cell; wherein antibodies exhibiting affinity for the antigen in the presence of denaturant are determined to exhibit high stability. In an embodiment of the invention, the nucleotide sequence of the polynucleotide is determined.

In an embodiment of the invention, a human Fc immunoglobulin domain for use in a bait comprises the following amino acid sequence:

```
                                              (SEQ ID NO: 1)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPG
```

In an embodiment of the invention, SED1 comprises the following amino acid sequence:

```
                                              (SEQ ID NO: 2)
VDQFSNSTSASSTDVTSSSSISTSSGSVTITSSEAPESDNGTSTAAPTET

STEAPTTAIPTNGTSTEAPTTAIPTNGTSTEAPTDTTTEAPTTALPTNGT

STEAPTDTTTEAPTTGLPTNGTTSAFPPTTSLPPSNTTTTPPYNPSTDYT

TDYTVVTEYTTYCPEPTTFTTNGKTYTVTEPTTLTITDCPCTIEKPTTTS

TTEYTVVTEYTTYCPEPTTFTTNGKTYTVTEPTTLTITDCPCTIEKSEAP

ESSVPVTESKGTTTKETGVTTKQTTANPSLTVSTVVPVSSSASSHSVVIN

SNGANVVVPGALGLAGVAMLFL
```

In an embodiment of the invention, the human Fc immunoglobulin fused to the SED1 polypeptide is linked to a signal sequence such as an alpha mating factor signal sequence (e.g., MRFPSIFTAVLFAASSALA (SEQ ID NO: 3))

In an embodiment of the invention, the bait comprising the human Fc immunoglobulin domain fused to a SED1 polypeptide comprise the amino acid sequence:

```
                                              (SEQ ID NO: 4)
MRFPSIFTAVLFAASSALADKTHTCPPCPAPELLGGPSVFLFPPKPKDTL

MISRTPEVICVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLICLVKGFYPSDIAVEWESNGQPENNYKTIPPVLDSD

GSFFLYSKLTVDKSRWQQGNVFSCSVMHEALHNHYTQKSLSLSPGGGGVD

QFSNSTSASSTDVISSSSISTSSGSVTITSSEAPESDNGTSTAAPTETST

EAPTTAIPTNGTSTEAPTTAIPTNGTSTEAPTDTTTEAPTTALPTNGTST

EAPTDTTTEAPTTGLPTNGTTSAFPPTTSLPPSNTTTTPPYNPSTDYTTD

YTVVTEYTTYCPEPTTFTTNGKTYTVTEPTTLTITDCPCTIEKPTTTSTT

EYTVVTEYTTYCPEPTTFTTNGKTYTVTEPTTLTITDCPCTIEKSEAPES

SVPVTESKGTTTKETGVTTKQTTANPSLTVSTVVPVSSSASSHSVVINSN

GANVVVPGALGLAGVAMLFL.
```

The Fc immunoglobulin domain is underscored and the linked is in bold face font. The SED1 polypeptide follows the linker and an alpha mating factor signal peptide is before the Fc.

EXAMPLES

The present invention is intended to exemplify the present invention and not to be a limitation thereof. The methods and compositions (e.g., polypeptides, polynucleotides, plasmids, yeast cells) disclosed below fall within the scope of the present invention.

Example 1: Construction and Use of Antibody Display System

Construction of Antibody Display Bait

Expression cassettes were constructed as follows. A polynucleotide encoding the N-terminus of a cell surface anchoring protein that inherently contains an attached glycophosphotidylinositol (GPI) post-translational modification that anchors the protein on the yeast cell wall was linked to a nucleic acid sequence that encodes the human IgG1 Fc region. The specific cell surface anchoring protein we used was *S. cerevisiae* Sed1 protein, which had been identified by screening a panel of cell wall of plasma membrane proteins that had been identified using GPI protein prediction software (described in international publication no. WO09/111183).

Figure 2:
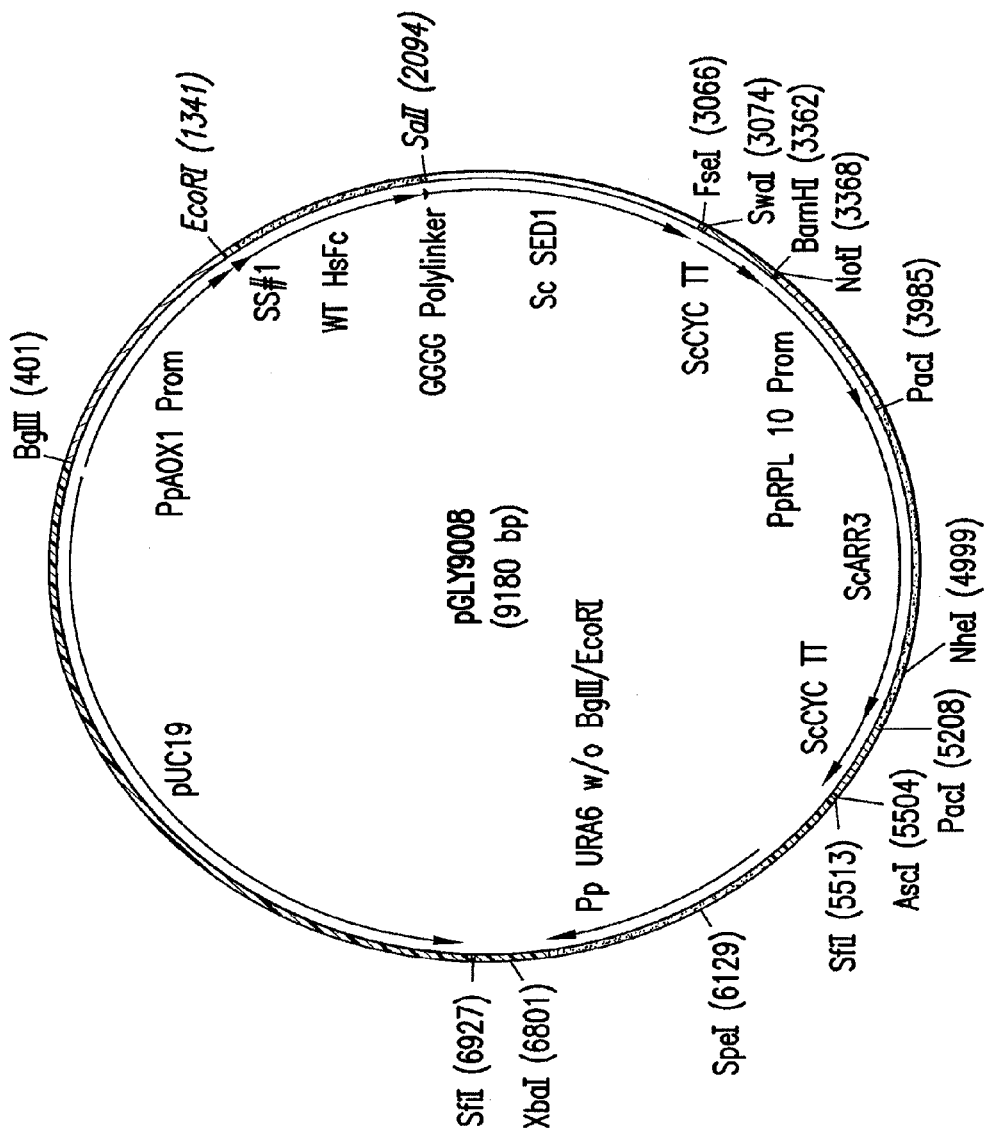
FIG. 2. Map of plasmid pGLY9008. The *Homo sapiens* Fc fused to *Saccharomyces cerevisiae* SED1 is driven by a *Pichia pastoris* AOX1 promoter.

To create the plasmid containing bait cassette, a codon optimized sequence of human IgG1 Fc fragment was synthesized using an EcoRI forward PCR primer containing the nucleic acid sequence of *S. cerevisiae* α-mating factor signal sequence fused upstream of the sequence encoding the IgG1 Fc N-terminus, and a SalI reverse primer encoding the C-terminus of IgG1 Fc that terminates in a sequence encoding a GGGG linker. A plasmid containing the anti-Her2 gene sequence was used as a PCR template for amplification of an EcoRI-α-mating factor signal sequence-Fc-GGGG-SalI fragment. Both PCR product and pGLY3033 (described in international publication no. WO09/111183) were digested using EcoRI and SalI endonucleases. The EcoRI-SalI fragment encoding the Fc was ligated in frame to EcoRI-SalI pGLY3033 backbone to generate plasmid pGLY9008 (FIG. 2). This plasmid enables delivery of the Fc-SEDT cassette under the control of the *Pichia pastoris* AOX1 promoter sequence. Like the parent plasmid it contains, the *Pichia pastoris* URA6 gene sequence, which serves as an integration locus in the genome, and the arsenite resistance gene, to allow selection on media containing sodium aresnite.

The pGLY3033 plasmid sequence comprises the nucleotide sequence:

(SEQ ID NO: 5)
TCGCGCGTTTCGGTGATGACGGTGAAAACCTCTGA

CACATGCAGCTCCCGGAGACGGTCACAGCTTGTCT

GTAAGCGGATGCCGGGAGCAGACAAGCCCGTCAGG

GCGCGTCAGCGGGTGTTGGCGGGTGTCGGGCTGG

CTTAACTATGCGGCATCAGAGCAGATTGTACTGAG

AGTGCACCATATGCGGTGTGAAATACCGCACAGAT

GCGTAAGGAGAAAATACCGCATCAGGCGCCATTCG

CCATTCAGGCTGCGCAACTGTTGGGAAGGGCGATC

GGTGCGGGCCTCTTCGCTATTACGCCAGCTGGCGA

AAGGGGGATGTGCTGCAAGGCGATTAAGTTGGGTA

ACGCCAGGGTTTTCCCAGTCACGACGTTGTAAAAC

GACGGCCAGTGAATTGAGATCTAACATCCAAAGAC

GAAAGGTTGAATGAAACCTTTTTGCCATCCGACAT

CCACAGGTCCATTCTCACACATAAGTGCCAAACGC

AACAGGAGGGATACACTAGCAGCAGACCGTTGCA

AACGCAGGACCTCCACTCCTCTTCTCCTCAACACC

CACTTTTGCCATCGAAAAACCAGCCCAGTTATTGG

GCTTGATTGGAGCTCGCTCATTCCAATTCCTTCTA

TTAGGCTACTAACACCATGACTTTATTAGCCTGTC

TATCCTGGCCCCCCTGGCGAGGTTCATGTTTGTTT

ATTTCCGAATGCAACAAGCTCCGCATTACACCCGA

ACATCACTCCAGATGAGGGCTTTCTGAGTGTGGGG

TCAFATAGTTTCATGTTCCCCAAATGGCCCAAAAC

TGACAGTTTAAACGCTGTCTTGGAACCTAATATGA

CAAAAGCGTGATCTCATCCAAGATGAACTAAGTTT

GGTTCGTTGAAATGCTAACGGCCAGTTGGTCAAAA

AGAAACTTCCAAAAGTCGGCATACCGTTTGTCTTG

TTTGGTATTGATTGACGAATGCTCAAAAATAATCT

CATTAATGCTTAGCGCAGTCTCTCTATCGCTTCTG

AACCCCGGTGCACCTGTGCCGAAACGCAAATGGGG

AAACACCCGCTTTTTGGATGATTATGCATTGTCTC

CACATTGTATGCTTCCAAGATTCTGGTGGGAATAC

TGCTGATAGCCTAACGTTCATGATCAAAATTTAAC

-continued

TGTTCTAACCCCTACTTGACAGCAATATATAAACA

GAAGGAAGCTGCCCTGTCTTAAACCTTTTTTTTTA

TCATCATTATTAGCTTACTTTCATAATTGCGACTG

GTTCCTATTGACTAGCTTTTGATTTTAACGACTTT

TTACGACAACTTGAGAAGATCAAAAAACAACTAAT

TATTCGAAACGGAATTCacgatggtcgcttggtgg tctttgtttctgtacggtcttcaggtcgctgcacc tgctttggctACTTCCAGATTGGAGGGATTGCAAT

CCGAAAACCACAGATTGAGAATGAAGATCACTGAG

TTGGACAAGGACTTGGAGGAAGTTACTATGCAGTT

GCAGGATGTTGGTGGTTGTGAGCAGAAGTTGATCT

CCGAAGAGGATTTGGTCGACCAATTCTCTAACTCT

ACTTCCGCTTCCTCTACTGACGTTACTTCCTCCTC

CTCTATTTCTACTTCCTCCGGTTCCGTTACTATTA

CTTCCTCTGAGGCTCCAGAATCTGACAACGGTACT

TCTACTGCTGCTCCAACTGAAACTTCTACTGAGGC

TCCTACTACTGCTATTCCAACTAACGGAACTTCCA

CAGAGGCTCCAACAACAGCTATCCCTACAAACGGT

ACATCCACTGAAGCTCCTACTGACACTACTACAGA

AGCTCCAACTACTGCTTTGCCTACTAATGGTACAT

CAACAGAGGCTCCTACAGATACAACAACTGAAGCT

CCAACAACTGGATTGCCAACAAACGGTACTACTTC

TGCTTTCCCACCAACTACTTCCTTGCCACCATCCA

ACACTACTACTACTCCACCATACAACCCATCCACT

GACTACACTACTGACTACACAGTTGTTACTGAGTA

CACTACTTACTGTCCAGAGCCAACTACTTTCACAA

CAAACGGAAAGACTTACACTGTTACTGAGCCTACT

ACTTTGACTATCACTGACTGTCCATGTACTATCGA

GAAGCAACTACTACTTCCACTACAGAGTATACTG

TTGTTACAGAATACACAACATATTGTCCTGAGCCA

ACAACATTCACTACTAATGGAAAAACATACACAGT

TACAGAACCAACTACATTGACAATTACAGATTGTC

CTTGTACAATTGAGAAGTCCGAGGCTCCTGAATCT

TCTGTTCCAGTTACTGAATCCAAGGGTACTACTAC

TAAAGAAACTGGTGTTACTACTAAGCAGACTACTG

CTAACCCATCCTTGACTGTTTCCACTGTTGTTCCA

GTTTCTTCCTCTGCTTCTTCCCACTCCGTTGTTAT

CAACTCCAACGGTGCTAACGTTGTTGTTCCTGGTG

CTTTGGGATTGGCTGGTGTTGCTATGTTGTTCTTG

TTATAGGGCCGGCCATTTAAATACAGGCCCCTTTT

CCTTTGTCGATATCATGTAATTAGTTATGTCACGC

```
TTACATTCACGCCCTCCTCCCACATCCGCTCTAAC

CGAAAAGGAAGGAGTTAGACAACCTGAAGTCTAGG

TCCCTATTTATTTTTTTTAATAGTTATGTTAGTAT

TAAGAACGTTATTTATATTTCAAATTTTTCTTTTT

TTTCTGTACAAACGCGTGTACGCATGTAACATTAT

ACTGAAAACCTTGCTTGAGAAGGTTTTGGGACGCT

CGAAGGCTTTAATTTGCAAGCTGGATCCGCGGCCG

CTTACGCGCCGTTCTTCGCTTGGTCTTGTATCTCC

TTACACTGTATCTTCCCATTTGCGTTTAGGTGGTT

ATCAAAAACTAAAAGGAAAAATTTCAGATGTTTAT

CTCTAAGGTTTTTCTTTTTACAGTATAACACGTG

ATGCGTCACGTGGTACTAGATTACGTAAGTTATTT

TGGTCCGGTGGGTAAGTGGGTAAGTATAGAAAGCA

TGTAGGTTTACAAAAACGCAGTCACGAATTATTGC

TACTTCGAGCTTGGAACCACCCCAAAGATTATATT

GTACTGATGCACTACCTTCTCGATTTTGCTCCTCC

AAGAACCTACGAAAAACATTTCTTGAGCCTTTTCA

ACCTAGACTACACATCAAGTTATTTAAGGTATGTT

CCGTTAACATGTAAGAAAAGGAGAGGATAGATCGT

TTATGGGGTACGTCGCCTGATTCAAGCGTGACCAT

TCGAAGAATAGGCCTTCGAAAGCTGAATAAAGCAA

ATGTCAGTTGCGATTGGTATGCTGACAAATTAGCA

TAAAAAGCAATAGACTTTCTAACCACCTGTTTTTT

TCCTTTTACTTTATTTATATTTTGCCACCGTACTA

ACAAGTTCAGACAAATTAATTAACACCATGTCAGA

AGATCAAAAAAGTGAAAATTCCGTACCTTCTAAGG

TTAATATGGTGAATCGCACCGATATACTGACTACG

ATCAAGTCATTGTCATGGCTTGACTTGATGTTGCC

ATTTACTATAATTCTCTCCATAATCATTGCAGTAA

TAATTTCTGTCTATGTGCCTTCTTCCCGTCACACT

TTTGACGCTGAAGGTCATCCCAATCTAATGGGAGT

GTCCATTCCTTTGACTGTTGGTATGATTGTAATGA

TGATTCCCCGATCTGCAAAGTTTCCTGGGAGTCT

ATTCACAAGTACTTCTACAGGAGCTATATAAGGAA

GCAACTAGCCCTCTCGTTATTTTGAATTGGGTCA

TCGGTCCTTTGTTGATGACAGCATTGGCGTGGATG

GCGCTATTCGATTATAAGGAATACCGTCAAGGCAT

TATTATGATCGGAGTAGCTAGATGCATTGCCATGG

TGCTAATTTGGAATCAGATTGCTGGAGGAGACAAT

GATCTCTGCGTCGTGCTTGTTATTACAAACTCGCT
```

```
TTTACAGATGGTATTATATGCACCATTGCAGATAT

TTTACTGTTATGTTATTTCTCATGACCACCTGAAT

ACTTCAAATAGGGTATTATTCGAAGAGGTTGCAAA

GTCTGTCGGAGTTTTTCTCGGCATACCACTGGGAA

TTGGCATTATCATACGTTGGGAAGTCTTACCATA

GCTGGTAAAAGTAATTATGAAAAATACATTTTGAG

ATTTATTTCTCCATGGGCAATGATCGGATTTCATT

ACACTTTATTTGTTATTTTTATTAGTAGAGGTTAT

CAATTTATCCACGAAATTGGTTCTGCAATATTGTG

CTTTGTCCCATTGGTGCTTTACTTCTTTATTGCAT

GGTTTTTGACCTTCGCATTAATGAGGTACTTATCA

ATATCTAGGAGTGATACACAAAGAGAATGTAGCTG

TGACCAAGAACTACTTTTAAAGAGGGTCTGGGGAA

GAAAGTCTTGTGAAGCTAGCTTTTCTATTACGATG

ACGCAATGTTTCACTATGGCTTCAAATAATTTTGA

ACTATCCCTGGCAATTGCTATTTCCTTATATGGTA

ACAATAGCAAGCAAGCAATAGCTGCAACATTTGGG

CCGTTGCTAGAAGTTCCAATTTTATTGATTTTGGC

AATAGTCGCGAGAATCCTTAAACCATATTATATAT

GGAACAATAGAAATTAATTAACAGGCCCCTTTTCC

TTTGTCGATATCATGTAATTAGTTATGTCACGCTT

ACATTCACGCCCTCCTCCCACATCCGCTCTAACCG

AAAAGGAAGGAGTTAGACAACCTGAAGTCTAGGTC

CCTATTTATTTTTTTAATAGTTATGTTAGTATTA

AGAACGTTATTTATATTTCAAATTTTTCTTTTTTT

TCTGTACAAACGCGTGTACGCATGTAACATTATAC

TGAAAACCTTGCTTGAGTAGGTTTTGGGACGCTCG

TAGGCTTTTATTTGCAAGCTGCGGCCTAAGGCGCG

CCAGGCCATAATGGCCCAAATGCAAGAGGACATTA

GAAATGTGTTTGGTAAGAACATGAAGCCGGAGGCA

TACAAACGATTCACAGATTTGAAGGAGGAAAACAA

ACTGCATCCACCGGAAGTGCCAGCAGCCGTGTATG

CCAACCTTGCTCTCAAAGGCATTCCTACGGATCTG

AGTGGGAAATATCTGAGATTCACAGACCCACTATT

GGAACAGTACCAAACCTAGTTTGGCCGATCCATGA

TTATGTAATGCATATAGTTTTTGTCGATGCTCACC

CGTTTCGAGTCTGTCTCGTATCGTCTTACGTATAA

GTTCAAGCATGTTTACCAGGTCTGTTAGAAACTCC

TTTGTGAGGGCAGGACCTATTCGTCTCGGTCCCGT

TGTTTCTAAGAGACTGTACAGCCAAGCGCAGAATG

GTGGCATTAACCATAAGAGGATTCTGATCGGACTT
```

-continued

GGTCTATTGGCTATTGGAACCACCCTTTACGGGAC

AACCAACCCTACCAAGACTCCTATTGCATTTGTGG

AACCAGCCACGGAAAGAGCGTTTAAGGACGGAGAC

GTCTCTGTGATTTTTGTTCTCGGAGGTCCAGGAGC

TGGAAAAGGTACCCAATGTGCCAAACTAGTGAGTA

ATTACGGATTTGTTCACCTGTCAGCTGGAGACTTG

TTACGTGCAGAACAGAAGAGGGAGGGGTCTAAGTA

TGGAGAGATGATTTCCCAGTATATCAGAGATGGAC

TGATAGTACCTCAAGAGGTCACCATTGCGCTCTTG

GAGCAGGCCATGTAGGAAAACTTCGAGAAAGGGAA

GACACGGTTCTTGATTGATGGATTCCCTCGTAAGA

TGGACCAGGCCAAAACTTTTGAGGAAAAAGTCGCA

AAGTCCAAGGTGACACTTTTCTTTGATTGTCCCGA

ATCAGTGCTCCTTGAGAGATTACTTAAAAGAGGAC

AGACAAGCGGAAGAGAGGATGATAATGCGGAGAGT

ATCAAAAAAGATTCAAAACATTCGTGGTAACTTC

GATGCCTGTGGTGGACTATTTCGGGAAGCAAGGAC

GCGTTTTGAAGGTATCTTGTGACCACCCTGTGGAT

CAAGTGTATTCACAGGTTGTGTCGGTGCTAAAAGA

GAAGGGGATCTTTGCCGATAACGAGACGGAGAATA

AATAAACATTGTAATAAGATTTAGACTGTGAATGT

TCTATGTAATATTTTTCGAGATACTGTATCTATCT

GGTGTACCGTATCACTCTGGACTTGCAAACTCATT

GATTACTTGTGCAATGGGCAAGAAGGATAGCTCTA

GAAAGAAGAAGAAAAAGGAGCCGCCTGAAGAGCTG

GATCTTTCCGAGGTTGTTCCAACTTTTGGTTATGA

GGAATTTCATGTTGAGCAAGAGGAGAATCCGGTCG

ATCAAGACGAACTTGACGGCCATAATGGCCTAGCT

TGGCGTAATCATGGTCATAGCTGTTTCCTGTGTGA

AATTGTTATCCGCTCACAATTCCACACAACATACG

AGCCGGAAGCATAAAGTGTAAAGCCTGGGGTGCCT

AATGAGTGAGCTAACTCACATTAATTGCGTTGCGC

TCACTGCCCGCTTTCCAGTCGGGAAACCTGTCGTG

CCAGCTGCATTAATGAATCGGCCAACGCGCGGGA

GAGGCGGTTTGCGTATTGGGCGCTCTTCCGCTTCC

TCGCTCACTGACTCGCTGCGCTCGGTCGTTCGGCT

GCGGCGAGCGGTATCAGCTCACTCAAAGGCGGTAA

TACGGTTATCCACAGAATCAGGGGATAACGCAGGA

AAGAACATGTGAGCAAAAGGCCAGCAAAAGGCCAG

GAACCGTAAAAAGGCCGCGTTGCTGGCGTTTTTCC

-continued

ATAGGCTCCGCCCCCCTGACGAGCATCACAAAAAT

CGACGCTCAAGTCAGAGGTGGCGAAACCCGACAGG

ACTATAAAGATACCAGGCGTTTCCCCCTGGAAGCT

CCCTCGTGCGCTCTCCTGTTCCGACCCTGCCGCTT

ACCGGATACCTGTCCGCCTTTCTCCCTTCGGGAAG

CGTGGCGCTTTCTCATAGCTCACGCTGTAGGTATC

TCAGTTCGGTGTAGGTCGTTCGCTCCAAGCTGGGC

TGTGTGCACGAACCCCCCGTTCAGCCCGACCGCTG

CGCCTTATCCGGTAACTATCGTCTTGAGTCCAACC

CGGTAAGACACGACTTATCGCCACTGGCAGCAGCC

ACTGGTAACAGGATTAGCAGAGCGAGGTATGTAGG

CGGTGCTACAGAGTTCTTGAAGTGGTGGCCTAACT

ACGGCTACACTAGAAGGACAGTATTTGGTATCTGC

GCTCTGCTGAAGCCAGTTACCTTCGGAAAAAGAGT

TGGTAGCTCTTGATCCGGCAAACAAACCACCGCTG

GTAGCGGTGGTTTTTTGTTTGCAAGCAGCAGATT

ACGCGCAGAAAAAAGGATCTCAAGAAGATCCTTT

GATCTTTTCTACGGGGTCTGACGCTCAGTGGAACG

AAAACTCACGTTAAGGGATTTTGGTCATGAGATTA

TCAAAAAGGATCTTCACCTAGATCCTTTTAAATTA

AAAATGAAGTTTTAAATCAATCTAAAGTATATATG

AGTAAACTTGGTCTGACAGTTACCAATGCTTAATC

AGTGAGGCACCTATCTCAGCGATCTGTCTATTTCG

TTCATCCATAGTTGCCTGACTCCCCGTCGTGTAGA

TAACTACGATACGGGAGGGCTTACCATCTGGCCCC

AGTGCTGCAATGATACCGCGAGACCCACGCTCACC

GGCTCCAGATTTATCAGCAATAAACCAGCCAGCCG

GAAGGGCCGAGCGCAGAAGTGGTCCTGCAACTTTA

TCCGCCTCCATCCAGTCTATTAATTGTTGCCGGGA

AGCTAGAGTAAGTAGTTCGCCAGTTAATAGTTTGC

GCAACGTTGTTGCCATTGCTACAGGCATCGTGGTG

TCACGCTCGTCGTTTGGTATGGCTTCATTCAGCTC

CGGTTCCCAACGATCAAGGCGAGTTACATGATCCC

CCATGTTGTGCAAAAAAGCGGTTAGCTCCTTCGGT

CCTCCGATCGTTGTCAGAAGTAAGTTGGCCGCAGT

GTTATCACTCATGGTTATGGCAGCACTGCATAATT

CTCTTACTGTCATGCCATCCGTAAGATGCTTTTCT

GTGACTGGTGAGTACTCAACCAAGTCATTCTGAGA

ATAGTGTATGCGGCGACCGAGTTGCTCTTGCCCGG

CGTCAATACGGGATAATACCGCGCCACATAGCAGA

ACTTTAAAAGTGCTCATCATTGGAAAACGTTCTTC

-continued

GGGGCGAAAACTCTCAAGGATCTTACCGCTGTTGA

GATCCAGTTCGATGTAACCCACTCGTGCACCCAAC

TGATCTTCAGCATCTTTTACTTTCACCAGCGTTTC

TGGGTGAGCAAAAACAGGAAGGCAAAATGCCGCAA

AAAAGGGAATAAGGGCGACACGGAAATGTTGAATA

CTCATACTCTTCCTTTTTCAATATTATTGAAGCAT

TTATCAGGGTTATTGTCTCATGAGCGGATACATAT

TTGAATGTATTTAGAAAAATAAACAAATAGGGGTT

CCGCGCACATTTCCCCGAAAAGTGCCACCTGACGT

CTAAGAAACCATTATTATCATGACATTAACCTATA

AAAATAGGCGTATCACGAGGCCCTTTCGTC

The pGLY9008 plasmid sequence comprises the nucleotide sequence:

(SEQ ID NO: 6)
TCGCGCGTTTCGGTGATGACGGTGAAAACCTCTGA

CACATGCAGCTCCCGGAGACGGTCACAGCTTGTCT

GTAAGCGGATGCCGGGAGCAGACAAGCCCGTCAGG

GCGCGTCAGCGGGTGTTGGCGGGTGTCGGGGCTGG

CTTAACTATGCGGCATCAGAGCAGATTGTACTGAG

AGTGCACCATATGCGGTGTGAAATACCGCACAGAT

GCGTAAGGAGAAAATACCGCATCAGGCGCCATTCG

CCATTCAGGCTGCGCAACTGTTGGGAAGGGCGATC

GGTGCGGGCCTCTTCGCTATTACGCCAGCTGGCGA

AAGGGGGATGTGCTGCAAGGCGATTAAGTTGGGTA

ACGCCAGGGTTTTCCCAGTCACGACGTTGTAAAAC

GACGGCCAGTGAATTGAGATCTAACATCCAAAGAC

GAAAGGTTGAATGAAACCTTTTTGCCATCCGACAT

CCACAGGTCCATTCTCACACATAAGTGCCAAACGC

AACAGGAGGGGATACACTAGCAGCAGACCGTTGCA

AACGCAGGACCTCCACTCCTCTTCTCCTCAACACC

CACTTTTGCCATCGAAAAACCAGCCCAGTTATTGG

GCTTGATTGGAGCTCGCTCATTCCAATTCCTTCTA

TTAGGCTACTAACACCATGACTTTATTAGCCTGTC

TATCCTGGCCCCCCTGGCGAGGTTCATGTTTGTTT

ATTTCCGAATGCAACAAGCTCCGCATTACACCCGA

ACATCACTCCAGATGAGGGCTTTCTGAGTGTGGGG

TCAAATAGTTTCATGTTCCCCAAATGGCCCAAAAC

TGACAGTTTAAACGCTGTCTTGGAACCTAATATGA

CAAAAGCGTGATCTCATCCAAGATGAACTAAGTTT

GGTTCGTTGAAATGCTAACGGCCAGTTGGTCAAAA

-continued
AGAAACTTCCAAAAGTCGGCATACCGTTTGTCTTG

TTTGGTATTGATTGACGAATGCTCAAAAATAATCT

CATTAATGCTTAGCGCAGTCTCTCTATCGCTTCTG

AACCCCGGTGCACCTGTGCCGAAACGCAAATGGGG

AAACACCCGCTTTTTGGATGATTATGCATTGTCTC

CACATTGTATGCTTCCAAGATTCTGGTGGGAATAC

TGCTGATAGCCTAACGTTCATGATCAAAATTTAAC

TGTTCTAACCCCTACTTGACAGCAATATATAAACA

GAAGGAAGCTGCCCTGTCTTAAACCTTTTTTTTTA

TCATCATTATTAGCTTACTTTCATAATTGCGACTG

GTTCCAATTGACAAGCTTTTGATTTTAACGACTTT

TAACGACAACTTGAGAAGATCAAAAAACAACTAAT

TATTCGAAACGGAATTCACGATGAGATTTCCTTCA

ATTTTTACTGCTGTTTTATTCGCAGCATCCTCCGC

ATTAGCTGACAAGACACATACTTGTCCACCATGTC

CAGCTCCAGAATTGTTGGGTGGTCCATCCGTTTTC

TTGTTCCCACCAAAGCCAAAGGACACTTTGATGAT

CTCCAGAACTCCAGAGGTTACATGTGTTGTTGTTG

ACGTTTCTCACGAGGACCCAGAGGTTAAGTTCAAC

TGGTACGTTGACGGTGTTGAAGTTCACAACGCTAA

GACTAAGCCAAGAGAAGAGCAGTACAACTCCACTT

ACAGAGTTGTTTCCGTTTTGACTGTTTTGCACCAG

GACTGGTTGAACGGTAAAGAATACAAGTGTAAGGT

TTCCAACAAGGCTTTGCCAGCTCCAATCGAAAAGA

CTATCTCCAAGGCTAAGGGTCAACCAAGAGAGCCA

CAGGTTTACACTTTGCCACCATCCAGAGAAGAGAT

GACTAAGAACCAGGTTTCCTTGACTTGTTTGGTTA

AAGGATTCTACCCATCCGACATTGCTGTTGAGTGG

GAATCTAACGGTCAACCAGAGAACAACTACAAGAC

TACTCCACCAGTTTTGGATTCTGATGGTTCCTTCT

TCTTGTACTCCAAGTTGACTGTTGACAAGTCCAGA

TGGCAACAGGGTAACGTTTTCTCCTGTTCCGTTAT

GCATGAGGCTTTGCACAACCACTACACTCAAAAGT

CCTTGTCTTTGTCCCCTGGTGGTGGTGGTGTCGAC

CAATTCTCTAACTCTACTTCCGCTTCCTCTACTGA

CGTTACTTCCTCCTCCTCTATTTCTACTTCCTCCG

GTTCCGTTACTATTACTTCCTCTGAGGCTCCAGAA

TCTGACAACGGTACTTCTACTGCTGCTCCAACTGA

AACTTCTACTGAGGCTCCTACTACTGCTATTCCAA

CTAACGGAACTTCCACAGAGGCTCCAACAACAGCT

ATCCCTACAAACGGTACATCCACTGAAGCTCCTAC

-continued

TGACACTACTACAGAAGCTCCAACTACTGCTTTGC
CTACTAATGGTACATCAACAGAGGCTCCTACAGAT
ACAACAACTGAAGCTCCAACAACTGGATTGCCAAC
AAACGGTACTACTTCTGCTTTCCCACCAACTACTT
CCTTGCCACCATCCAACACTACTACTACTCCACCA
TACAACCCATCCACTGACTACACTACTGACTACAC
AGTTGTTACTGAGTACACTACTTACTGTCCAGAGC
CAACTACTTTCACAACAAACGGAAAGACTTACACT
GTTACTGAGCCTACTACTTTGACTATCACTGACTG
TCCATGTACTATCGAGAAGCCAACTACTACTTCCA
CTACAGAGTATACTGTTGTTACAGAATACACAACA
TATTGTCCTGAGCCAACAACATTCACTACTAATGG
AAAAACATACACAGTTACAGAACCAACTACATTGA
CAATTACAGATTGTCCTTGTACAATTGAGAAGTCC
GAGGCTCCTGAATCTTCTGTTCCAGTTACTGAATC
CAAGGGTACTACTACTAAAGAAACTGGTGTTACTA
CTAAGCAGACTACTGCTAACCCATCCTTGACTGTT
TCCACTGTTGTTCCAGTTCTTCCTCTGCTTCTTC
CCACTCCGTTGTTATCAACTCCAACGGTGCTAACG
TTGTTGTTCCTGGTGCTTTGGGATTGGCTGGTGTT
GCTATGTTGTTCTTGTAATAGGGCCGGCCATTTAA
ATACAGGCCCCTTTTCCTTTGTCGATATCATGTAA
TTAGTTATGTCACGCTTACATTCACGCCCTCCTCC
CACATCCGCTCTAACCGAAAAGGAAGGAGTTAGAC
AACCTGAAGTCTAGGTCCCTATTTATTTTTTTAA
TAGTTATGTTAGTATTAAGAACGTTATTTATATTT
CAAATTTTTCTTTTTTTCTGTACAAACGCGTGTA
CGCATGTAACATTATACTGAAAACCTTGCTTGAGA
AGGTTTTGGGACGCTCGAAGGCTTTAATTTGCAAG
CTGGATCCGCGGCCGCTTACGCGCCGTTCTTCGCT
TGGTCTTGTATCTCCTTACACTGTATCTTCCCATT
TGCGTTTAGGTGGTTATCAAAAACTAAAAGGAAAA
ATTTCAGATGTTTATCTCTAAGGTTTTTTCTTTTT
ACAGTATAACACGTGATGCGTCACGTGGTACTAGA
TTACGTAAGTTATTTTGGTCCGGTGGGTAAGTGGG
TAAGAATAGAAAGCATGAAGGTTTACAAAAACGCA
GTCACGAATTATTGCTACTTCGAGCTTGGAACCAC
CCCAAAGATTATATTGTACTGATGCACTACCTTCT
CGATTTTGCTCCTCCAAGAACCTACGAAAAACATT
TCTTGAGCCTTTTCAACCTAGACTACACATCAAGT

-continued

TATTTAAGGTATGTTCCGTTAACATGTAAGAAAAG
GAGAGGATAGATCGTTTATGGGGTACGTCGCCTGA
TTCAAGCGTGACCATTCGAAGAATAGGCCTTCGAA
AGCTGAATAAAGCAAATGTCAGTTGCGATTGGTAT
GCTGACAAATTAGCATAAAAAGCAATAGACTTTCT
AACCACCTGTTTTTTCCTTTTACTTTATTTATAT
TTTGCCACCGTACTAACAAGTTCAGACAAATTAAT
TAACACCATGTCAGAAGATCAAAAAAGTGAAAATT
CCGTACCTTCTAAGGTTAATATGGTGAATCGCACC
GATATACTGACTACGATCAAGTCATTGTCATGGCT
TGACTTGATGTTGCCATTTACTATAATTCTCTCCA
TAATCATTGCAGTAATAATTTCTGTCTATGTGCCT
TCTTCCCGTCACACTTTTGACGCTGAAGGTCATCC
CAATCTAATGGGAGTGTCCATTCCTTTGACTGTTG
GTATGATTGTAATGATGATTCCCCCGATCTGCAAA
GTTTCCTGGGAGTCTATTCACAAGTACTTCTACAG
GAGCTATATAAGGAAGCAACTAGCCCTCTCGTTAT
TTTTGAATTGGGTCATCGGTCCTTTGTTGATGACA
GCATTGGCGTGGATGGCGCTATTCGATTATAAGGA
ATACCGTCAAGGCATTATTATGATCGGAGTAGCTA
GATGCATTGCCATGGTGCTAATTTGGAATCAGATT
GCTGGAGGAGACAATGATCTCTGCGTCGTGCTTGT
TATTACAAACTCGCTTTTACAGATGGTATTATATG
CACCATTGCAGATATTTTACTGTTATGTTATTTCT
CATGACCACCTGAATACTTCAAATAGGGTATTATT
CGAAGAGGTTGCAAAGTCTGTCGGAGTTTTTCTCG
GCATACCACTGGGAATTGGCATTATCATACGTTTG
GGAAGTCTTACCATAGCTGGTAAAAGTAATTATGA
AAAATACATTTTGAGATTATTTCTCCATGGGCAA
TGATCGGATTTCATTACACTTTATTTGTTATTTTT
ATTAGTAGAGGTTATCAATTTATCCACGAAATTGG
TTCTGCAATATTGTGCTTTGTCCCATTGGTGCTTT
ACTTCTTTATTGCATGGTTTTTGACCTTCGCATTA
ATGAGGTACTTATCAATATCTAGGAGTGATACACA
AAGAGAATGTAGCTGTGACCAAGAACTACTTTTAA
AGAGGGTCTGGGAAGAAAGTCTTGTGAAGCTAGC
TTTTCTATTACGATGACGCAATGTTTCACTATGGC
TTCAAATAATTTTGAACTATCCCTGGCAATTGCTA
TTTCCTTATATGGTAACAATAGCAAGCAAGCAATA
GCTGCAACATTTGGGCCGTTGCTAGAAGTTCCAAT
TTTATTGATTTTGGCAATAGTCGCGAGAATCCTTA

-continued

AACCATATTATATATGGAACAATAGAAATTAATTA

ACAGGCCCCTTTTCCTTTGTCGATATCATGTAATT

AGTTATGTCACGCTTACATTCACGCCCTCCTCCCA

CATCCGCTCTAACCGAAAAGGAAGGAGTTAGACAA

CCTGAAGTCTAGGTCCCTATTTATTTTTTTAATA

GTTATGTTAGTATTAAGAACGTTATTTATATTTCA

AATTTTTCTTTTTTTTCTGTACAAACGCGTGTACG

CATGTAACATTATACTGAAAACCTTGCTTGAGAAG

GTTTTGGGACGCTCGAAGGCTTTAATTTGCAAGCT

GCGGCCTAAGGCGCGCCAGGCCATAATGGCCCAAA

TGCAAGAGGACATTAGAAATGTGTTTGGTAAGAAC

ATGAAGCCGGAGGCATACAAACGATTCACAGATTT

GAAGGAGGAAAACAAACTGCATCCACCGGAAGTGC

CAGCAGCCGTGTATGCCAACCTTGCTCTCAAAGGC

ATTCCTACGGATCTGAGTGGGAAATATCTGAGATT

CACAGACCCACTATTGGAACAGTACCAAACCTAGT

TTGGCCGATCCATGATTATGTAATGCATATAGTTT

TTGTCGATGCTCACCCGTTTCGAGTCTGTCTCGTA

TCGTCTTACGTATAAGTTCAAGCATGTTTACCAGG

TCTGTTAGAAACTCCTTTGTGAGGGCAGGACCTAT

TCGTCTCGGTCCCGTTGTTTCTAAGAGACTGTACA

GCCAAGCGCAGAATGGTGGCATTAACCATAAGAGG

ATTCTGATCGGACTTGGTCTATTGGCTATTGGAAC

CACCCTTTACGGGACAACCAACCCTACCAAGACTC

CTATTGCATTTGTGGAACCAGCCACGGAAAGAGCG

TTTAAGGACGGAGACGTCTCTGTGATTTTTGTTCT

CGGAGGTCCAGGAGCTGGAAAAGGTACCCAATGTG

CCAAACTAGTGAGTAATTACGGATTTGTTCACCTG

TCAGCTGGAGACTTGTTACGTGCAGAACAGAAGAG

GGAGGGGTCTAAGTATGGAGAGATGATTTCCCAGT

ATATCAGAGATGGACTGATAGTACCTCAAGAGGTC

ACCATTGCGCTCTTGGAGCAGGCCATGAAGGAAAA

CTTCGAGAAAGGGAAGACACGGTTCTTGATTGATG

GATTCCCTCGTAAGATGGACCAGGCCAAAACTTTT

GAGGAAAAAGTCGCAAAGTCCAAGGTGACACTTTT

CTTTGATTGTCCCGAATCAGTGCTCCTTGAGAGAT

TACTTAAAAGAGGACAGACAAGCGGAAGAGAGGAT

GATAATGCGGAGAGTATCAAAAAAAGATTCAAAAC

ATTCGTGGAAACTTCGATGCCTGTGGTGGACTATT

TCGGGAAGCAAGGACGCGTTTTGAAGGTATCTTGT

-continued

GACCACCCTGTGGATCAAGTGTATTCACAGGTTGT

GTCGGTGCTAAAAGAGAAGGGGATCTTTGCCGATA

ACGAGACGGAGAATAAATAAACATTGTAATAAGAT

TTAGACTGTGAATGTTCTATGTAATATTTTTCGAG

ATACTGTATCTATCTGGTGTACCGTATCACTCTGG

ACTTGCAAACTCATTGATTACTTGTGCAATGGGCA

AGAAGGATAGCTCTAGAAAGAAGAAGAAAAAGGAG

CCGCCTGAAGAGCTGGATCTTTCCGAGGTTGTTCC

AACTTTTGGTTATGAGGAATTTCATGTTGAGCAAG

AGGAGAATCCGGTCGATCAAGACGAACTTGACGGC

CATAATGGCCTAGCTTGGCGTAATCATGGTCATAG

CTGTTTCCTGTGTGAAATTGTTATCCGCTCACAAT

TCCACACAACATACGAGCCGGAAGCATAAAGTGTA

AAGCCTGGGGTGCCTAATGAGTGAGCTAACTCACA

TTAATTGCGTTGCGCTCACTGCCCGCTTTCCAGTC

GGGAAACCTGTCGTGCCAGCTGCATTAATGAATCG

GCCAACGCGCGGGGAGAGGCGGTTTGCGTATTGGG

CGCTCTTCCGCTTCCTCGCTCACTGACTCGCTGCG

CTCGGTCGTTCGGCTGCGGCGAGCGGTATCAGCTC

ACTCAAAGGCGGTAATACGGTTATCCACAGAATCA

GGGGATAACGCAGGAAAGAACATGTGAGCAAAAGG

CCAGCAAAAGGCCAGGAACCGTAAAAAGGCCGCGT

TGCTGGCGTTTTTCCATAGGCTCCGCCCCCCTGAC

GAGCATCACAAAAATCGACGCTCAAGTCAGAGGTG

GCGAAACCCGACAGGACTATAAAGATACCAGGCGT

TTCCCCCTGGAAGCTCCCTCGTGCGCTCTCCTGTT

CCGACCCTGCCGCTTACCGGATACCTGTCCGCCTT

TCTCCCTTCGGGAAGCGTGGCGCTTTCTCATAGCT

CACGCTGTAGGTATCTCAGTTCGGTGTAGGTCGTT

CGCTCCAAGCTGGGCTGTGTGCACGAACCCCCCGT

TCAGCCCGACCGCTGCGCCTTATCCGGTAACTATC

GTCTTGAGTCCAACCCGGTAAGACACGACTTATCG

CCACTGGCAGCAGCCACTGGTAACAGGATTAGCAG

AGCGAGGTATGTAGGCGGTGCTACAGAGTTCTTGA

AGTGGTGGCCTAACTACGGCTACACTAGAAGGACA

GTATTTGGTATCTGCGCTCTGCTGAAGCCAGTTAC

CTTCGGAAAAAGAGTTGGTAGCTCTTGATCCGGCA

AACAAACCACCGCTGGTAGCGGTGGTTTTTTTGTT

TGCAAGCAGCAGATTACGCGCAGAAAAAAAGGATC

TCAAGAAGATCCTTTGATCTTTTCTACGGGGTCTG

ACGCTCAGTGGAACGAAAACTCACGTTAAGGGATT

-continued

```
TTGGTCATGAGATTATCAAAAAGGATCTTCACCTA

GATCCTTTTAAATTAAAAATGAAGTTTTAAATCAA

TCTAAAGTATATATGAGTAAACTTGGTCTGACAGT

TACCAATGCTTAATCAGTGAGGCACCTATCTCAGC

GATCTGTCTATTTCGTTCATCCATAGTTGCCTGAC

TCCCCGTCGTGTAGATAACTACGATACGGGAGGGC

TTACCATCTGGCCCCAGTGCTGCAATGATACCGCG

AGACCCACGCTCACCGGCTCCAGATTTATCAGCAA

TAAACCAGCCAGCCGGAAGGGCCGAGCGCAGAAGT

GGTCCTGCAACTTTATCCGCCTCCATCCAGTCTAT

TAATTGTTGCCGGGAAGCTAGAGTAAGTAGTTCGC

CAGTTAATAGTTTGCGCAACGTTGTTGCCATTGCT

ACAGGCATCGTGGTGTCACGCTCGTCGTTTGGTAT

GGCTTCATTCAGCTCCGGTTCCCAACGATCAAGGC

GAGTTACATGATCCCCCATGTTGTGCAAAAAGCG

GTTAGCTCCTTCGGTCCTCCGATCGTTGTCAGAAG

TAAGTTGGCCGCAGTGTTATCACTCATGGTTATGG

CAGCACTGCATAATTCTCTTACTGTCATGCCATCC

GTAAGATGCTTTTCTGTGACTGGTGAGTACTCAAC

CAAGTCATTCTGAGAATAGTGTATGCGGCGACCGA

GTTGCTCTTGCCCGGCGTCAATACGGGATAATACC

GCGCCACATAGCAGAACTTTAAAAGTGCTCATCAT

TGGAAAACGTTCTTCGGGGCGAAAACTCTCAAGGA

TCTTACCGCTGTTGAGATCCAGTTCGATGTAACCC

ACTCGTGCACCCAACTGATCTTCAGCATCTTTTAC

TTTCACCAGCGTTTCTGGGTGAGCAAAAACAGGAA

GGCAAAATGCCGCAAAAAAGGGAATAAGGGCGACA

CGGAAATGTTGAATACTCATACTCTTCCTTTTTCA

ATATTATTGAAGCATTTATCAGGGTTATTGTCTCA

TGAGCGGATACATATTTGAATGTATTTAGAAAAAT

AAACAAATAGGGGTTCCGCGCACATTTCCCCGAAA

AGTGCCACCTGACGTCTAAGAAACCATTATTATCA

TGACATTAACCTATAAAAATAGGCGTATCACGAGG

CCCTTTCGTC
```

To test the capacity of this configuration for displaying monovalent antibody fragments (comprising human IgGs) (1 heavy chain immunoglobulin and 1 light chain immunoglobulin (H+L)) on the yeast cell wall, pGLY9008 was introduced into GFI 5.0 strains that have been previously selected as expression hosts of human anti-Her2 or anti-PCSK9 IgGs. An empty strain was included as a control (Table 1).

TABLE 1

| Yeast Strains | |
|---|---|
| Strain | mAb |
| YGLY8316 | Empty |
| YGLY18483 | Anti-PCSK9 (AX189) |
| YGLY18281 | Anti-PCSK9 (AX132) |
| YGLY14755 | Anti-PCSK9 (1DG) |
| YGLY13979 | Anti-Her2 |
| YGLY14836 | Anti-Her2 |

*These Pichia pastoris strains form part of the present invention

The glycoengineered Pichia pastoris monoclonal antibody production strains in Table 1 were grown in 50 mL BMGY media until the culture optical density, at 600 nm, was 2. The cells were washed three times with 1 M sorbitol and resuspended in 1 mL 1 M sorbitol. About 1-2 micrograms of SpeI linearized pGLY9008 was mixed with these competent cells. Transformation was performed with a Bio-Rad electroporation apparatus using the manufacturer's program specific for electroporation of nucleic acids into Pichia pastoris. One mL recovery media was added to the cells, which were then plated out on yeast-soytone-dextrose (YSD) media with 50 μg/mL arsenite.

Growth and Induction of Fc-Monovalent Antibody Fragment (H+L) Displaying Yeast.

Figure 3A:
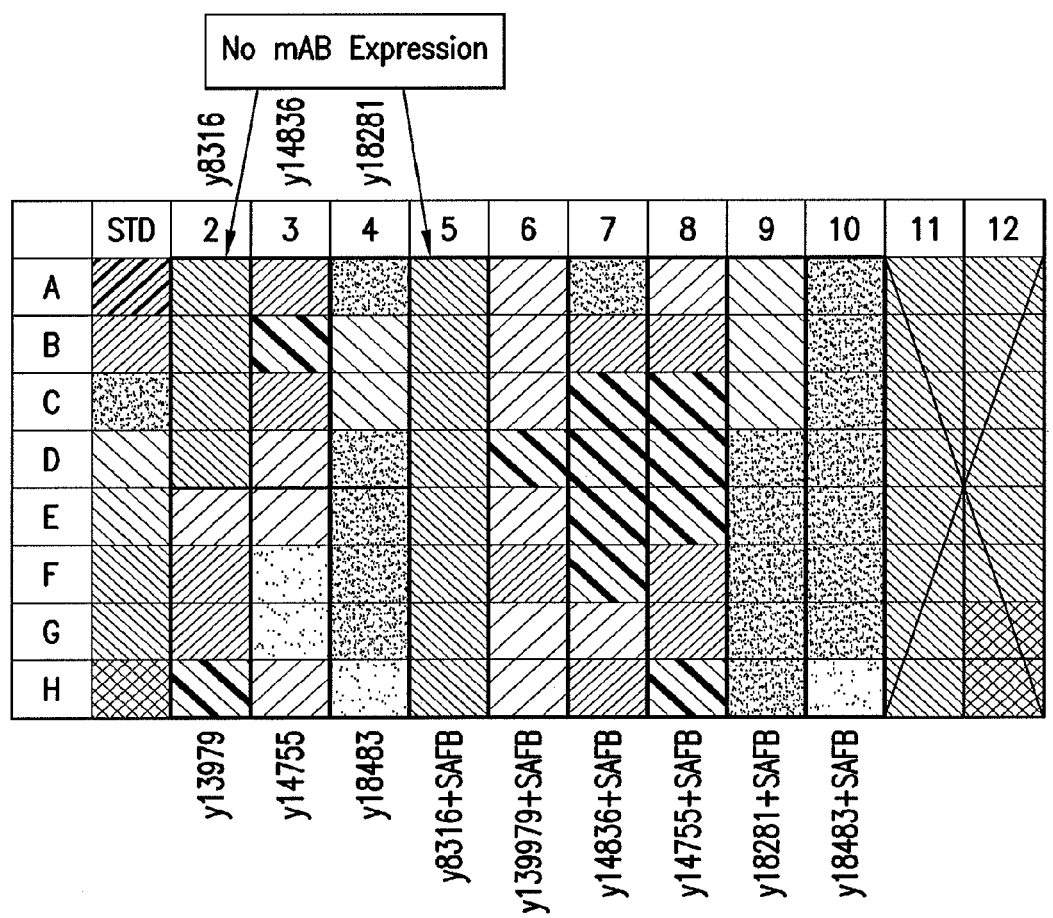
FIGS. 3a-3c. (a) ELISA measuring the concentration of Kappa light chain was used to determine the concentration of secreted antibodies from the strains explained in Table 1. Lane 1 was serially diluted ELISA standard; Lanes 2-3 contained material generated by strains in Table 1 without the surface anchored Fc bait (SAFE); Lanes 5-10 contained the same strains plus SAFE. Y8316 did not express antibodies and was used as a negative control. (b) Supernatants generated by the strains in 3a were run on Protein A columns to capture secreted antibodies. Eluted IgGs were run on (c) non-reducing SDS-PAGE.
Figure 3B:
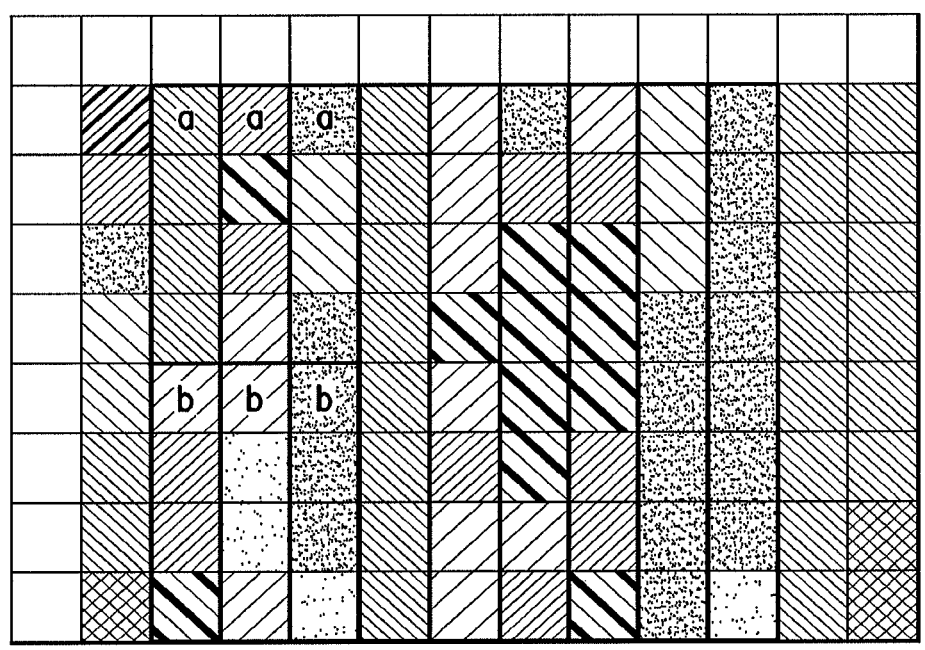
Figure 3C:
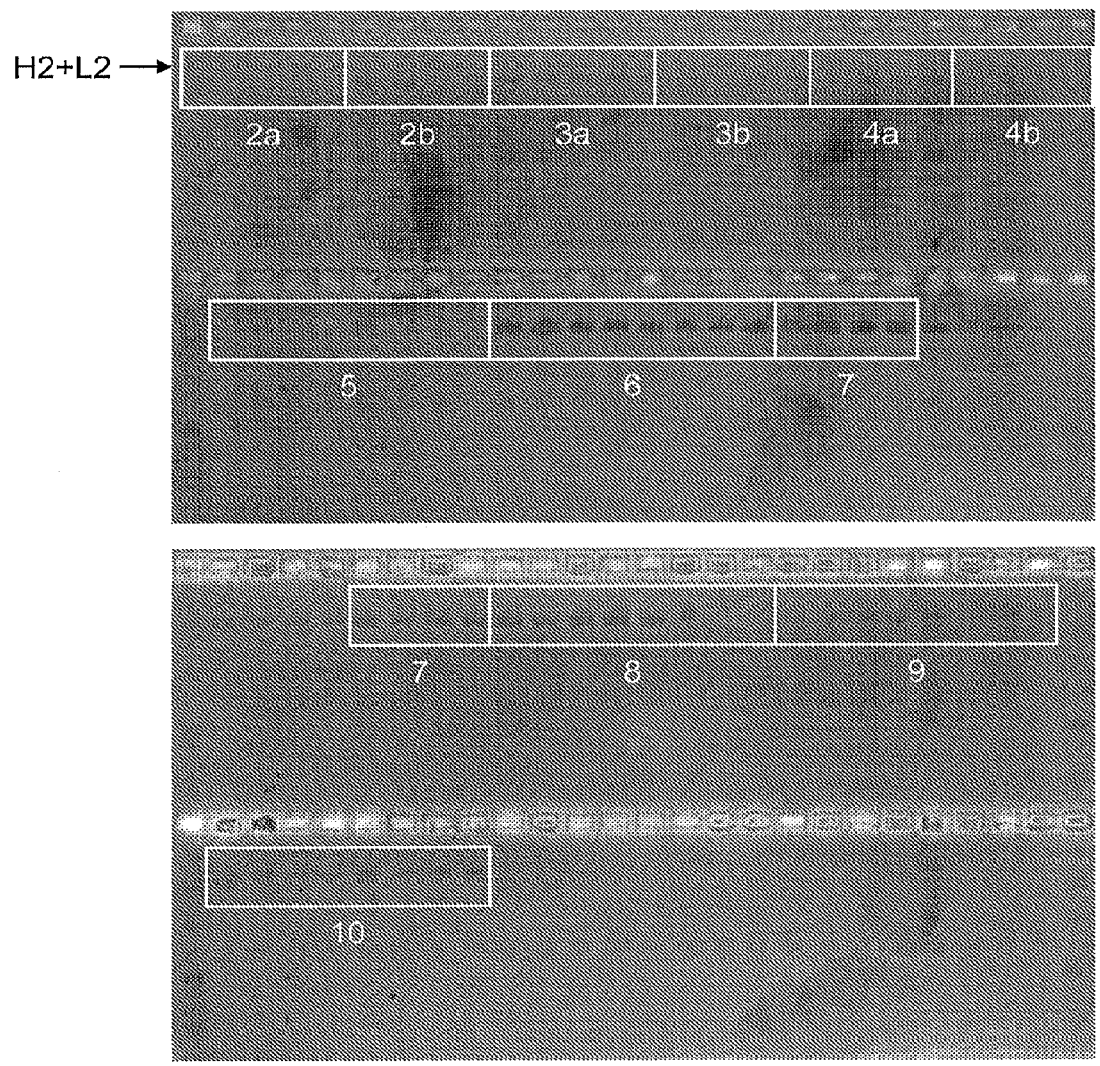

Glycoengineered yeast expressing human IgGs and the Fc-SED1 bait expression cassette were inoculated using 600 μL BMGY in a 96 deep well plate or 50 mL BMGY in a 250 mL shake flasks for two days. The cells were collected by centrifugation and the supernatant was discarded. The cells were induced by incubation in 300 μL or 25 mL BMMY with PMTi inhibitor overnight following the methods described in international application publication no. WO2007/061631. Following induction, culture supernatants were assayed for antibody expression using Kappa ELISA, according to the manufacturer's protocol, and Protein A capture SDS-PAGE analysis. The data in FIGS. 3a and b, respectively, describe the results of both of these assays. As outlined in FIG. 3, supernatants of cultures containing the Fc-Sed1 protein bait were found to contain similar levels of secreted full antibody molecules (2 heavy chain immunoglobulins and 2 light chain immunoglobulins ((H2+L2)) compared to their parent strains (containing no Fc-Sed1p). This indicated that the presence of the Fc-Sed1p bait did not interfere with the yeast ability to secret full IgG antibodies (H2+L2).

To determine the efficiency of surface displaying antibodies using this method, cells were labeled with APC 635 labeled mouse anti-Human Kappa, which detects the light chain of human antibody molecules, and were processed by flow cytometry. Briefly, each culture, after growth to an optical density, at 600 nm, of 2, was pelleted by centrifugation and washed in 100 μL PBS. Cells were incubated for 30 minutes at room temperature (RT) in 100 μL phosphate buffer saline (PBS) containing fluorescently labeled (APC635) mouse anti-human Kappa light chain and washed in 100 μl PBS. One hundred microliters of PBS was used to resuspend pellets before analyzing in a flow cytometer.

Figure 4A:
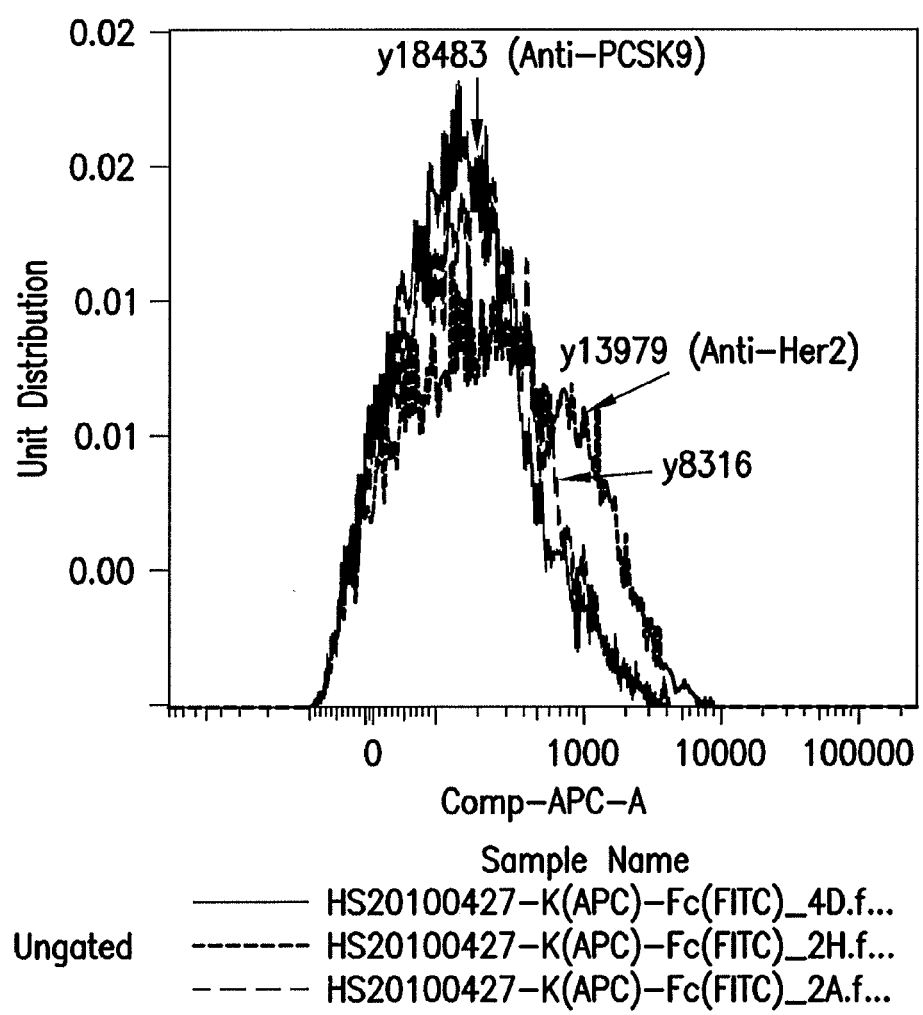
FIGS. 4a-4c. Figure shows FACS data demonstrating the different fluorescence intensities observed between various *Pichia pastoris* strains. (a) parental strains expressing anti-HER2 and anti-PCSK9 with no Fc-SED1 bait; (b) anti-Her2 displaying cells with and without the bait; (c) anti-PCSK9 displaying cells with and without bait.
Figure 4B:
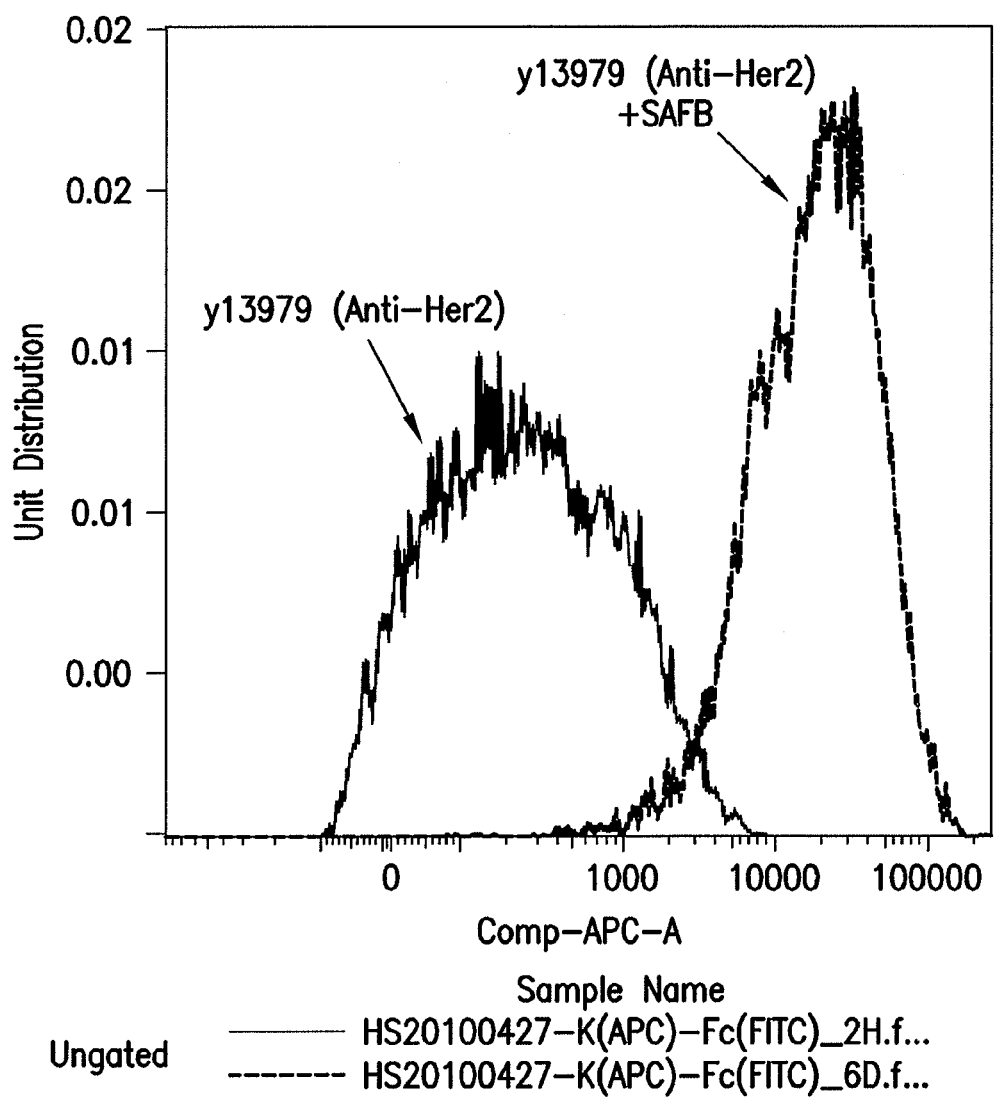
Figure 4C:
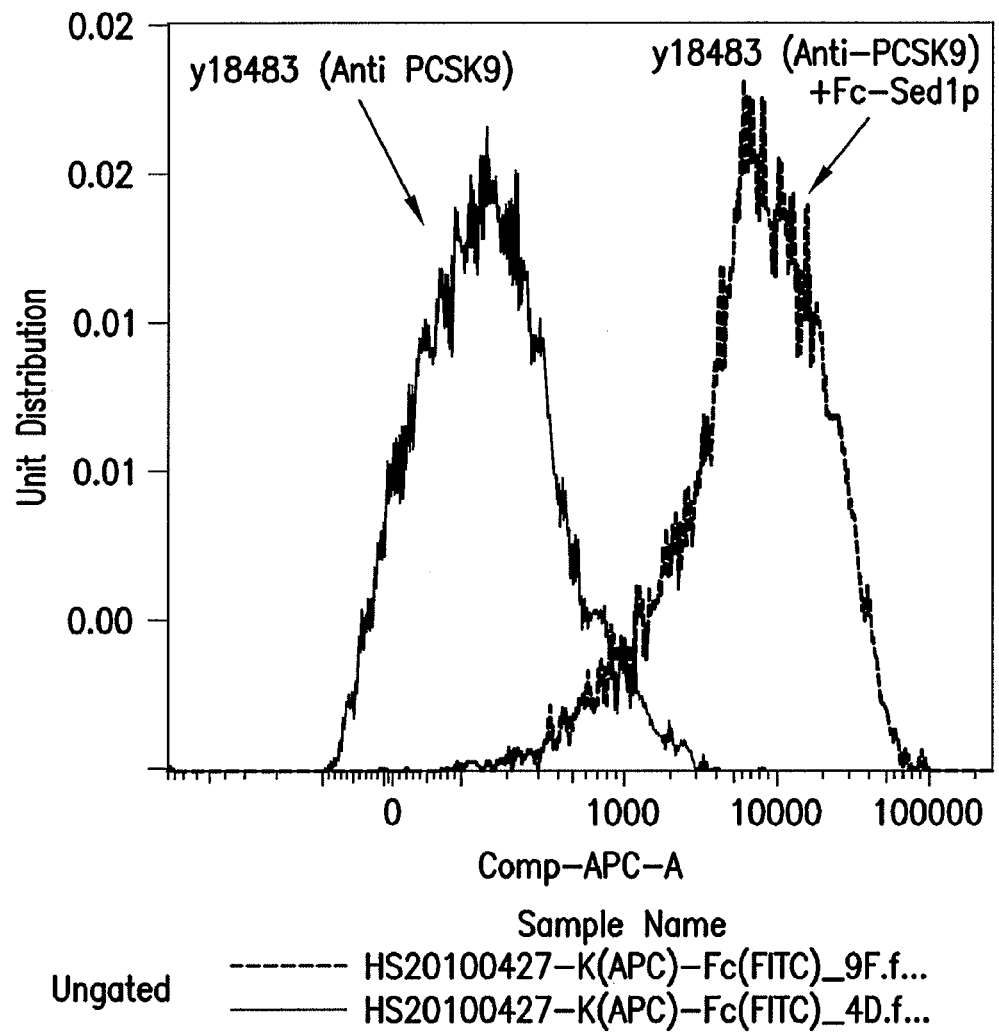

Flow cytometry analysis was conducted using the cells co-expressing Fc-Sed1p bait and anti-Her2, or Fc-Sed1p bait and anti-PCSK9. Controls were prepared in which an empty strain expressing Fc-Sed1p bait only or a strain that expressed full length antibody (H2+L2) without the Fc-Sed1p. Strains co-expressing anti-Her2 or anti-PCSK9 with the Fc-Sed1p bait were found to display significant levels of anti-Kappa binding while strains lacking the Fc-Sed1p bait showed background signal levels. In FIG. 4a-c, the fluorescent intensities from these experiments were compared. The Figure shows these different fluorescence intensities between the anti-Her2 displaying cells and the anti-PCSK9 displaying cells, and the parent strains that did not contain the Fc-Sed1p bait. It is noteworthy to mention that anti-Her2 displaying cells showed higher fluorescence intensity than the anti-PCSK9 displaying cells. These results were in congruence with what was known regarding expression levels of these two antibodies.

Figure 5:
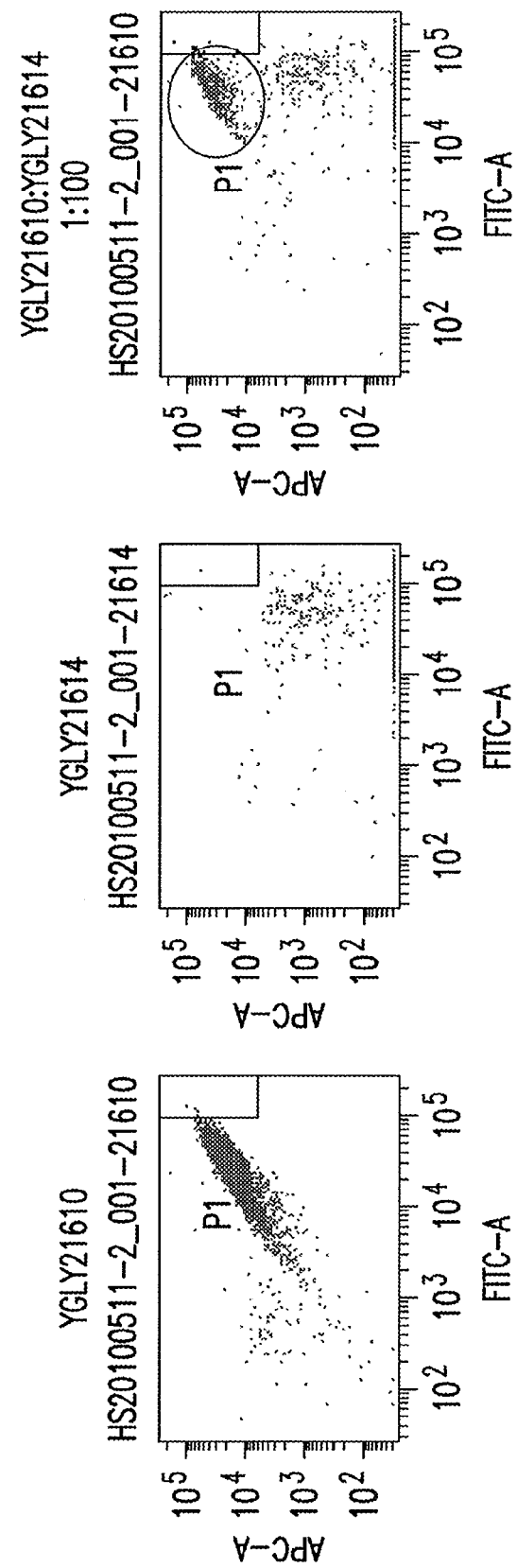
FIG. 5. FACS analysis of labeled *Pichia pastoris* yeast strains YGLY21610 and YGLY21614 displaying an Fc-Sed1p complexed with an anti-PCSK9 monovalent antibody fragment (H+L) or an anti-Her2 (H+L) monovalent antibody fragment. The cells were dually labeled with goat anti-human Fc Alexa 488, biotinylated PCSK9, and APC 635 labeled Streptavidin. The cells were analyzed separately (left and middle panels, respectively) and mixed together in a 1:00 ratio (right panel). The points representing the YGLY21610 cells in the right panel are circled.

To establish the utility of this method for separating antibody mixtures, fluorescence-activated cell sorting (FACS) of a mixture of cells displaying Fc-Sed1p anti-PCSK9 monovalent antibody fragment (H+L) (strain YGLY21610) and Fc-Sed1p anti-Her2 (H+L) (strain YGLY21614) was performed as follows. The cells displaying anti-PCSK9 (H+L) and cells displaying anti-Her2 (H+L) were mixed together in the following ratio 1:0; 0:1; and 1:100. Cells were dually labeled with goat anti-human Fc Alexa 488 and 100 nM biotinylated PCSK9 and APC 635 labeled Streptavidin. FIG. 5 shows that Fc-Sed1p/anti-PCSK9 (H+L) was able to bind biotinylated PCSK9 while Fc-Sed1p/anti-Her2 (H+L) was not. Both strains reacted with anti-human Fc Alexa 488 antibody. Two separate populations of cells were visible when cells from both cultures were mixed at a 1:100 ratio of Fc-Sed1p anti-PCSK9 displaying cells (circled) to Fc-Sed1p anti-Her2 displaying cells. The number of PCSK9 binders in this mixture was in agreement with the 1:100 ratio, thus lending further support for the robustness of this method in screening antibodies with desired antigen-binding.

The above experiments demonstrated that the Fc-Sed1p antibody display system can be used to display IgG monovalent antibody fragments (H+L) that retain specific antigen binding of their corresponding full antibody molecules (H2+L2) dimers. The next goal was to use this method to isolate and enrich for novel antibody molecules that can bind to any antigen of interest. To this end we took advantage of two recently constructed libraries. Library one was constructed by changing the sequence of the heavy chain of anti-PCSK9 antibody AX189 while marinating the original light chain sequence. This library had a diversity of about 2500 unique sequences and will be referred to as "BP550". The second library was generated by maintaining the original AX189 heavy chain sequence and changing the light chain sequence. This library contained about 4000 unique sequences and will be referred to as "BP551".

BP550 and BP551 were transformed as described previously into strain YGLY21605 (empty 5.0 strain carrying pGLY9008-expressing Fc-Sed1p) and plated out on YSD containing 300 micrograms per milliliter zeocin. Approximately, 50,000 colonies were obtained for each transformation, thus providing ample statistical coverage of all possible sequences in the libraries. The colonies resulting from transforming the two libraries were scraped off the solid media and inoculated separately in 250 mL shake flasks containing 50 mL of YSG liquid medium with 300μ/mL zeocin. The cultures were passaged 3 times by re-inoculating 1 mL of each culture into the fresh selective liquid media (YSG+zeocin). The third passages were allowed to grow to saturation in YSG media and induced in 25 mL BMMY with PMTi inhibitor (PMTi4: L000001772; at a concentration of 1 micrograms/ml) overnight following the methods described in international patent publication no. WO2007/061631. Strains YGLY21610 (Fc-Sed1p anti-PCSK9 (AX189)) and YGLY21614 (Fc-Sed1p anti-Her2) were included as positive and negative controls, respectively.

After 24 hours of induction, each of the four cultures were grown to an optical density, at 600 nm, of 2. Pellets were collected by centrifugation and washed with 100 μL 1×PBS then labeled in 100 μL PBS containing anti-Kappa Alexa 488 and 100 nM of biotin-PCSK9. Mixtures were incubated at room temperature for 30 minutes then washed with 100 μL PBS solution. Cells were incubated at room temperature with APC 635 labeled Streptavidin in 100 μL PBS for 10 minutes and washed 2× in PBS and submitted for FACS.

Using the flow cytometer dot plots generated with YGLY21610 and YGLY21614 as boundaries to gate potential binders, clones from 100,000 cells of populations of both libraries, BP550 and BP551, were sorted in a FACS sorter and collected in 5 mL YSG media. Cultures were allowed to recover by shaking at room temperature for 5 days. Sorting round 1 pools were re-inoculated in 50 mL YSG liquid media and the same process was repeated to induce and label the cultures. Another round of sorting (round 2) was conducted on the round 1 pool and cells were collected as above and induced. To obtain single colonies, 1000 cells of both two-round sorted populations (BP550 and BP551) were plated out of solid media and were analyzed by Kappa ELISA and PCSK9 affinity ELISA to determine protein titer and binding affinities for PCSK9, respectively. Additionally, a yeast colony PCR amplification reaction was performed to amplify heavy chain and light chain genes of the round 2 clones which were submitted for DNA sequence analysis.

Figure 6:
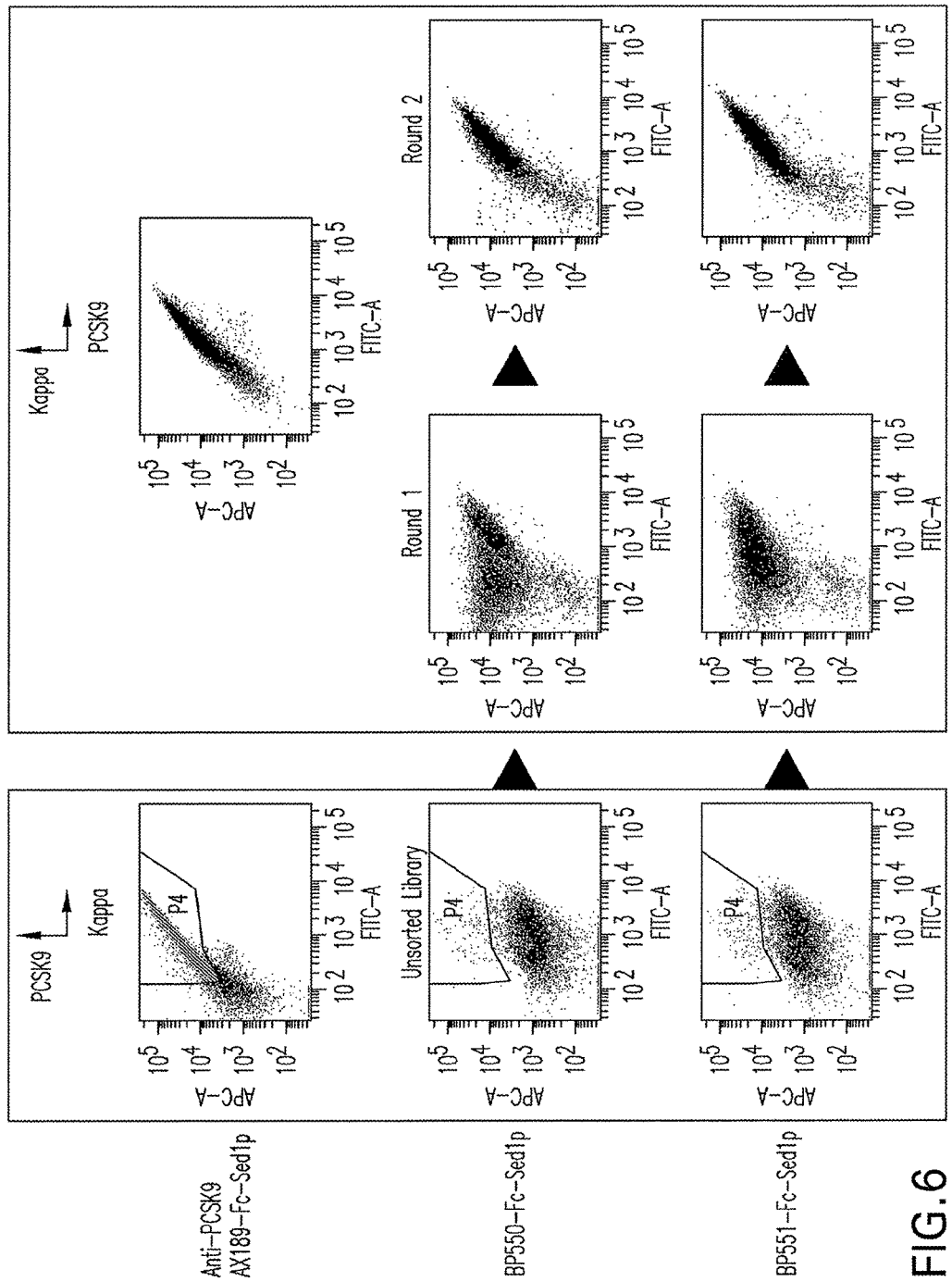
FIG. 6. FACS analysis of *Pichia pastoris* cells expressing the Fc-SED1 bait and; (1) anti-PCSK9 antibody AX189 heavy and light chains (Anti-PCSK9; AX189-Fc-Sed1p); or (2) AX189 light chain and heavy chain from the BP550 library (BP550-Fc-Sed1p); or (3) AX189 heavy chain and light chain from the BP551 library (BP551-Fc-Sed1p). The left panel shows data relating to unsorted strains containing the library, and the right panel shows data relating to cells containing the library that were sorted once or twice. FACS data relating to the control AX189 expressing cells are also shown.
Figure 8:
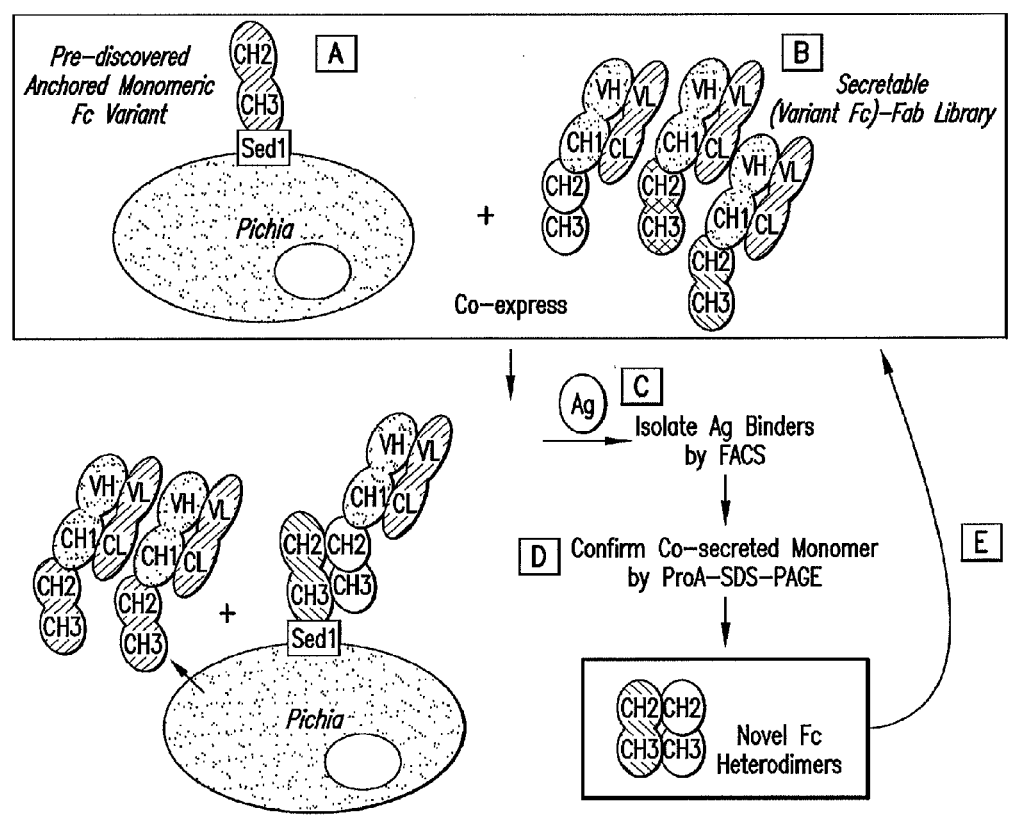
FIG. 8. The use of Fc-Sed1p display to discover novel heterodimeric Fc fragments for use in bispecifics and other applications. In this approach, an Fc mutant that lost its ability to homodimerize with self or heterodimerize with wild-type Fc can be displayed on a cell surface (A) and co-expressed with a library of H+L mutations where Fab region remains constant but CH2 and/or CH3 domains are mutated (B). Using surface display binding to Fab, cells that are positive for antigen binding can be isolated using FACS (C). Those cells will contain novel Fc variants that restore dimerization to the displayed bait-Fc. The culture supernatants can be assayed by SDS-PAGE to ensure monomeric secretion H+L containing the novel Fc (D). This exercise will result in identification of novel heterodimeric Fc pairs or partners that can be subject to subsequent engineering using the same assay (E).

As shown in FIG. 6, two rounds of sorting using biotinylated PCSK9 antigen resulted in significant enrichment of specific PCSK9 binders. The PCSK9 ELISA compared presorted library to round 2 sorted pools for both BP550 and BP551 (FIG. 7). Round 2 sorted pools from both libraries contained a high percentage of binders over the presorted populations. DNA sequencing confirmed the enrichment for new anti-PCSK9 binding sequences.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A method for determining if an antibody specifically binds to an antigen comprising contacting an antibody display system with said antigen; wherein the antibody display system comprises an isolated host cell wherein the host cell is selected from the group consisting of yeast and filamentous fungi; wherein said isolated host cell comprises
   (a) a polynucleotide encoding a bait comprising a heavy Fc immunoglobulin domain fused to a surface anchor polypeptide operably associated with a regulatable promotor;
   (b) one or more polynucleotides encoding an immunoglobulin light chain variable region; and
   (c) one or more polynucleotides encoding an immunoglobulin heavy chain variable region wherein the heavy chain is VH-CH1-CH2-CH3;
   comprising including expression from the regulatable promoter in said host cell; wherein in said isolated host cell the Fc of said bait complexes with an Fc/antigen-binding fragment comprising said immunoglobulin heavy and immunoglobulin light chains on the surface of the host cell; and determining if said Fc/antigen-binding fragment specifically binds to said antigen; wherein the antibody is determined to specifically bind said antigen if the monovalent antibody fragment specifically binds to said antigen and inhibiting expression of the bait from the regulatable promotor.

2. A method for identifying:
   (i) an antibody that binds specifically to an antigen; or
   (ii) a polynucleotide encoding an immunoglobulin heavy chain of said antibody and/or a polynucleotide encoding an immunoglobulin light chain of said antibody; comprising contacting an antibody display system with said antigen wherein the antibody display system comprises an isolated host cell wherein the host cell is selected from the group consisting of a yeast and filamentous fungi; wherein said isolated host cell comprises
   (a) a polynucleotide encoding a bait comprising a heavy Fc immunoglobulin domain fused to a surface anchor polypeptide operably associated with a regulatable promotor;
   (b) one or more polynucleotides encoding an immunoglobulin light chain variable region; and
   (c) one or more polynucleotides encoding an immunoglobulin heavy chain variable region wherein the heavy chain is VH-CH1-CH2-CH3;
   comprising including expression from the regulatable promoter in said host cell; wherein in said isolated host cell the Fc of said bait complexes with an Fc/antigen-binding fragment comprising said immunoglobulin heavy and immunoglobulin light chains on the surface of the host cell; and determining if said Fc/antigen-binding fragment specifically binds to said antigen; wherein the antibody or polynucleotide is identified if said specific binding to said antigen is observed and inhibiting expression of the bait from the regulatable promotor.

3. The method of claim 1 further comprising isolating the identified polynucleotides.

4. The method of claim 1 further comprising determining the affinity of said identified antibody for said antigen.

5. The method of claim 1 further comprising recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

6. The method of claim 1, wherein the host cell is *Pichia*.

7. The method of claim 1, wherein the host cell is *Pichia pastoris*.

8. The method of claim 1, wherein the host cell is *S. cerevisiae*.

9. The method of claim 2, wherein the host cell is *Pichia*.

10. The method of claim 2, wherein the host cell is *Pichia pastoris*.

11. The method of claim 2, wherein the host cell is *S. cerevisiae*.

* * * * *